US010758568B2

(12) United States Patent
Jarvis et al.

(10) Patent No.: US 10,758,568 B2
(45) Date of Patent: *Sep. 1, 2020

(54) REGULATORY T-CELLS FOR USE IN THE TREATMENT OF INFLAMMATORY DISORDERS OF THE HUMAN GASTROINTESTINAL TRACT

(71) Applicant: GENOVIE AB, Södertälje (SE)

(72) Inventors: Reagan Micheal Jarvis, Stockholm (SE); Magnus Thörn, Uppsala (SE)

(73) Assignee: GENOVIE AB, Södertälje (SE)

( * ) Notice: Subject to any disclaimer, the term of this patent is extended or adjusted under 35 U.S.C. 154(b) by 369 days.

This patent is subject to a terminal disclaimer.

(21) Appl. No.: 15/303,866

(22) PCT Filed: Apr. 16, 2015

(86) PCT No.: PCT/EP2015/058319
§ 371 (c)(1),
(2) Date: Oct. 13, 2016

(87) PCT Pub. No.: WO2015/158855
PCT Pub. Date: Oct. 22, 2015

(65) Prior Publication Data
US 2017/0035808 A1  Feb. 9, 2017

(30) Foreign Application Priority Data

Apr. 16, 2014 (DK) .................................. 2014 70223
Jul. 11, 2014 (DK) .................................. 2014 70438

(51) Int. Cl.
*A61K 35/17* (2015.01)
*C12N 5/0783* (2010.01)
*G01N 33/569* (2006.01)

(52) U.S. Cl.
CPC ............ *A61K 35/17* (2013.01); *C12N 5/0637* (2013.01); *G01N 33/56972* (2013.01)

(58) Field of Classification Search
None
See application file for complete search history.

(56) References Cited

U.S. PATENT DOCUMENTS

| 8,785,140 B2 * | 7/2014 | Hall ..................... A61K 35/17 435/7.24 |
| 9,637,527 B2 | 5/2017 | Loukas et al. |
| 9,726,666 B2 | 8/2017 | Winqvist et al. |
| 9,884,915 B2 | 2/2018 | Chamorro Perez et al. |
| 2009/0192434 A1 | 7/2009 | Thorn et al. |
| 2014/0294793 A1 * | 10/2014 | Littman ............... C12N 5/0636 424/93.71 |
| 2017/0038394 A1 | 2/2017 | Jarvis et al. |
| 2017/0038395 A1 | 2/2017 | Jarvis et al. |
| 2017/0165298 A1 | 6/2017 | Jarvis et al. |

FOREIGN PATENT DOCUMENTS

WO  WO-2012/054509  4/2012

OTHER PUBLICATIONS

Brusko et al. 2008. Clinical applications of regulatory T cells. European Journal of Immunology, vol. 38, pp. 901-937. (Year : 2008).*
Smigiel, Kate S., et al. "CCR7 provides localized access to IL-2 and defines homeostatically distinct regulatory T cell subsets." Journal of Experimental Medicine 211.1 (2014): 121-136. (Year: 2014).*
Du Pré, M. Fleur, et al. "CD62L neg CD38+ Expression on Circulating CD4+ T Cells Identifies Mucosally Differentiated Cells in Protein Fed Mice and in Human Celiac Disease Patients and Controls." The American journal of gastroenterology 106.6 (2011): 1147. (Year: 2011).*
Maul, Jochen, et al. "Peripheral and intestinal regulatory CD4+ CD25high T cells in inflammatory bowel disease." Gastroenterology 128.7 (2005): 1868-1878. (Year: 2005).*
Sun et al., "Small intestine lamina propria dendritic cells promote de novo generation of Foxp3 T reg cells via retinoic acid," Journal of Experimental Medicine, vol. 188, No. 2, pp. 1775-1785, Aug. 2007.
Siewert et al., "Induction of organ-selective CD4(+) regulatory T cell homing," European Journal of Immunology, vol. 37, No. 4, pp. 978-989, Apr. 2007.
Gerner et al., "Targeting T and B Lymphocytes in Inflammatory Bowel Diseases: Lessons from Clinical Trials," Digestive Diseases, vol. 31, No. 3-4, pp. 328-335, Jan. 2013.
Desreumaux et al., "Safety and Efficacy of Antigen-Specific Regulatory T-Cell Therapy for Patients with Refractory Crohn's Disease," Gastroenterology, vol. 143, No. 5, pp. 1207-1217, Nov. 2012.
Levings et al., "Human CD25+CD4+ T regulatory cells suppress naïve and memory T cell proliferation and can be expanded in vitro without loss of function," The Journal of Experimental Medicine, vol. 193, No. 11, pp. 1295-1301, Jun. 2001.
Corthay, "How do Regulatory T Cells Work?," Scandinavian Journal of Immunology, vol. 70, No. 4, pp. 326-336, Oct. 2009.
Nettenstrom et al., "An optimized multi-parameter flow cytometry protocol for human T regulatory cell analysis on fresh and viably frozen cells, correlation with epigenetic analysis, and comparison of cord and adult blood," Journal of Immunological Methods, vol. 387, No. 1-2, pp. 81-88, Jan. 2013.

(Continued)

*Primary Examiner* — Robert J Yamasaki
(74) *Attorney, Agent, or Firm* — Foley & Lardner LLP

(57) ABSTRACT

The present invention relates to a composition comprising an isolated CD4+ Treg cell population, wherein the Treg cells have signatures for i) identifying that the T-cells are CD4+ regulatory Tcells, ii) identifying that the Treg cells are tissue type tropic, i.e they can migrate to the diseased tissue, iii) optionally identifying that the Treg cells are tropic with respect to the diseased tissue, i.e. they are homing cells, iv) identifying that the Treg cells are emigrant cells, i.e. they originate from the target tissue, and v) optionally identifying that the Treg cells are retained in the target tissue and optionally one or more X-signatures and/or one or more Y-signatures and one ore more Z-signatures.

11 Claims, 39 Drawing Sheets

(56) References Cited

OTHER PUBLICATIONS

Figure 1:
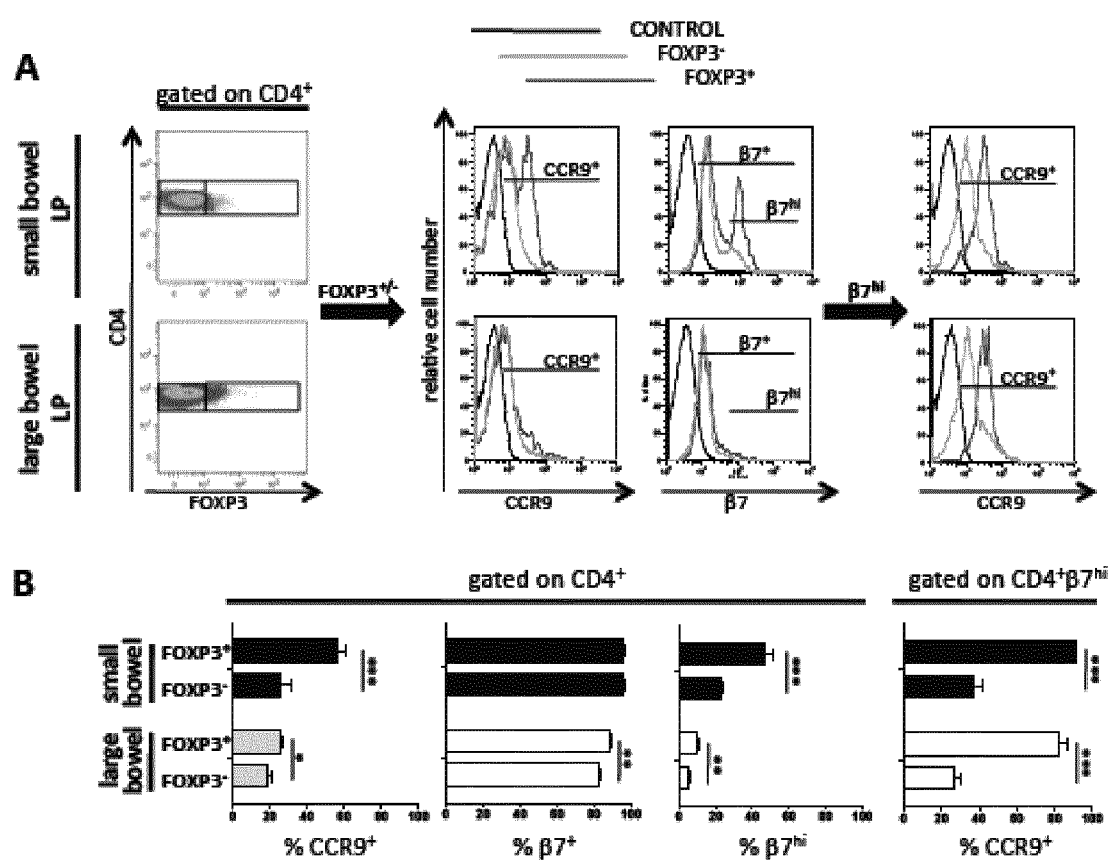

Putman et al., "Expansion of human regulatory T-cells from patients with type 1 diabetes," Diabetes, vol. 58, No. 3, pp. 652-662, Mar. 2009.
Riley et al., "Human T Regulatory Cell Therapy: Take a Billion or So and Call Me in the Morning," Immunity, vol. 30, No. 5, pp. 656-665, May 2009.
Scalzo-Inguanti et al., "CD38 identifies a hypo-proliferative IL-13-secreting CD4+ T-cell subset that does not fit into existing naïve and memory phenotype paradigms," European Journal of Immunology, vol. 41, No. 5, pp. 1298-1308, May 2011.
Gagliani et al., "Coexpression of CD49b and LAG-3 identifies human and mouse T regulatory type 1 cells," Nature Medicine, vol. 19, No. 6, pp. 739-746, Apr. 2013.
Engelhardt et al., "Homing in on an Acute Graft vs. Host Diesease: Tissue-Specific T Regulatory and Th17 Cells," Curr. Top Microbiol. Immunol., vol. 341, pp. 121-146, Jan. 2010.
International Search Report dated Jul. 2, 2015 in application No. PCT/EP2015/058319.
PCT International-Type Search Report dated Dec. 19, 2014 in Danish application No. 201470223.
Brusko, "Human Regulator T cells: role in autoimmune disease and therapeutic opportunities," Immunological Reviews (2008)vol. 112, pp. 371-390.
Geginat et al., "The CD4-centered universe of human T cell subsets," Seminars in Immunology, vol. 25, No. 4, pp. 252-262, Nov. 2013.
Horwitz et al., "Therapeutic polyclonal human CD8 + CD25 + Fox3 + TNFR2 + PD-L1 + regulatory cells induced ex-vivo," Clinical Immunology, vol. 149, No. 3, pp. 450-463, Aug. 2013.
International Search Report dated Jul. 2, 2015 in application No. PCT/EP2015/058320.
International Search Report dated Aug. 18, 2015 in application No. PCT/EP2015/058322.
International Search Report dated Sep. 15, 2015 in application No. PCT/EP2015/058323.
Jonuleit et al., "Identification and Functional Characterization of Human CD4+CD25+T Cells with Regulatory Properties Isolated from Peripheral Blood," The Journal of Experimental Medicine, vol. 193, No. 11, pp. 1285-1294, Jun. 2001.
Loftus et al., "PSC-IBD: a unique form of inflammatory bowel disease associated with primary sclerosing cholangitis," Gut, 2005, vol. 54, pp. 91-96.

Nigam et al., "Expansion of FOXP3$^+$ CD 8 T Cells with Suppressive Potential in Colorectal Mucosa Following a Pathogenic Simian Immunodeficiency Virus Infection Correlates with Dimished Antiviral T Cell Response and Viral Control," The Journal of Immunology, vol. 184, No. 4, pp. 1690-1701, Jan. 2010.
Office Action dated Jul. 27, 2018 in U.S. Appl. No. 15/303,867 (US 2017-0165298).
PCT International-Type Search Report dated Dec. 19, 2014 in Danish application No. 201470224.
PCT International-Type Search Report dated Dec. 19, 2014 in Danish application No. 201470225.
Suzuki et al., "CD8$^+$CD45RA$^+$CCR7$^+$FOXP3$^+$T Cells with Immunosuppressive Properties: A Novel Subset of Inducible Human Regulatory T Cells," The Journal of Immunology, vol. 189, No. 5, pp. 2118-2130, Jul. 2012.
Thomas et al., "Targeting leukocyte migration and adhesion in Crohn's disease and ulcerative colitis," Inflammopharmacology, vol. 20, No. 1, pp. 1-18, Dec. 2011.
Hoffman et al., "Polyclonal Expansion of Human CD4$^+$CD25$^+$ Regulatory T Cells," Methods in Molecular Biology, vol. 677, pp. 15-30 (2011) (Available online Sep. 13, 2010).
Jiang et al., "Generation and Expansion of Human CD4$^+$CD25$^+$ Regulatory T Cells with Indirect Allospecificity: Potential Reagents to Promote Donor-Specific Transplantation Tolerance," Transplantation, vol. 82, No. 12. pp. 1738-1743 (Dec. 2006).
Office Action dated Aug. 27, 2018 in U.S. Appl. No. 15/303,869 (US 2017-0038394).
Office Action dated Aug. 15, 2018 in U.S. Appl. No. 15/303,869 (US 2017-0038394).
Office Action dated Sep. 13, 2019 in U.S. Appl. No. 15/303,869 (US 2017-0038394).
Notice of Allowance dated Jan. 2, 2020 in U.S. Appl. No. 15/303,867 (US 2017-0165298).
Office Action dated Dec. 20, 2019 in U.S. Appl. No. 15/303,871 (US 2017-0038395).
Beissert et al., "Regulatory T Cells", Journal of Investigative Dermatology (2006) vol. 126, pp. 15-24.
Li et al., "Mechanism and Localization of CD8 Regulatory T Cells in a Heart Transplant Model of Tolerance", The Journal of Immunology (Jun. 2010) vol. 185, pp. 823-833.
Office Action dated Mar. 13, 2018 in U.S. Appl. No. 15/303,871 (US 2017-0038395).
Office Action dated Nov. 3, 2017 in U.S. Appl. No. 15/303,871 (2017-0038395).

* cited by examiner

Figure 31:
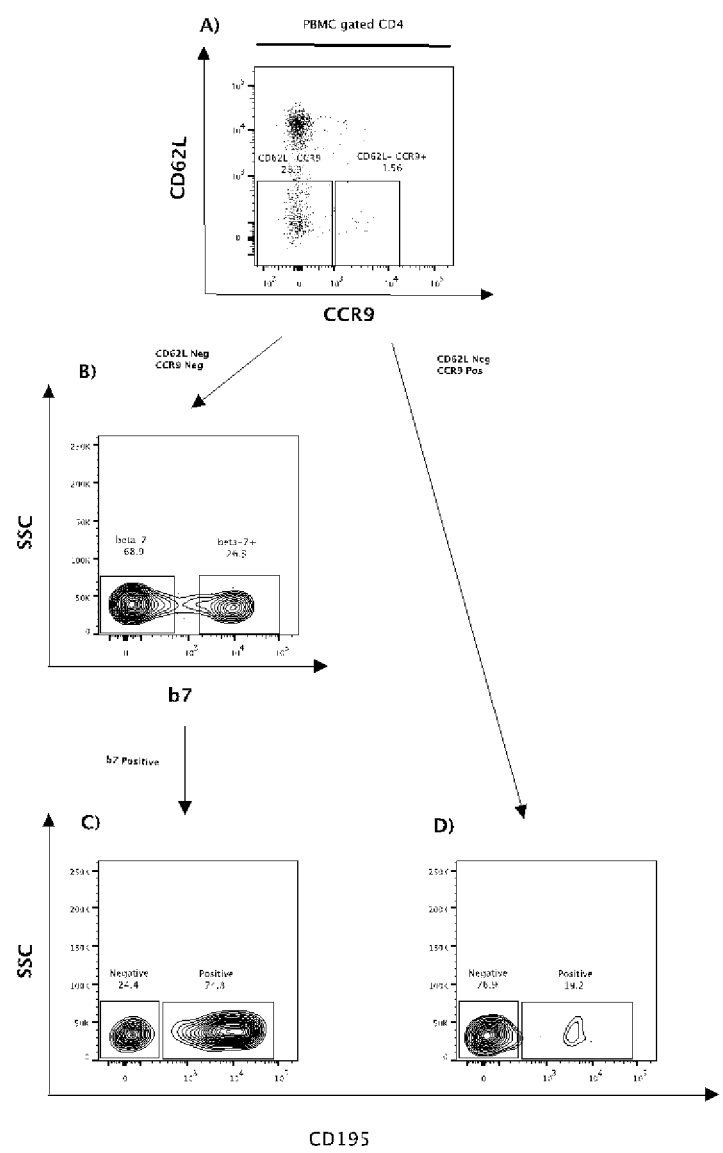

Figure 31 - continued

E)

| Marker | % pos CD4+CD62L-CCR9+ | % pos CD4+CD62L-CCR9-β7+ | Marker X-/X+ condition | Marker class |
|---|---|---|---|---|
| CD20 | 9.86 | 22.2 | X- | 3 |
| CD26 | 2(hi) | 22 (hi) | X- | 1 |
| CD61 | 13.4 | 27.7 | X- | 2 |
| CD63 | 18.1 | 39.8 | X- | 2 |
| CD97 | 6.33 (hi) | 21.8 (hi) | X- | 1 |
| CD130 | 37.9 | 21.4 | X+ | 3 |
| CD143 | 9.2 | 37.5 | X- | 1 |
| CD146 | 9.38 | 31.4 | X- | 2 |
| CD166 | 39.4 | 58 | X- | 3 |
| CD183 | 39.2 | 69.2 | X- | 2 |
| CD195 | 19.2 | 74.8 | X- | 1 |
| CD197 | 83.3 | 42.0 | X+ | 2 |
| CD200 | 32 | 10.1 | X+ | 2 |
| CD244 | 2.08 | 13.0 | X- | 2 |
| CD278 | 19 | 2.93 | X+ | 1 |

Figure 32:
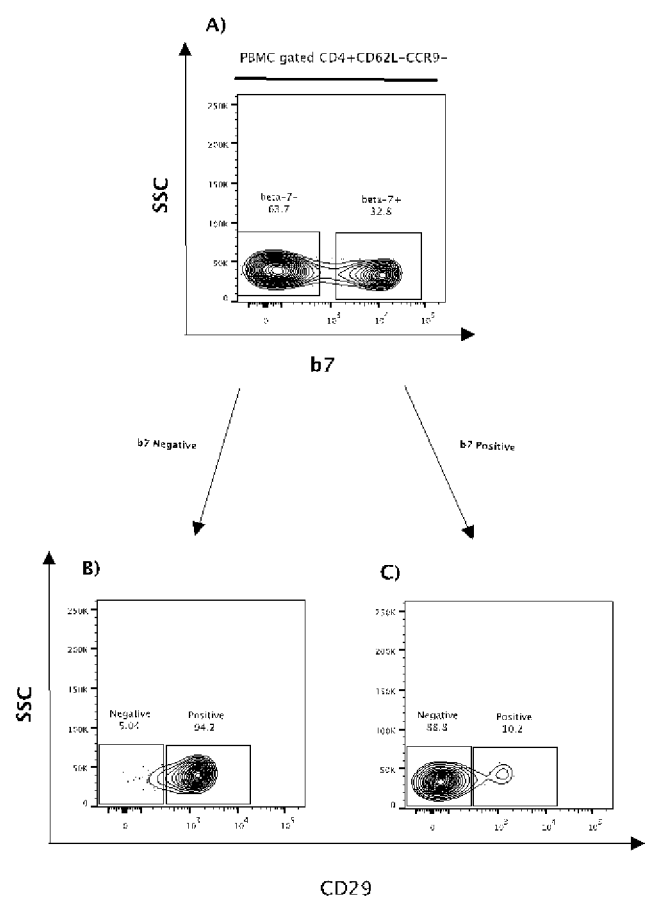

Figure 32 - continued

D)

| Marker | % pos CD4+CD62L-CCR9-b7+ | % pos CD4+CD62L-CCR9-b7- | Marker Y-/Y+ condition | Marker class |
|---|---|---|---|---|
| CD15s | 4.79 | 29.5 | Y- | 2 |
| CD27 | 80.5 | 51.8 | Y+ | 2 |
| CD29 | 10.2 | 94.2 | Y- | 1 |
| CD38 | 48.5 | 7.85 | Y+ | 1 |
| CD49b | 11.9 | 49.6 | Y- | 2 |
| CD49c | 19.8 | 93.6 | Y- | 1 |
| CD49e | 29.2 | 93.2 | Y- | 1 |
| CD71 | 14.8 | 32.2 | Y- | 3 |
| CD84 | 53.2 | 84 | Y- | 2 |
| CD102 | 0.75(hi) | 65.7(hi) | Y- | 1 |
| CD119 | 83.1 | 49.1 | Y+ | 2 |
| CD126 | 74 | 94.1 | Y- | 3 |
| CD134 | 41.5 | 57.8 | Y- | 3 |
| CD147 | 0.78(hi) | 85.7(hi) | Y- | 1 |
| CD151 | 53.8 | 37.1 | Y+ | 3 |
| CD161 | 73.1 | 41.7 | Y+ | 2 |
| CD171 | 11.8 | 31.5 | Y- | 3 |
| CD184 | 65.6 | 37.9 | Y+ | 2 |
| CD196 | 61.9 | 77.8 | Y- | 3 |
| CD227 | 29 | 43.8 | Y- | 3 |
| CD305 | 86.6 | 49.9 | Y+ | 2 |
| Cd49f | 71.1 | 98.8 | Y- | 3 |

Figure 33:
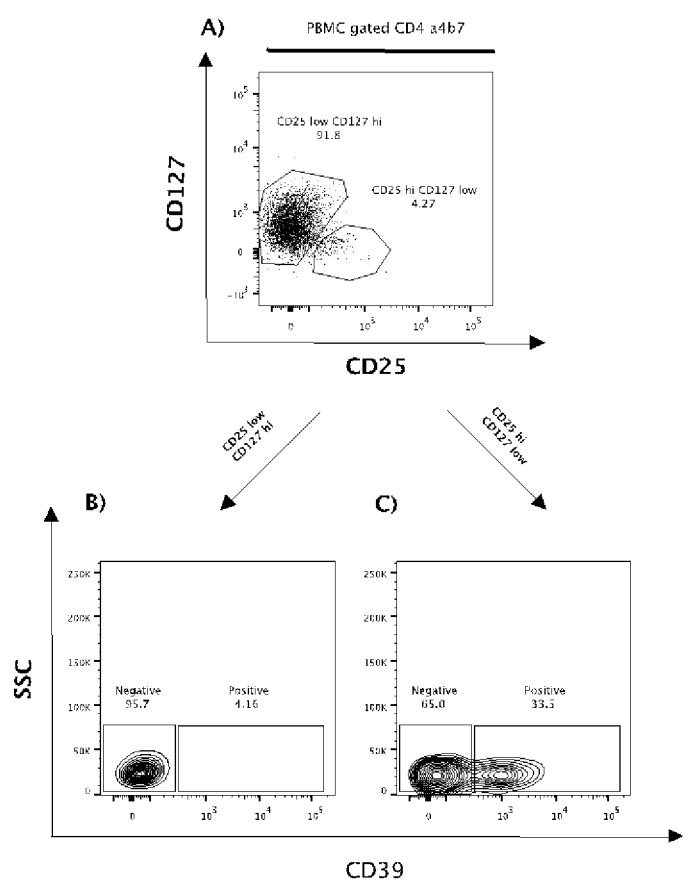

Figure 33 - continued

D)

| Marker | % pos CD4+α4β7+CD25$^{Hi}$CD127$^{Lo}$ | % pos CD4+α4β7+CD25$^{Lo}$CD127$^{Hi}$ | Marker Z-/Z+ condition | Marker class |
|---|---|---|---|---|
| CD6 | 18.8 | 68.6 | Z- | 2 |
| CD21 | 5.41 | 55.3 | Z- | 1 |
| CD35 | 2.82 | 39.3 | Z- | 1 |
| CD39 | 33 | 4.16 | Z+ | 2 |
| CD49c | 19.3 | 7.58 | Z+ | 3 |
| CD50 | 30(hi) | 10.4(hi) | Z+ | 2 |
| CD53 | 35.2(hi) | 19.7(hi) | Z+ | 3 |
| CD73 | 4.51 | 20.9 | Z- | 1 |
| CD84 | 27.6 | 42.3 | Z- | 3 |
| CD95 | 53.8 | 24.9 | Z+ | 3 |
| CD107a | 14.8 | 28.9 | Z- | 3 |
| CD109 | 12.4 | 3.9 | Z+ | 2 |
| CD122 | 73.3 | 13.3 | Z+ | 1 |
| CD226 | 49.6 | 92.3 | Z- | 2 |
| CD243 | 2.68 | 22.9 | Z- | 2 |
| CD268 | 42.3 | 18.5 | Z+ | 2 |
| CD274 | 14.3 | 26.7 | Z- | 2 |
| CLIP | 21 | 6.55 | Z+ | 1 |
| CD120b | 98.6 | 45.4 | Z+ | 1 |
| CD210 | 70.2 | 23.5 | Z+ | 2 | ered only the mucosa. UC has somewhat higher incidence figures than
REGULATORY T-CELLS FOR USE IN THE TREATMENT OF INFLAMMATORY DISORDERS OF THE HUMAN GASTROINTESTINAL TRACT

FIELD OF THE INVENTION

The present invention relates to cellular immunotherapy, in particular cellular immunotherapy with T-regulatory cells (Treg) for the treatment of inflammatory disorders of the human gastrointestinal tract including Crohn's disease and inflammation of the small bowel. The invention also relates to specific Treg cells and identification of immunosuppressive regulatory T-cells and to a method for expanding such cells.

BACKGROUND OF THE INVENTION

Inflammatory Bowel Disease (IBD) consists of two major types, namely Crohn's Disease (CD) and Ulcerative Colitis (UC). The number of new cases diagnosed per year, denoted annual incidence, of CD is 12-20 per 100,000 persons in Europe and North America. The numbers are 6 and 5 per 100,000 persons, respectively for Asia and the Middle East. New Zealand and Australia have the highest incidence figures, calculated to 27 and 50 per 100 000, respectively.

CD affects any part of the gastrointestinal tract, from mouth to anus, although in the majority of the cases the disease starts in the distal small bowel. CD involves the whole bowel wall (transmural inflammation). UC is restricted to inflammation in the colon and involves only the mucosa. UC has somewhat higher incidence figures than CD. There is a relationship between UC and CD by the fact that for about 15% of patients with colonic inflammation the diagnoses cannot be histopathologically distinguished. These patients are classified as having Indeterminate Colitis.

Common symptoms associated with IBD are abdominal pain, vomiting, diarrhoea, rectal bleeding, weight loss and cramps or spams in the lower abdomen. In severe cases the tendency to develop intra-abdominal fistulas gives rise to deep infections. Longstanding inflammation may lead to intestinal strictures. Surgical treatment usually involves percutaneous drainage of deep abscesses followed by surgery with resection of diseased bowel segments. Diagnosis is generally assessed by inflammatory markers in blood and stool, followed by ileo-colonoscopy with biopsies of pathological lesions.

First hand medical treatment consists of antibiotics and anti-inflammatory medication. There are several anti-inflammatory drugs, of which cortisone, azathioprine and antibodies against tumor necrosis factor (TNF) are the most frequently used. Even if a positive response is seen both short- and long-term, these medications often lead to adverse reactions and patients often need to reduce the dose to a minimum or taper them out completely.

Both CD and UC as inflammatory disorders have long been considered as a breakdown in immunoregulation in the tissues of the intestinal mucosa, representing the most immunologically active sites of the human body. The interaction between luminal flora and the adaptive immune system is considered critical to disease pathogenesis. T-cells are central to cell-mediated adaptive immunity. Two main subdivisions of T-cells may be defined, where T-effector cells (Teffs) can be generalised to represent pro-inflammatory activities, and Tregs to represent an anti-inflammatory check. Exuberant Teff activity is observable in both animal models and human disease alike, and has been attributed in recent years to a breakdown in Treg-mediated homoeostatic mechanisms. However, it remains difficult to attribute IBD immunopathogenesis to any specific functional or numerical defect in Tregs themselves. This is in no small part due to the fact that proposed in vivo mechanisms of Treg function in humans remain largely speculative. Regardless, numerous animal models and early clinical experiences have suggested that Treg cells could be harnessed for treatment of a range of inflammatory disorders, and particularly IBD.

T-cells impart control locally; individually influencing control of immune responses over relatively short distances. Consequently, the migration of T-cells between intestinal mucosa and other bodily compartments is a critical determinant of functional responses. Several large-scale clinical trials have focused on blocking Teff migration to intestinal tissues through pharmaceutical blockade of either adhesion molecules or chemoattractants critical for T-cell migration to intestinal mucosa, with mixed success.

A majority of the knowledge around the T-cell pathology of IBD is inferred from mouse models. It is well established that transfer of nave conventional T-cells into immune deficient mice results in a reaction against intestinal flora and establishment of intestinal inflammation, which can be rescued by co-transfer of Treg populations. It is also clear that Treg transfer into mice can resolve established intestinal inflammation. In the human setting, early indications of the link between intestinal tolerance and the human autoimmune syndrome were associated with FOXP3 mutations, the most common manifestation of which is chronic intestinal inflammation.

An accumulating body of data in patients with active and inactive IBD, and under various treatments, has yielded disparate results. Early studies suggested that the lamina propria (LP) of both CD and UC patients contained functional Tregs. Some studies have reported increased levels of Tregs in inflamed LP of IBD patients.

Considering the importance of migration of cells between the periphery and mucosal tissues, it is critical to consider the peripheral Treg pool in relation to direct observations of the inflamed mucosa. Several early studies have reported decreased levels of peripheral CD4$^+$ Treg cells in patients with active intestinal inflammation. However, the opposite has also been observed, with an increased frequency of peripheral CD4$^+$ Tregs in IBD patients, though lower frequency is often observed in active when compared to inactive disease.

Studies investigating Treg response in IBD patients undergoing anti-TNF therapies have reported increased levels of peripheral Tregs, particularly among clinical responders. However, other studies have reported no change in peripheral Treg frequency, and even a decreased frequency. Similar studies in rheumatoid arthritis have shown that responders to anti-TNF and methotrexate therapies show increased numbers of peripheral Treg cells. Curiously, addition of anti-TNF drugs to activated T-cells from patients resulted in the generation of Treg cells in vitro.

In summary, while it may be generally anticipated that IBD is characterised by a breakdown of immunotolerance in the intestinal mucosa, there is a lack of consistent correlation with an impaired Treg function or diminished abundance in patient tissues. This may be a result of as yet crude analytical methods to identify Treg cells, discriminate Treg subsets, and to assay their functional properties. It is also likely a function of still incomplete understanding of Treg origin and function in intestinal immune homeostasis. Recent insights into T-cell immunity in the intestinal mucosa have come from more detailed studies of T-cell migration and induction in the periphery.

The current invention relates to leveraging on observed migratory patterns of Treg cells in IBD patients, which allows identification of Treg subpopulations that may be purified as starting material for manufacture of cellular immunotherapeutic products.

However, there is a need to identify Treg cells that are suitable for use in cellular immunotherapy for the treatment of inflammatory and autoimmune diseases, notably IBD.

DESCRIPTION OF THE INVENTION

The present invention addresses the above-mentioned needs. The present invention aims to identify Treg cells with unique characteristics suitable for the above-mentioned uses, and particularly selected for treatment of inflammatory and autoimmune diseases of defined tissues relating to the gastrointestinal tract.

The present invention provides Treg cells with unique characters suitable for the above-mentioned use.

The present invention is based on the findings that specific homing receptor expression patterns can be used to identify regulatory T-cells in peripheral circulation as starting materials for therapeutic composition. The specific homing receptor expression pattern varies from tissue to tissue, but it is contemplated that the nature of the signatures (expression pattern) is the same, irrespective of the diseased tissue in question. Thus, the present invention is based on the surprising findings that e.g. Crohn's disease is not a disease defined by a deficiency of Tregs per se, but a deficiency in their ability to recirculate to the diseased tissue, in this case the small bowel. The overall number of Tregs in peripheral circulation is trending toward a deficiency in CD compared with controls. However with respect to recent emigrants (i.e. regulatory T-cells emigrating from the diseased area), that are also likely destined for recirculation to the mucosa, the present inventors observed a trend towards an increased number of Tregs. In addition these recent emigrants and recirculating T-cells had a marked reduction in CCR9 expression (the homing marker related to the small bowel). These findings have led to identification of specific signatures, that must be presented on Tregs in order to be suitable for therapeutic use. Further, expression of homing factors related to the diseased tissue on those specific Tregs will direct them to the location of the inflammation.

Thus, it was observed that Treg cells obtained from patients suffering from CD have markedly diminished CCR9 marking on Tregs. Treg CCR9 expression is induced within the small bowel lymphoid tissues in parallel with antigen engagement. Export of CCR9-expressing Tregs from the mucosal lymphoid tissues allows recirculation of these cells to regional mucosal tissue. This process is important for establishment of regional and subsequently systemic tolerance. It is anticipated that by targeting varying mucosal tropic and emigrant Treg populations, that the T-cell receptor clonotypes of these populations are restricted to those relevant to tissue-related and disease-related antigens.

These findings suggest that Tregs with a specific expression pattern are useful in the treatment of inflammatory or autoimmune diseases of the gastrointestinal tract. The Treg cells should have specific signatures that
i) identify that the cells are regulatory T-cells
ii) identify that the regulatory T-cells are tissue type tropic, i.e. they can migrate to the diseased tissue, iii) optionally, identify that the Treg cells are diseased tissue tropic, i.e. they are so-called homing cells that can localize in the diseased region of the gastrointestinal tract,
iv) identify that the regulatory T-cells are emigrant cells, i.e. they originate from the target tissue (educated cells), and
v) optionally identify that the regulatory T-cells are retained in the target tissue after administration to a subject,
wherein the T-cells have the signatures i), ii) and iv) and optionally iii) and/or v); or the T-cells have the signatures i), ii), iv) and v) and optionally iii), or the T-cells have the signatures i), ii), iv) and v) and optionally iii).

In the present context the term "tissue type" means the specific type of tissue present in the diseased area. As an example the tissue type in relation to Crohn's disease in the small bowel is mucosa and the mucosa is healthy or diseased tissue from the gastrointestinal tract, i.e. the tissue type is not narrowly defined as being exactly from the diseased mucosa, but may be from another part of the gastrointestinal tract. In preferred aspect the tissue type is from the diseased tissue.

In the present context the term "target tissue" means the specific type of tissue present in the diseased area. As an example the target tissue in relation to Crohn's disease in the small bowel is mucosa from the small bowel.

In the present context the terms "tissue type tropic" and "diseased tissue tropic" denotes tropism in relation to the "tissue type and anatomical location" (i.e. tissue in general) and in relation to the "target tissue" (i.e. specific diseased tissue region), respectively. The tropism may be to the diseased tissue as well as to the healthy tissue in the diseased area, tissue region or tissue type. It should be noted that immigration of cells from peripheral blood into the stromal/parenchyma of any tissue is mediated by factors intrinsic to the tissue itself, and by factors presented by the vasculature permeating said the tissue. As such, tissue tropism is an interaction of factors expressed by migratory cells with both tissue-centric and tissue vasculature-centric factors. This duality results in often-significant overlap in the functional elements of migratory cells with tropism towards related yet distinct tissue types and tissue subtypes.

The specific types of Tregs in accordance with the concept of the present invention are described in detail herein. It is contemplated that the Treg cells are suitable for use in the treatment of inflammatory diseases of the gastrointestinal tract and the proof of concept relates to inflammation of the small bowel in particular, but through mucosal tropism also for inflammatory diseases located in the whole mucosal gastrointestinal tract.

As mentioned above CD can affect the whole gastrointestinal tract, notably the distal part of the small bowel, the colon, the proximal part of the gastrointestinal tract or the anal canal and perianal areas. It is envisaged that the Treg cells suitable for use in the treatment of CD mainly have the same signatures irrespective of which part of the gastrointestinal tract that is affected apart from the signature that identifies that the regulatory T-cells are gastrointestinal tropic. It is believed that the signature in this respect must be specific, i.e. proximal gastrointestinal tract tropic, large bowel tropic, small bowel tropic, anal canal tropic etc. dependent on the localisation of CD.

The present invention has a proof of concept based on specific Treg cells for use in the treatment of CD in the small bowel. The CD4$^+$ Treg cells should have specific signatures as defined above. It is generally preferred that the Treg cells should have specific signatures that i) identify that the cells are regulatory T-cells,
ii) identify that the regulatory T-cells are tissue type tropic, in this case mucosal tropic, i.e. they can migrate to the diseased tissue (mucosal),
iii) optionally, identify that the Treg cells are diseased tissue tropic, in case of CD in the small bowel the Treg cells are small bowel tropic, i.e. they are so-called homing cells that can localize in the small bowel,
iv) identify that the regulatory T-cells are emigrant cells, i.e. they originate from the target tissue, i.e. in the case of CD in the small bowel the Tregs originate from the small bowel (educated cells), and
v) optionally, identify that the regulatory T-cells are retained in the diseased tissue (the small bowel) after administration to a subject.

As seen from the above it is generally preferred that the signatures i), ii) and iv) are mandatory when the Tregs are used in the treatment of CD in the small bowel. However, it is contemplated that, different treatment strategies, or treatment of inflammatory diseases such as Crohn's disease affecting other parts of the gastrointestinal tract, do not require the same signatures; thus, it is contemplated that the Tregs must have the signatures T-cells have the signatures i), ii) and iv) and optionally iii) and/or v); or the T-cells have the signatures i), ii), iv) and v) and optionally iii), or the T-cells have the signatures i), ii), iv) and v) and optionally iii).

In analogous manner when the CD is localized in the colon the Treg cells should have specific signatures that
i) identify that the cells are regulatory T-cells,
ii) identify that the regulatory T-cells are mucosal tropic, i.e. they can migrate to the diseased tissue (mucosa),
iii) optionally, identify that the Treg cells are colon tropic, i.e. they are so-called homing cells that can localize in the colon,
iv) identify that the regulatory T-cells are emigrant cells, i.e. they originate from the target tissue, i.e. from the mucosa, (educated cells), and
v) optionally, identify that the regulatory T-cells are retained in the target tissue, i.e. the colon, after administration to a subject.

Tregs for treatment of CD in other locations of the gastrointestinal tract have the same kind of signatures, but the signatures relate to the target tissue of the gastrointestinal tract.

In general Treg cells are defined as a type of $CD4^+$ cell that negatively regulates the immune responses. It is further defined by expression of the transcription factor FOXP3 and comes in two versions, the induced Tregs, which develops from mature T-cells in periphery, and the natural Tregs, which develops from immature T-cells in the thymus. The $CD4^+$ Treg cells should have specific signatures that
i) identify that the cells are regulatory T-cells,
ii) identify that the regulatory T-cells are tissue type tropic, i.e. they can migrate to the diseased tissue (mucosa),
iii) optionally, identify that the Treg cells are diseased tissue tropic, i.e. they are so-called homing cells that can localize in the diseased part of the gastrointestinal tract,
iv) identify that the regulatory T-cells are emigrant cells, i.e. they originate from the target tissue (educated cells), and
v) optionally, identify that the regulatory T-cells are retained in the target tissue of the gastrointestinal tract after administration to a subject.

The present inventors have found that a preferred signature for identifying that the Treg cells are mucosal tropic is $\alpha 4\beta 7^+$, $\alpha 4^+\beta 7^+$, preferably $\alpha 4\beta 7^+$.

A preferred signature for identifying that the Treg cells can be retained in mucosal tissue is $\alpha 4^+\alpha E^+\beta 7^{high}$. $\alpha 4^+\alpha E^+\beta 7^{high}$ in some instances may also be considered as an identifier of mucosal emigration.

The specific types of Tregs in accordance with the present invention are described in detail herein using CD localized in the small bowel as an example, but without limiting the invention thereto. It is contemplated that the Treg cells are suitable for use in the treatment of inflammatory diseases of the small bowel, especially in the treatment of CD.

If CD is located to the small bowel, the diseased as well as the target tissue is the small bowel.

Thus, the identification of a specific Treg cell population in peripheral blood, which is likely to represent mucosal emigrants with a strong propensity to recirculate to the small bowel, presents a further means to identify Treg cells based on homing receptor patterns for adoptive immunotherapy. Coupled to Treg markers and, optionally a marker set for cells marked for mucosal retention, the present inventors were able to identify four overlapping subsets of Tregs with therapeutic potential in CD located in the small bowel. Analogously, Treg cells with therapeutic potential in CD located in other parts of the gastrointestinal tract can be identified or Tregs with therapeutic potential in other inflammatory diseases of the gastrointestinal tract.

1. $CD4^+$ Treg cells that have signatures for
i) identifying that the T-cells are regulatory T-cells,
ii) identifying that the Treg cells are mucosal tropic, i.e. they can migrate to mucosal tissue,
iv) identifying that the Treg cells are emigrant cells, i.e. they originate from the bowel.

2. $CD4^+$ Treg cells that have signatures for
i) identifying that the T-cells are regulatory T-cells,
ii) identifying that the Treg cells are mucosal tropic, i.e. they can migrate to mucosal tissue,
iii) identifying that the Treg cells are small bowel tropic, i.e. homing cells that can localize in the small bowel, and
iv) identifying that the Treg cells are emigrant cells, i.e. they originate from the bowel.

3. $CD4^+$ Treg cells that have signatures for
i) identifying that the T-cells are regulatory T-cells,
ii) identifying that the Treg cells are mucosal tropic, i.e. they can migrate to mucosal tissue,
iv) identifying that the Treg cells are emigrant cells, i.e. they originate from the bowel, and
v) identifying that the Treg cells are marked for mucosal retention.

4. $CD4^+$ Treg cells that have signatures for
i) identifying that the T-cells are regulatory T-cells,
ii) identifying that the Treg cells are mucosal tropic, i.e. they can migrate into mucosal tissue,
iii) identifying that the Treg cells are small bowel tropic, i.e. homing cells that can localize in the small bowel,
iv) identifying that the Treg cells are emigrant cells, i.e. they originate from the bowel, and
v) identifying that the Treg cells are marked for mucosal retention.

As mentioned herein before, the preferred $CD4^+$ Treg cells are $CD4^+$ Treg cells that have signatures for
i) identifying that the T-cells are regulatory Tcells,
ii) identifying that the Treg cells are mucosal tropic, i.e. they can migrate into mucosal tissue,
iii) optionally, identifying that the Treg cells are small bowel tropic, i.e. homing cells that can localize in the small bowel,
iv) identifying that the Treg cells are emigrant cells, i.e. they originate from the bowel, and v) optionally identifying that the Treg cells are marked for mucosal retention.

Other alternatives may be derived from the description herein.

As will be explained in detail herein, the preferred signature for identifying that the T-cells are regulatory T-cells is, $CD4^+CD25^{hi}$, $CD4^+CD25^{hi}CD127^{lo}$, or $CD4^+Z_n$, where Z is a functional marker and n is an integer of 1 or more. Functional markers Z are described herein below.

The preferred signature for identifying that the Treg cells are mucosal tropic is $\alpha4\ \beta7^+$ or $\alpha4^+\beta7^+$ or in combination with one or more Y signatures as defined herein.

The preferred signature for identifying that the Treg cells are small bowel tropic, i.e. homing cells, is $CCR9^+$ or in combination with one or more X signatures as defined herein.

The preferred signature for identifying that the Treg cells are educated cells (emigrants) is $CD62L^-$ and/or $CD38^+$ and/or $\alpha4^+\alpha E^+\beta7^{high}$, one or more X signatures and/or one or more Y signatures as defined herein.

The preferred signature for identifying that the Treg cells can be retained in mucosal tissue is $\alpha4^+\alpha E^+\beta7^{high}$ or $\alpha4^-\alpha E^+\beta7^+$, and/or one or more of any of X, Y and Z signatures as defined herein.

Other signatures are $CD45RA^-/CD45RO^+$, and/or $CCR7^-$

Thus, in preferred aspect of the invention and relating to inflammatory disease of the small bowel, the Treg cells are selected from the following:
$CD4^+CD25^{hi}\alpha4\beta7^+CD62L^-CD38^+$
$CD4^+CD25^{hi}\alpha4^+\beta7^+CD62L^-CD38^+$
$CD4^+CD25^{hi}CD127^{lo}\alpha4\beta7^+CD62L^-CD38^+$
$CD4^+CD25^{hi}CD127^{lo}\alpha4^+\beta7^+CD62L^-CD38^+$
$CD4^+CD25^{hi}\alpha4\beta7^+CD62L^-$
$CD4^+CD25^{hi}\alpha4^+\beta7^+CD62L^-$
$CD4^+CD25^{hi}CD127^{lo}\alpha4\beta7^+CD62L^-$
$CD4^+CD25^{hi}CD127^{lo}\alpha4^+\beta7^+CD62L^-$
$CD4^+CD25^{hi}\alpha4\beta7^+CD62L^-CD38^+CCR9^+$
$CD4^+CD25^{hi}\alpha4^+\beta7^+CD62L^-CD38^+CCR9^+$
$CD4^+CD25^{hi}CD127^{lo}\alpha4\beta7^+CD62L^-CD38^+CCR9^+$
$CD4^+CD25^{hi}CD127^{lo}\alpha4^+\beta7^+CD62L^-CD38^+CCR9^+$
$CD4^+CD25^{hi}\alpha4\beta7^+CD62L^-CCR9^+$
$CD4^+CD25^{hi}\alpha4^+\beta7^+CD62L^-CCR9^+$
$CD4^+CD25^{hi}CD127^{lo}\alpha4\beta7^+CD62L^-CCR9^+$
$CD4^+CD25^{hi}CD127^{lo}\alpha4^+\beta7^+CD62L^-CCR9^+$
$CD4^+CD25^{hi}\alpha4\beta7^{high}\alpha E^+CD62L^-CD38^+$
$CD4^+CD25^{hi}\alpha4^+\beta7^{high}\alpha E^+CD62L^-CD38^+$
$CD4^+CD25^{hi}CD127^{lo}\alpha4\beta7^{hi}\alpha E^+CD62L^-CD38^+$
$CD4^+CD25^{hi}CD127^{lo}\alpha4^+\beta7^{hi}\alpha E^+CD62L^-CD38^+$
$CD4^+CD25^{hi}\alpha4\beta7^{high}\alpha E^+CD62L^-$
$CD4^+CD25^{hi}\alpha4^+\beta7^{high}\alpha E^+CD62L^-$
$CD4^+CD25^{hi}CD127^{lo}\alpha4\beta7^{hi}\alpha E^+CD62L^-$
$CD4^+CD25^{hi}CD127^{lo}\alpha4^+\beta7^{hi}\alpha E^+CD62L^-$
$CD4^+CD25^{hi}\alpha4\beta7^{high}\alpha E^+CD38^+$
$CD4^+CD25^{hi}\alpha4^+\beta7^{high}\alpha E^+CD38^+$
$CD4^+CD25^{hi}CD127^{lo}\alpha4\beta7^{hi}\alpha E^+CD38^+$
$CD4^+CD25^{hi}CD127^{lo}\alpha4^+\beta7^{hi}\alpha E^+CD38^+$
$CD4^+CD25^{hi}\alpha4\beta7^{high}\alpha E^+CD62L^-CD38^+CCR9^+$
$CD4^+CD25^{hi}\alpha4^+\beta7^{high}\alpha E^+CD62L^-CD38^+CCR9^+$
$CD4^+CD25^{hi}CD127^{lo}\alpha4\beta7^{hi}\alpha E^+CD62L^-CD38^+CCR9^+$
$CD4^+CD25^{hi}CD127^{lo}\alpha4^+\beta7^{hi}\alpha E^+CD62L^-CD38^+CCR9^+$
$CD4^+CD25^{hi}\alpha4\beta7^{high}\alpha E^+CD62L^-CCR9^+$
$CD4^+CD25^{hi}\alpha4^+\beta7^{high}\alpha E^+CD62L^-CCR9^+$
$CD4^+CD25^{hi}CD127^{lo}\alpha4\beta7^{hi}\alpha E^+CD62L^-CCR9^+$
$CD4^+CD25^{hi}CD127^{lo}\alpha4^+\beta7^{hi}\alpha E^+CD62L^-CCR9^+$
$CD4^+CD25^{hi}\alpha4\beta7^{high}\alpha E^+CD38^+CCR9^+$
$CD4^+CD25^{hi}\alpha4^+\beta7^{high}\alpha E^+CD38^+CCR9^+$
$CD4^+CD25^{hi}CD127^{lo}\alpha4\beta7^{hi}\alpha E^+CD38^+CCR9^+$
$CD4^+CD25^{hi}CD127^{lo}\alpha4^+\beta7^{hi}\alpha E^+CD38^+CCR9^+$ In all the specific Treg cell populations described herein (such as those mentioned above) it is within the scope of the present invention that whenever
a) $CD4^+$ is mentioned it may be replaced with $CD4^+CD25^{hi}$ or $CD4^+CD25^{hi}CD127^{lo}$,
b) $CD62L^-$ is mentioned this signature may be replaced or supplemented with $CD38^+$ or with $\alpha4^+\alpha E^+\ \beta7^{high}$ or with $CD38^+\alpha4^+\alpha E^+\ \beta7^{high}$, and whenever
c) $\alpha4^+\beta7^{high}\alpha E^+$ is mentioned it may be replaced with $\alpha4^+\beta7^+\alpha E^+$.

As described herein in details the above $CD4^+$ Treg cells may comprise one or more further signatures relating to the emigrant and/or immigrant nature of the $CD4^+$ Treg cells. Such signatures are denoted "X" or "Y", where X is the signature indicating that the Tregs can localize, has emigrated from, or is marked for preferential retention in the specific part of the gastrointestinal tract that is diseased, and where Y is the signature indicating that the Tregs can localize to any mucosal surface. As explained herein examples of signatures X and Y are given in FIGS. 31 and 32. The $CD4^+$ Treg cells may also comprises signatures of functional nature, Z. Z indicates regulatory function, or indicates restriction of inflammatory function, such a signature is required in aspect i) in marking target $CD4^+$ Treg identity. However, as explained herein signatures relating to emigrant cells from thymus and immigrant cells from the peripheral blood to the lymph nodes should be excluded. In other preferred aspects such an invention and relating to CD in other parts of the gastrointestinal tract than the small bowel, the Treg cells are selected from the above- and below mentioned, wherein the Treg cells further may contain one or more of X, one or more of Y and/or one or more of Z.
$CD4^+CD25^{hi}\alpha4\beta7^+CD62L^-CD38^+X/Y/Z$
$CD4^+CD25^{hi}\alpha4^+\beta7^+CD62L^-CD38^+X/Y/Z$
$CD4^+CD25^{hi}CD127^{lo}\alpha4\beta7^+CD62L^-CD38^+X/Y/Z$
$CD4^+CD25^{hi}CD127^{lo}\alpha4^+\beta7^+CD62L^-CD38^+X/Y/Z$
$CD4^+CD25^{hi}\alpha4\beta7^+CD62L^-X/Y/Z$
$CD4^+CD25^{hi}\alpha4^+\beta7^+CD62L^-X/Y/Z$
$CD4^+CD25^{hi}CD127^{lo}\alpha4\beta7^+CD62L^-X/Y/Z$
$CD4^+CD25^{hi}CD127^{lo}\alpha4^+\beta7^+CD62L^-X/Y/Z$
$CD4^+CD25^{hi}\alpha4\beta7^+CD38^+X/Y/Z$
$CD4^+CD25^{hi}\alpha4^+\beta7^+CD38^+X/Y/Z$
$CD4^+CD25^{hi}CD127^{lo}\alpha4\beta7^+CD38^+X/Y/Z$
$CD4^+CD25^{hi}CD127^{lo}\alpha4^+\beta7^+CD38^+X/Y/Z$
$CD4^+CD25^{hi}\alpha4\beta7^+CD62L^-CD38^+CCR9^+X/Y/Z$
$CD4^+CD25^{hi}\alpha4^+\beta7^+CD62L^-CD38^+CCR9^+X/Y/Z$
$CD4^+CD25^{hi}CD127^{lo}\alpha4\beta7^+CD62L^-CD38^+CCR9^+X/Y/Z$
$CD4^+CD25^{hi}CD127^{lo}\alpha4^+\beta7^+CD62L^-CD38^+CCR9^+X/Y/Z$
$CD4^+CD25^{hi}\alpha4\beta7^+CD62L^-CCR9^+X/Y/Z$
$CD4^+CD25^{hi}\alpha4^+\beta7^+CD62L^-CCR9^+X/Y/Z$
$CD4^+CD25^{hi}CD127^{lo}\alpha4\beta7^+CD62L^-CCR9^+X/Y/Z$
$CD4^+CD25^{hi}CD127^{lo}\alpha4^+\beta7^+CD62L^-CCR9^+X/Y/Z$
$CD4^+CD25^{hi}\alpha4\beta7^+CD38^+CCR9^+X/Y/Z$
$CD4^+CD25^{hi}\alpha4^+\beta7^+CD38^+CCR9^+X/Y/Z$
$CD4^+CD25^{hi}CD127^{lo}\alpha4\beta7^+CD38^+CCR9^+X/Y/Z$
$CD4^+CD25^{hi}CD127^{lo}\alpha4^+\beta7^+CD38^+CCR9^+X/Y/Z$
$CD4^+CD25^{hi}\alpha4\beta7^{high}\alpha E^+CD62L^-CD38^+X/Y/Z$
$CD4^+CD25^{hi}\alpha4^+\beta7^{high}\alpha E^+CD62L^-CD38^+X/Y/Z$
$CD4^+CD25^{hi}CD127^{lo}\alpha4\beta7^{hi}\alpha E^+CD62L^-CD38^+X/Y/Z$
$CD4^+CD25^{hi}CD127^{lo}\alpha4^+\beta7^{hi}\alpha E^+CD62L^-CD38^+X/Y/Z$
$CD4^+CD25^{hi}\alpha4\beta7^{high}\alpha E^+CD62L^-X/Y/Z$
$CD4^+CD25^{hi}\alpha4^+\beta7^{high}\alpha E^+CD62L^-X/Y/Z$
$CD4^+CD25^{hi}CD127^{lo}\alpha4\beta7^{hi}\alpha E^+CD62L^-X/Y/Z$
$CD4^+CD25^{hi}CD127^{lo}\alpha4^+\beta7^{hi}\alpha E^+CD62L^-X/Y/Z$ CD4$^+$CD25$^{hi}$α4β7$^{high}$αE$^+$CD38$^+$X/Y/Z
CD4$^+$CD25$^{hi}$α4$^+$β7$^{high}$αE$^+$CD38$^+$X/Y/Z
CD4$^+$CD25$^{hi}$CD127$^{lo}$α4β7$^{hi}$αE$^+$CD38$^+$X/Y/Z
CD4$^+$CD25$^{hi}$CD127$^{lo}$α4$^+$β7$^{hi}$αE$^+$CD38$^+$X/Y/Z
CD4$^+$CD25$^{hi}$α4β7$^{high}$αE$^+$CD62L$^-$CD38$^+$CCR9$^+$X/Y/Z
CD4$^+$CD25$^{hi}$α4$^+$β7$^{high}$αE$^+$CD62L$^-$CD38$^+$CCR9$^+$X/Y/Z
CD4$^+$CD25$^{hi}$CD127$^{lo}$α4β7$^{hi}$αE$^+$CD62L$^-$CD38$^+$CCR9$^+$X/Y/Z
CD4$^+$CD25$^{hi}$CD127$^{lo}$α4$^+$β7$^{hi}$αE$^+$CD62L$^-$CD38$^+$CCR9$^+$X/Y/Z
CD4$^+$CD25$^{hi}$α4β7$^{high}$αE$^+$CD62L$^-$CCR9$^+$X/Y/Z
CD4$^+$CD25$^{hi}$α4$^+$β7$^{high}$αE$^+$CD62L$^-$CCR9$^+$X/Y/Z
CD4$^+$CD25$^{hi}$CD127$^{lo}$α4β7$^{hi}$αE$^+$CD62L$^-$CCR9$^+$X/Y/Z
CD4$^+$CD25$^{hi}$CD127$^{lo}$α4$^+$β7$^{hi}$αE$^+$CD62L$^-$CCR9$^+$X/Y/Z
CD4$^+$CD25$^{hi}$α4β7$^{high}$αE$^+$CD38$^+$CCR9$^+$X/Y/Z
CD4$^+$CD25$^{hi}$α4$^+$β7$^{high}$αE$^+$CD38$^+$CCR9$^+$X/Y/Z
CD4$^+$CD25$^{hi}$CD127$^{lo}$α4β7$^{hi}$αE$^+$CD38$^+$CCR9$^+$X/Y/Z
CD4$^+$CD25$^{hi}$CD127$^{lo}$α4$^+$β7$^{hi}$αE$^+$CD38$^+$CCR9$^+$X/Y/Z X/Y/Z means that at least one of X, and/or at least one of Y and/or at least one of Z may be present and X, Y and Z may be X$^+$ or X$^-$, Y$^-$ or Y$^-$, Z$^+$ or Z$^-$, and one or more X, Y and/or Z may be present. X is a signature indicating that the Tregs can localize, have emigrated from or are marked for preferential retention in the specific part of the small bowel that is diseased. X may be X$^+$ or X may be X$^-$. Y is the signature indicating that the Tregs can localize to any mucosal surface. Y may be Y$^+$ or Y may be Y$^-$. Z is a signature indicating that the T-cells can exercise immunosuppressive functions or do not promote pro-inflammatory activities. Z may be Z$^+$ or Z may be Z$^-$.

Irrespective of the gastrointestinal location of the inflammation, any of the signatures may also comprise CD62L$^-$ and/or CD38$^+$.

The CD4$^+$ Treg cells may also contain the signatures CD69$^+$ and/or CD44$^+$ to denote recent activation.

As described in the experimental part herein it was found that β7$^{hi}$ cells express higher levels of β7 owing to the fact that they require additional β7 to pair with αE, suggesting β7$^{hi}$ cells express both the α4β7 and αEβ7 integrin pairs. The significance of this is that α4β7 is thought to be required for migration into mucosal tissues, while αEβ7 is required for retention. αEβ7 may also in some instances be considered to represent an identifier of recent mucosal emigration.

As mentioned above, the present invention relates to specific Tregs for treating inflammatory disorders of the bowel. To this end it is important to identify important subtypes of Treg cells, enabling their accurate purification from human tissues. This knowledge has been built on unique analyses of specimens from patients with CD, healthy individuals, and in some respects from patients with colorectal cancer.

With regard to markers X and Y in the above claims, relating to markers that denote a signature indicating tissue localisation, emigration or immigration, further analyses revealed markers of particular interest.

FIG. 31 shows an example of different adhesion molecule expression in the CD4$^+$CD62L$^-$CCR9$^+$ population in comparison to the CD4$^+$CD62L$^-$CCR9$^-$β7$^+$ population that is targeted to mucosal tissues in general (FIG. 31 A to D). In this example, CD195 (CCR5) is restricted in the CD4$^+$ CD62L$^-$CCR9$^+$ population. It is thus anticipated that CD195 may be used as a marker of preferred condition X–, with which to select for mucosal emigrant, immigrant and educated CD4+ Treg cells with small bowel tropism. The table presented in FIG. 31 E summarises other migratory-type markers associated with the CD4$^+$CD62L$^-$CCR9$^+$ population. The markers positively correlated are of condition X+ and the markers negatively correlated are of condition X–. In the preferred aspect markers denoted X+ are used as a positive selection marker and markers denoted X– are used as a negative selection marker for the purification of mucosal emigrant, immigrant and educated CD4+ Treg cells with small bowel tropism. Each marker in this table is also assigned a class, where class 1 represents a strong association with the CD4$^+$CD62L$^-$CCR9$^+$ population and high functional significance. Class 2 represents a strong association with the CD4$^+$CD62L$^-$CCR9$^+$ population or high functional significance. Class 3 represents weak association and/or uncertain functional significance.

Any of these markers, X, can be included in a CD4$^+$ Treg cell population according to the invention or used in a method of the invention to select the right signature pattern on the CD4$^+$ Treg cells. As shown in FIG. 31 markers of class 1 include CD26, CD97, CD143, CD195 and CD278. Markers of class 2 include CD61, CD63, CD146, CD183, CD197, CD200, and CD244. Markers of class 3 include CD20, CD130, and CD166.

FIG. 32 shows an example of different adhesion molecule expression in the CD4$^+$CD62L$^-$CCR9$^-$β7$^+$ population in comparison to the CD4$^+$CD62L$^-$CCR9$^-$β7$^-$ population (FIG. 32 A to C). In this example, CD29 (β1 integrin) is almost absent in the CD4$^+$CD62L$^-$CCR9$^-$β7$^+$ population. It is thus anticipated that CD29 may be used as a marker of preferred condition Y–, with which to select for mucosal emigrant, immigrant and educated CD4$^+$ Treg cells. The table presented in FIG. 32 D summarises other migratory-type markers associated with the CD4$^+$CD62L$^-$CCR9$^-$β7$^+$ population. The markers positively correlated are of condition Y$^+$ and the markers negatively correlated are of condition Y$^-$. In the preferred aspect markers denoted Y$^+$ are used as a positive selection marker and markers denoted Y$^-$ are used as a negative selection marker for the purification of mucosal emigrant, immigrant and educated CD4$^+$ Treg cells. Each marker in this table is also assigned a class, where class 1 represents a strong association with the CD4$^+$CD62L$^-$ CCR9$^-$β7$^+$ population and high functional significance. Class 2 represents a strong association with the CD4$^+$ CD62L$^-$CCR9$^-$β7$^+$ population or high functional significance. Class 3 represents weak association and/or uncertain functional significance.

Any of these markers, Y, can be included in a CD4$^+$ Treg cell population according to the invention or used in a method of the invention to select the right signature pattern on the CD4$^+$ Treg cells. As shown in FIG. 32 markers of class 1 include CD29, CD38, CD49c, CD49e, CD102, and CD14. Markers of class 2 include CD15s, CD27, CD49b, CD84, CD119, CD161, CD184, and CD305. Markers of class 3 include CD71, CD126, CD134, CD151, CD171, CD196, CD227 and CD49f.

The aforementioned markers relate to tissue localisation, emigration, immigration and retention.

Analyses of cells with CD4$^+$CD25$^{hi}$CD127$^{lo}$α4$^+$β7$^+$ character revealed strong enrichment of surface markers that denote regulatory function, and a restriction of markers that generally denote pro-inflammatory functions within mucosal tissues.

FIG. 33 shows an example of a functional marker, CD39 (ENTPD1), which is a putative immunosuppressive element on the surface of T-cells, and which is enriched in the CD4$^+$CD25$^{hi}$CD127$^{lo}$α4$^+$β7$^+$ population. It is thus anticipated that CD39 may be used as a marker of preferred condition Z$^+$, with which to select for Treg cells within mucosal emigrant, immigrant and educated CD4$^+$ T-cell populations. The table presented in FIG. 33D summarises other functional-type markers associated with the CD4$^+$CD25$^{hi}$CD127$^{lo}$α4$^+$β7$^+$ population. The markers positively correlated are of condition Z+, and largely represent entities with putative immunosuppressive activities, where in the preferred aspect they are used as a positive selection marker for the purification of Treg cells from mucosal emigrant, immigrant and educated CD4$^+$ T-cell populations. The markers negatively correlated are of condition Z−, and largely represent entities with putative pro-inflammatory activities, where in the preferred aspect they are used as a negative selection marker for the purification of Treg cells from mucosal emigrant, immigrant and educated CD4$^+$ T-cell populations. Each marker in this table is also assigned a class, where class 1 represents a strong association with the CD4$^+$CD25$^{hi}$CD127$^{lo}$α4$^+$β7$^+$ population and high functional significance. Class 2 represents a strong association with the CD4$^+$CD25$^{hi}$CD127$^{lo}$α4$^+$β7$^+$ population or high functional significance. Class 3 represents weak association and/or uncertain functional significance.

Any of these markers, Z, can be included in a CD4$^+$ Treg cell population according to the invention or used in a method of the invention to select the right signature pattern on the CD4$^+$ Treg cells. As shown in FIG. 33 markers of class 1 include CD21, CD35, CD73, CD122, CLIP, and CD120b. Markers of class 2 include CD6, CD39, CD50, CD109, CD226, CD243, CD268, CD274 and CD210. Markers of class 3 include CD49c, CD53, CD84, CD95, and CD107a.

The CD4$^+$ Treg cell may thus have specific signatures that:
i) identify that the cells are regulatory T-cells, typically CD4$^+$CD25$^{hi}$CD127$^{lo}$
ii) identify that the regulatory T-cells are tissue type tropic, i.e. they can migrate to the diseased area (i.e. small bowel mucosa), typically α4β7$^+$ or α4$^+$β7$^+$
iii) optionally, identify that the Treg cells are diseased tissue tropic, i.e. they are so-called homing cells that can localize in the diseased tissue, typically CCR9$^+$, and
iv) identify that the regulatory T-cells are emigrant cells, i.e. they originate from the target tissue, i.e. the diseased tissue (antigen-experienced cells), typically CD62L$^-$CD38$^+$, and
v) optionally, identifying that the Treg cells are marked for mucosal retention, typically α4$^+$αE$^+$β7$^{high}$ or α4αE β7$^{high}$, and optionally one of more X signatures selected from
a) CD26, CD97, CD143, CD195, CD278,
b) CD61, CD63, CD146, CD183, CD197, CD200, CD244,
c) CD20, CD130, CD166,
and optionally one or more Y signatures selected from
d) CD29, CD38, CD49c, CD49e, CD102, CD14,
e) CD15s, CD27, CD49b, CD84, CD119, CD161, CD184, CD305,
f) CD71, CD126, CD134, CD151, CD171, CD196, CD227, CD49f,
and optionally one or more Z signatures selected from
g) CD21, CD35, CD73, CD122, CLIP, CD120b,
h) CD6, CD39, CD50, CD109, CD226, CD243, CD268, CD274, CD210,
j) CD49c, CD53, CD84, CD95, CD107a.

Any single Y-signature may be incorporated into the Treg identifier of aspect i) above, or multiple Y-signatures may be incorporated as such. Optionally, further Y-signature marker or markers, may be added to identified Treg subtypes within the target population.

Moreover, it is preferred that the CD4$^+$ Treg cells are not recent thymic emigrants or are immigrant cells to the lymph nodes from the peripheral circulation. Therefore, the CD4$^+$ Treg cells may have one or more of the following signatures:

h) CD62L$^+$—i.e. to exclude cells that gain access to lymph nodes via HEV (high endothelial venules),
j) CCR9$^+$CD45RA$^+$, CCR9$^+$CCR7$^+$, CCR9$^+$CD62L$^+$, and/or CCR9$^+$CD45RO$^-$ to exclude cells that are recent thymic emigrants, e.g. cells that are CCR9$^+$CD45RA$^+$ or CCR9$^+$CCR7$^+$ or CCR9$^+$CD62L$^+$. Any combination of these markers for the denoted +/− condition is considered relevant to the exclusion of recent thymic emigrant de novo T-cells, and for the parallel exclusion of resting central memory cells that have not been recently activated against antigen (i.e. should carry the CD45RA$^+$/CD45RO$^-$ character),
k) CCR9$^+$CCR7$^+$CD62L$^+$CD45RA$^+$CD45RO$^-$ to exclude all h) and j) above.

Herein is given a number of examples of possible combinations of signatures that are within the scope of the present invention. This text does not exclude any possible combination of signatures that can be derived from the specification and appended claims.

Terminology of Immunology Cell Marker Identification

Through the use of flow cytometry it is possible not only to detect the presence or absence of a protein on a cell surface, but also accurately quantify how much of a protein is on the cell surface. Some plasma membrane markers are either expressed or not on a particular cell, while others have expression that can be quite graded across various cell types. For example, CD4 is either expressed or not, so cells are annotated simply as CD4$^-$ or CD4$^+$, respectively. On the other hand, a graded expression of the CD25 protein is common, so CD25 expression is sometimes noted as CD25$^{lo}$, CD25$^{int}$, CD25$^{hi}$(or CD25$^{high}$), for low, intermediate or high expression, respectively. It should be noted that measurement of fluorescence intensity in flow cytometric applications is generally visualised in a log scale. In addition, multi-fluorochrome analyses generally require computational compensation of data to correct for spectral overlap of the different fluorochromes. Therefore, depending on the content and style of analysis, marker resolution can be differently represented, even when the same antibody/fluorochrome reagent is used for analysis of the marker in question. In practical terms, this means that the resolution of X$^{hi}$ from X$^{int}$ populations is not always achievable, especially in more complex multivariable analyses. In such instances, it is common to refer to the X$^{+/-}$ annotations, where the X$^+$ condition is inclusive of known X$^{int}$ and X$^{hi}$ populations. Thus X$^+$ may be used in the analytical or physical definition of X$^{hi}$, for example, so long as X$^{int}$/X$^{hi}$ differentiator is not representative of a critical and otherwise unqualified descriptor of population identity.

Tregs and Treg Subtypes

T-cells or T-lymphocytes belong to a group of white blood cells known as lymphocytes and play a central role in cell-mediated immunity. They can be distinguished from other lymphocyte types, such as B cells, by the presence of a specific receptor on their cell surface, the so-called T-cell receptors (TCR). T-cells represent a massively diverse set of small cells that embody the modulatory workhorse of the immune system.

Several different subsets of T-cells have been discovered, each with a distinct function T helper cells (T$_H$ cells) including effector T-cells (Teff) and regulatory T cells (Treg); memory T-cells (T$_M$ cells), natural killer T-cells (NKT cells) etc.

Effector T-cells are responsible for promoting "pro-inflammatory" responses, while regulatory T-cells are their antithesis in promoting "anti-inflammatory" responses. Thus the outcome of any specific immune response of switching inflammation on and off can be considered as a balance between Teff and Treg activities.

T-cells can express one of either CD4 or CD8 receptors (CD denotes cluster of differentiation). These closely related receptors are components of TCR, and responsible for the specific docking to MHC complexes. MHC is a complex of multiple proteins expressed on the surface of cells, and can be divided into two types. MHC class I (MHC I) is expressed on all cell types, while MHC class II (MHC II) is largely related to dendritic cells (DC) and antigen-presenting cells (APC). These protein complexes are those responsible for presenting antigens to cells of the adaptive immune system, specifically to T-cells. MHC I is responsible for presenting antigens of that are obtained from within the cell ("self" antigens), whereas MHC II is responsible for representing antigens that are obtained from outside the cell ("non-self" antigens). CD4 is responsible for docking to MCH II, while CD8 is responsible for docking to MHC I. Thus, CD4 will recognize antigens derived from outside the cell, whereas CD8 will recognize those from within the cell.

Tregs can be divided into two major subgroups. Tregs that express the protein FOXP3 (FOXP3$^+$ Tregs), and those that do not (FOXP3$^-$ Tregs). In fact, FOXP3$^+$ Tregs are now appreciated to be the major player in immunosuppressive function in most tissues of the body. Tr1 Tregs are identified functionally by their ability to secrete IL10. Another common type of FOXP3$^-$ Treg is the Tr3. This is similarly defined by its ability to secrete a protein called TGFβ. The conceptions of these FOXP3$^-$ Tregs were based on early experimental mouse studies dealing with immunosuppressive function. In human immunology it is currently unclear how much of a role these cells play in overall immunosuppression, or what their precise role might be. In general, it is assumed that FOXP3$^-$ cell immunosuppressive function is "contact-independent", while FOXP3$^+$ immunosuppresive function is "contact-dependent". This means that FOXP3$^-$ cells secrete factors that are free to diffuse in the general cellular milieu to affect general immunosuppression, while FOXP3$^+$ cells need to physically cross-present inhibitory molecules on their plasma membrane to the cells they are targeting for suppression, thus requiring physical contact.

In the present context, the major focus is on FOXP3$^+$ cells, however, this presents an additional challenge. That is, unlike many marker proteins, which are presented on the cell plasma membrane, FOXP3 is actually expressed in the nucleus. Therefore, to detect FOXP3 it is necessary to destroy the cell. So despite being the defining marker of FOXP3$^+$ Tregs, it is not possible to purify living cells on the basis of its expression.

FOXP3$^+$ cells are subdivided into "natural Tregs" (nTregs) and "induced Tregs" (iTregs). nTregs arise naturally in the thymus, and are selected on the basis of being able to react with "self" antigens. This means that they are the general mediators of so called "self-tolerance". That is, they stop the immune system from attacking the body's own tissues. On the other hand, iTregs are those cells selected from nave T-cells in peripheral tissues for antigens from both self and extrinsic factors. Therefore, iTregs can be considered to mediate "adaptive tolerance", or tolerance towards mainly non-harmful things like antigens from our food, or commensal bacteria in our intestines. This concept of local clonal selection is something that can be referred to as antigen "education", and involves many co-stimuli.

FOXP3$^+$ Treg Identification by Proxy Markers

As mentioned above, the FOXP3 marker cannot be directly detected and used to the identification of live Tregs, since its detection is destructive. This issue has been solved and relies on one of two similar correlations of alternate plasma membrane markers. The simplest way to identify a FOXP3$^+$ Treg is by positivity of CD4 and high expression of CD25, i.e. CD4$^+$CD25$^{hi}$. A more rigorous identification can be conducted by further quantification of low CD127 expression: CD4$^+$CD25$^{hi}$CD127$^{lo}$. As Teff cells by definition possess CD127$^{hi}$ expression, CD4$^+$CD25$^{hi}$CD127$^{lo}$ effectively exclude Teff from identification and purification.

T-Cell Migration

Integrin proteins are proteins that generally form dimeric complexes on the cell surface of two different integrin forms. These dimeric forms represent an adhesive unit that adheres to specific receptors presented on the walls of blood vessels and other structures. This means, cells that express a specific integrin pair can bind to a specific receptor, which itself can be expressed on the blood vessels in a specific tissue. In effect, the expression of specific integrin pairs on a cell can essentially barcode a cell to stick to the blood vessel walls of a specific tissue. The integrin pair responsible for sticking cells to the blood vessels of mucosal tissue is the α4β7-integrin dimer, for example.

However, to transmigrate across the cell wall into a target tissue, the cell needs to also receive a second signal, effectively serving as a further refinement of exactly what part of the selected tissue the cell should access by matching activators produced by specific tissue compartments to cognate receptors expressed by specific cells. In the case of the small bowel mucosa a small protein called CCL25, which is a "chemokine", is produced. This can trigger cells to transmigrate into the small bowel by binding to the CCR9 receptor on migrating cell surfaces. CCL25 binding to the CCR9 receptor induces the active state of the α4β7-integrin dimer, allowing tight binding and endothelial transmigration. In this example a cell must possess both α4β7-integrin and CCR9 on their cell surface to move into the small bowel mucosa.

There exist other distinct types of adhesion molecules and chemoattractants involved in directed cell migration, than the integrin and chemokine examples above.

Local Mucosa-Educated CD4 Treg Signature in Mesenteric Lymph Nodes (MLN)

This set of signatures specifically pertains to identifying Treg subtypes in "mesenteric lymph nodes" (MLN) of CD patients. Draining mesenteric lymph nodes may be described as the lymph node(s) that is draining the inflammatory lesion, and thus contain high numbers of immune cells that have encountered disease antigens. These draining MLN are recovered from a patient undergoing surgical treatment for CD due to bowel stricture or deep infections associated with diseased bowel. We have found that MLN are extremely rich sources of Treg cells for potential adoptive immunotherapy approaches.

The important first step in the MLN procedure is the exclusion of Tregs that have entered the MLN from routes other than the inflamed tissue. Positivity for the marker CD62L denotes non-mucosal entry of T-cells to lymph nodes via high endothelial venules. Thus CD4$^+$CD25$^{hi}$CD127$^{lo}$CD62L$^-$ identification is a crude enrichment procedure.

CD38 expression is up-regulated on T-cells that have interacted with APC in the mucosa or in the lymph nodes of the small and large bowel. Thus, the CD4$^+$CD25$^{hi}$CD127$^{lo}$CD62L$^-$CD38$^+$ signature will denote Tregs that are largely educated locally.

However, there are further considerations to the CD38+ phenotype, which makes it necessary to develop further refinement of the local education signature to support highly accurate cell identification.

Mucosal-Educated Peripheral Blood CD4 Treg Signature

The approach outlined above pertains to the treatment of patients with acute manifestations of CD that have been identified for surgical intervention. This treatment involved the resection of the segment of inflamed small or large bowel. In this process, the MLN draining the lesion are included in the resection. While these lymph nodes are extremely enlarged and are a highly rich source of specific Treg precursors, there is the obvious limitation to large-scale application of this treatment in the sense that an invasive surgical procedure is required for recovery of the MLN cells. Presented data suggest that it is possible to use various cell signatures related to those outlined above to identify cells in the patient blood stream that have recently come from the diseased tissue. It is thus possible to purify these cells as starting material for adoptive immunotherapy protocols.

There are several combinations of cell signatures that are candidates for this type of peripheral blood approach, the first of which is the simple mucosal-educated Treg signature. The first and most simple option for such an approach is use of the $CD4^+CD25^{hi}CD127^{lo}CD62L^-CD38^+\alpha4^+\beta7^{int}$ signature described for the MLN approach above. This means we can effectively purify cells that have gone through the antigen education, homing receptor patterning, and export from mesenteric lymph nodes and entered peripheral circulation. While difficult to test in humans, we predict that the stability of CD38 expression is low, and thus CD4+ Tregs carrying CD38 in peripheral blood are likely to be those that have recently emigrated from bowel mucosa.

Data presented herein suggest that CD patients display diminished CCR9 expression on recent mucosal emigrant CD4+ Treg populations. This is in line with findings inside the MLN. Therefore, the signature itself is identical to the MLN approach:
$CD4^+CD25^{hi}CD127^{lo}CD62L^-CD38^+\alpha4^+\beta7^+CCR9^+$ While this population can be recovered from a non-invasive blood draw rather than a major surgical operation, the overall frequency of $CD4^+CD25^{hi}CD127^{lo}CD62L^-CD38^+\alpha4^+\beta7^+CCR9^+$ cells is lower. While the MLN draining the inflamed bowel are clearly major inductive centres, all other lymph nodes will contain disease-involved antigen-specific Tregs as a function of the migratory recirculation of Tregs. Based on several other observations the present inventors have made in CD patient blood, it is predicted that the proportion of disease-involved antigen-specific Tregs inside this small subpopulation of peripheral blood will be relatively high.

Despite the low frequency of these target cells in peripheral blood, it was possible to purify them with high accuracy from blood using FACS methods. Indeed, the strength of this approach is that it does not rely on laborious functional cloning for cell identification, but direct identification by surface markers. Based on our experience it is possible to recover approximately 2000 viable cells per 10 mL of whole blood. Therefore, it may ultimately be possible to treat patients with a single blood draw no bigger than a regular blood test volume taken at their physicians office.

Mucosal Educated and Mucosa-Retention CD4 Treg Signature

There is potential for use of another Treg signature in peripheral blood specimens. The signature is:
$CD4^+CD25^{hi}CD127^{lo}CD62L^-CD38^+\alpha4^+\beta7^{hi}\alpha E^+CCR9^+$ The difference of this signature is the presence of the second integrin receptor, $\alpha E\beta 7$. This receptor is responsible for signalling cells to be retained in the mucosa. Thus these cells for some reason have been triggered to circulate from the MLN to the mucosal tissue, and then reside there, rather than continuing transit to the MLN again. Though unclear at this stage, this may represent a particularly important sub-population of T-cells that mediates the inflammatory state of the mucosa directly. The challenge comes from the frequency of these cells in peripheral circulation, which we observe to be lower than 0.0001% in most patients. However, what is intriguing is that this population of cells in the peripheral blood of CD patients we have found to be almost entirely defective in CCR9 expression. This suggests that these cells, despite their low frequency, could be key mediators of CD immunopathology.

Mucosal Educated and Mucosal-Tropic CD4 Peripheral Blood Treg Signature Tropism refers to the ability of a cell to be directed towards specific stimuli. Clearly mucosal-tropism refers to the ability of T-cells to move to the mucosa. While it is clear that cells of the signatures described in the previous three sections all possess the mucosal-tropic capacity, a separate Treg signature can be used to identify cells that possess that capacity for small bowel tropism, but are unlikely to have recently emigrated from the small bowel. The signature simply selects cells that are negative for CD38, making the signature:
$CD4^+CD25^{hi}CD127^{lo}CD62L^-CD38^-\alpha4^+\beta7^+$ The frequency of these cells in the peripheral circulation is somewhat higher than those of CD38+ cells in this background. A major reason for trialling these cells would be to assess one potentially powerful technique in Treg immunotherapy diseases of the gastrointestinal tract. That is, while the emigrant $CD38^+CD62L^-$ population is likely to contain a very high proportion of iTregs, the $CD38^+CD62L^+$ population is likely to contain a high proportion of nTreg cells. In mouse experiments, it was shown that iTregs and nTregs actually displayed a synergism in supressing inflammatory states. More recently it has become apparent that there is indeed very little overlap in the iTreg and nTreg TCR sequence repertoire. Indeed self-reactive nTregs provide a blanket immunosuppression within the mucosal tissues, and iTregs supplement this background in an adaptive manner.

In the paragraphs above unique cell signatures have been identified for targeting different Treg cell classes for purification and application of immunotherapy protocols. Clearly this identification and purification represents the first of several key steps in successful cellular immunotherapy application.

However, in some cases the cell populations identified may be deficient in the expression of CCR9, required for correct small bowel mucosa tropism. Moreover, when the cells are expanded in vitro, they typically loose CCR9 expression in the absence of appropriate stimuli. Thus, when infused them back to the patient, there will be more cells in circulation with the same apparently critical homing defect. However, as discussed below the homing pattern defect may be corrected after the cell growth phase, addressing this challenge in any Treg immunotherapy approach for CD in the small bowel.

While the signatures outlined incorporate the minimal signatures with which to identify the desired Treg populations, there are several more standard markers that could be built into these core signature marker panels to restrict cells to more specific subtypes.

Therapeutic Use—Immunotherapy

Immunotherapy is broadly used to describe any clinical treatment that aims to modulate immune function. With respect to cellular immunotherapy, the two major fields of cellular immunotherapy focus on cell-based vaccine (mainly DC) immunotherapy and T-cell immunotherapy. In traditional vaccination, antigen preparations are injected directly to the subject to raise immune responses against antigens specific for disease pathogen. DC immunotherapy is thought to be more effective as antigens are pre-loaded onto DC cells, and they can more effectively enhance antigen cross-presentation to T-cells and B-cells in vivo. T-cell immunotherapies can be divided into immunostimulatory and immunosuppressive classes. Adoptive transfer of $CD4^+$ T-effector cells, or cytotoxic CD8 T-cells in the case of cancer, is seen as immunostimulatory in provoking immune responses against tumours. Treg immunotherapies by contrast aim to provide immunosuppressive capacity in treatment of inflammatory and autoimmune conditions.

The markers identified in the case study described herein may be used to define Treg populations that may be harvested from patient blood, purified ex vivo, expanded, re-patterned, if necessary, and then infused back to the patient. The method of autologous Treg adoptive immunotherapy is thus defined at the level of cell identification by the presented markers, as a means of purification by flow cytometric (or affinity) approaches.

The Tregs as identified herein can be used in the treatment of IBD including Crohn's disease and ulcerative colitis as well as other inflammatory diseases of the small and large bowel such as indeterminate colitis, pseudomembranous colitis, microcytic colitis (including lymphocytic colitis and collagenous colitis), bowel symptoms in systemic lupus erythematous (SLE), bowel symptoms in systemic sclerosis, primary (progressive) sclerosing cholangitis and bowel-associate graft-versus-host disease manifestations in organ, tissue and haematological transplantation.

The Tregs as identified herein can be used in the treatment of IBD, i.e. ulcerative colitis and Crohn's disease.

Aspects relating to treatment of Crohn's disease affecting the small bowel are described herein. However, as explained herein before CD may affect the whole gastrointestinal tract and, accordingly, the aspects of the invention may be broadened to treatment of CD affecting other parts of the gastrointestinal tract. Furthermore, inflammatory diseases (also outside the gastrointestinal tract) may be treated with Tregulatory cells using the same approach. As mentioned above the signatures are expected to be of similar nature. Elements of marker signatures relating to small bowel tropism and emigration, which in case e.g. of CD of the colon or perianal area should be changed to colon tropism and anal canal tropism etc, when targeting disease in these areas. That is to say, when treating other inflammatory diseases, the identity of Treg cells may be similar whereas the homing functions will be related to the tissue type and location of inflammation. However, it may be anticipated that functional makers of Tregs of a specific tissue type or anatomical location may be particular to this tissue type or location, in as much that functional makers may serve to further define Treg origin is that of the tissue of interest.

As described above, signatures of a $CD4^+$ Treg cell population suitable for use in cellular immunotherapy of CD are identified and, accordingly, a starting material can be obtained e.g. from the subject suffering from the inflammatory or autoimmune disease of the gastrointestinal tract.

Such starting material can be obtained by the following method comprising i) subjecting peripheral blood from a patient suffering from an inflammatory or an autoimmune disease of the gastrointestinal tract to single-cell analysis, to obtain $CD4^+$ Treg cells having the selection of signatures described herein.

The method includes means to sort $CD4^+$ Treg cells that are emigrant/immigrant populations from/to the diseased tissue and that they can localise in the diseased tissue.

The $CD4^+$ Treg cells may also contain the signatures $CD38^+$, $CD69^+$ and/or $CD44^+$ to denote recent activation.

The method typically applies analytical filters to
i) exclude cells that gain access to lymph nodes via HEV, and
ii) exclude cells that are recent thymic emigrants.

The cells that gain access to lymph nodes via HEV may be $CD62L^+$ cells; and recent thymic emigrants may be $CCR9^+CD45RA^+$, $CCR9^+CCR7^+$, $CCR9^+CD62L^+$, or $CCR9^+CD45RO^-$ cells.

Thus, in the $CD4^+$ Treg cells to be excluded are $CCR9^+CCR7^+CD62L^+CD45RA^+CD45RO^-$ cells.

The invention also relates to a method for obtaining Treg cells as defined herein, the method comprising essentially the steps described above, but Treg cells are provided lacking one or more signatures, notably X, Y, Z, $\alpha 4\beta 7^+$ or $\alpha 4^+\beta 7^+CCR9^+$ or $\alpha 4^+\beta 7^+$, where X and Y are the signatures indicating that the Treg can localize, has emigrated from, or is marked for preferential retention in the specific part of the gastrointestinal tract that is diseased. X may be $X^+$ or $X^-$, Y may be $Y^+$ or $Y^-$. Z is a functional marker and may be $Z^+$ or $Z^-$. One or more of X, Y and/or Z may be present.

The signature(s) may be introduced or re-introduced to the Treg cell by stimulation of cells with a combination of ATRA, TGFbeta and IL10. In the case that the repatterning relates to the signature $\alpha 4^+\beta 7^+$, $\alpha 4^+\beta 7^+CCR9^+$, $\alpha 4^+\beta 7^+X$, $\alpha 4^+\beta 7^+X$ $CCR9^+$, $\alpha 4^+\beta 7^+Y$, $\alpha 4^+\beta 7^+Y$ $CCR9^+$, $\alpha 4^+\beta 7^+XY$ and $\alpha 4^+\beta 7^+XY$ $CCR9^+$ the repatterning stimulation is the same as mentioned above, but includes additional rapamycin supplementation.

Thus, Treg cells may be provided as described herein before.

The Treg cells obtained may then be expanded (cultured) and, optionally re-patterned as described herein. The thus obtained/expanded/re-patterned $CD4^+$ Treg cells may then be administered to the patient suffering from the inflammatory or autoimmune disease of the gastrointestinal tract.

In a separate aspect, the invention relates to a composition for cellular immunotherapy, the composition comprising a $CD4^+$ Treg cell population identified and/or obtainable as described herein.

Treg cells may be dispersed in a suitable medium before administration to the patient. A suitable medium may be an aqueous medium e.g. containing substances that ensures viability of the cells. It may also contain osmotically active substances, pH regulating substances or other physiologically acceptable substances. To this end, the present invention also relates to a pharmaceutical composition comprising the Treg cells specified herein together with an aqueous medium. The pH and osmotic pressure of the composition are adjusted to physiologically acceptable values, i.e. pH in a range of from 3 to 8 including 7.4, and the osmotic pressure in a range of from 250-350 mOsm/l including 285-300 mOsm/l. A specific example of a suitable medium is a 0.9% w/w sodium chloride solution comprising up to 3% w/w human serum albumin such as up to 2% w/w serum albumin or up to 1% w/w serum albumin. Another suitable medium is an aqueous medium comprising albumin such as 2% w/w albumin. They may also be suspended in saline-based solutions of physiological pH, and with appropriate biological and non-biological additive to promote cell survival and stability.

The Treg cells may also be admixed with a blood sample preferably from the patient's own blood or at least from blood compatible with the patient's own blood.

The Treg cells are normally administered parenterally to the patient such as intraveneous, intraarterial, intrathecal or intraperitoneal administration.

The number of cells to be administered depends on the disease and the severity of the disease to be treated, as well as the weight and age of the patient. It is contemplated that the number of cells is in a range of from $1 \times 10^5$ to about $10 \times 10^9$.

The Treg cells are administered by the parenteral route, preferably via injection into the circulatory system.

Aspects relating to treatment of Crohn's disease affecting the small bowel are described herein. However, as explained herein before CD may affect the whole gastrointestinal tract and, accordingly, the aspects of the invention may be broadened to treatment of CD affecting other parts of the gastrointestinal tract. As mentioned above the signatures are expected to be essentially the same apart from the signature relating to small bowel tropism, which in case e.g. of CD of the colon or anal canal (perianal area) should be changed to colon or anal canal tropism etc.

The invention also relates to a method for treating a patient suffering from an inflammatory disease of the gastrointestinal tract, the method comprises a) obtaining $CD4^+$ Treg cells defined herein from a tissue sample obtained from a patient suffering from an inflammatory disease in the gastrointestinal tract,
b) expanding the Treg cells in vitro,
c) optionally re-patterning the expanded Treg cells to obtain Tregs that have signatures ii) and iv) and optionally iii) and/or v); or the T-cells have the signatures ii), iv) and v) and optionally iii), or the T-cells have the signatures ii), iv) and v) and optionally iii), wherein the signatures is for
    ii) identifying that the Treg cells are tissue type tropic, i.e. they can migrate to mucosal tissue,
    iii) optionally, identifying that the Treg cells are diseased tissue tropic, i.e. homing cells that can localize in the diseased tissue region,
    iv) identifying that the Treg cells are emigrant cells, i.e. they originate from the target tissue, and
    v) optionally, identifying that the Treg cells are retained in the target tissue,
d) administering the Treg cells obtained from b) or c) to the patient.

In a specific aspect, the invention relates to a method for treating a patient suffering from Crohn's disease affecting small bowel, the method comprises
a) isolating Treg cells defined herein from a tissue sample obtained from a patient suffering from an inflammatory disease such as, e.g., Crohn's disease,
b) expanding the Treg cells in vitro,
c) optionally re-patterning the expanded Treg cells to obtain Tregs that have signatures for
    ii) identifying that the Treg cells are tissue type tropic, in this case mucosal tropic, i.e. they can migrate to mucosal tissue,
    iii) optionally, identifying that the Treg cells are diseased tissue tropic, i.e. homing cells that can localize in the diseased tissue of the small bowel,
    iv) identifying that the Treg cells are emigrant cells, i.e. they originate from the target tissue of the gastrointestinal tract, and
    v) optionally, identifying that the Treg cells are retained in the target tissue of the gastrointestinal tract,
d) administering the Treg cells obtained from b) or c) to the patient.

The expanded and optionally repatterned Treg cells from step b) or c) should have features as defined herein.

As explained herein before the method of the invention is not limited to treatment of a patient suffering from Crohn's disease in the small bowel or suffering from an inflammation of the small bowel, but the method is also applicable to treatment of a patient suffering from Crohn's disease in other parts of the gastrointestinal tract. In such case the above-mentioned method must be adjusted in such a manner that Tregs are obtained that are suitable for use in the treatment of Crohn's disease in the diseased part of the gastrointestinal tract, see e.g. under the description of Tregs.

The Tregs are suitably obtained from a tissue sample from a patient. The sample may be from a lymph node such as a mesenteric lymph node draining inflamed bowel, or it may be from bowel mucosa, from lamina propria or it may be from a blood sample. Most conveniently, the sample is a peripheral blood sample.

The present invention also relates to a method for obtaining Treg cells as defined herein, the method comprises
a) obtaining Treg cells defined herein from a tissue sample obtained from a patient suffering from an inflammatory disease in the gastrointestinal tract,
b) expanding the Treg cells in vitro,
c) optionally re-patterning the expanded Treg cells to obtain Tregs that have signatures, ii) and iv) and optionally iii) and/or v); or the T-cells have the signatures ii), iv) and v) and optionally iii), or the T-cells have the signatures ii), iv) and v) and optionally iii), wherein the signatures is for
    ii) identifying that the Treg cells are tissue type tropic, i.e. they can migrate to mucosal tissue,
    iii) optionally, identifying that the Treg cells are diseased tissue tropic, i.e. homing cells that can localize in the diseased tissue region,
    iv) identifying that the Treg cells are emigrant cells, i.e. they originate from the target tissue, and
    v) optionally, identifying that the Treg cells are retained in the target tissue.

The expanded and optionally repatterned Treg cells from step b) or c) should have features as defined herein.

Sorting of T-Cells

The isolation of cells as referred to in step a) refers to first the recovery of mononuclear cells from patient tissue specimens, and labelling said pool of mononuclear cells with antibodies specific for appropriate markers. The cells can be retrieved from mucosa through microdissection of lamina propria and preparation of the tissue e.g. using enzyme collagenase and other substances. The cells may also be prepared from lymph nodes starting with microdissective trimming of the tissue followed by careful mechanical degradation before using collagenase and substances mentioned above. The cells may also be prepared from peripheral blood.

Typically, the desired $CD4^+$ Treg cells are sorted from the peripheral blood using antibodies against the desired signatures.

Accordingly, in an aspect of the invention, the invention relates to a kit of antibodies, wherein the kit contains antibodies against one or more of the following:
i) $CD4^+$, $CD25^{hi}$ and/or $CD127^{lo}$
ii) $\beta7^+$ and/or $\alpha4^+$
iii) optionally, $CCR9^+$
iv) $CD62L^-$ and/or $CD38^+$ v) optionally, $\alpha 4^+\alpha E^+\beta 7^{hi}$ and optionally one of more antibodies against one or more X signatures selected from
a) CD26, CD97, CD143, CD195, CD278,
b) CD61, CD63, CD146, CD183, CD197, CD200, CD244,
c) CD20, CD130, CD166,
and optionally one or more antibodies against one or more Y signatures selected from
d) CD29, CD38, CD49c, CD49e, CD102, CD14,
e) CD15s, CD27, CD49b, CD84, CD119, CD161, CD184, CD305,
f) CD71, CD126, CD134, CD151, CD171, CD196, CD227, CD49f,
and optionally one or more antibodies against one or more Z signatures selected from
g) CD21, CD35, CD73, CD122, CLIP, CD120b,
h) CD6, CD39, CD50, CD109, CD226, CD243, CD268, CD274, CD210,
j) CD49c, CD53, CD84, CD95, CD107a.

The kit may also contain antibodies against CD38, CD69, CD44, CD62L, CD45RA, CCR7, or CD45RO.

Once labelled, cells are purified by immunoaffinity and/or flow cytometric sorting techniques to yield highly enriched or purified Treg populations of desired characteristics. In vitro expansion of isolated Treg populations as referred to in step b) is achieved by way of recombinant T-cell stimulation in the form of anti-CD3/anti-CD28 activating antibodies in combination with IL2, or alternatively the outgrowth of Treg populations on transgenic feeder cell populations, or irradiated autologous/allogeneic APCs with IL2 supplementation. Repatterning of the correct homing receptor expression post-expansion as referred to in c) entails the recombinant reactivation of expanded T-cell populations with anti-CD3/anti-CD28 activating antibodies and subsequent introduction of stimuli in precise combination Stimuli include all-trans retinoic acid, Interleukin-10 and transforming growth factor-beta.

In the case where the Treg cells lack the signature $\alpha 4^+\beta 7^+CCR9^+$, the signature may be introduced or re-introduced to the Treg cell by stimulation of cells with a combination of ATRA, TGFbeta and IL10. In the case that the repatterning relates to the signature $\alpha 4^+\beta 7^+X/Y/Z$, the repatterning stimulation is the same as mentioned above, but includes additional rapamycin supplementation.

In case, the Treg cells lack the signature $\alpha 4^+\beta 7^+$, which can be introduced or re-introduced to the Treg cell by stimulation of cells with a combination of ATRA, TGFbeta and IL10.

Identification, Purification and Expansion of Tregs

The Tregs are identified and purified as described herein. Thus, the identification and purification typically involve the use of specific antibodies and techniques well known to a person skilled in the art.

One set of methods central to manipulating cells from the human body are those that identify a given cell type, and allow their purification as viable cells. In the following is described the key principals of cell identification and purification by direct and indirect means. There are many additional parameters by which cells can be identified, but are destructive in nature, so bare no use in purification and cloning of living cells.

Direct Antibody Detection of Plasma Membrane Markers by Flow Cytometry

The most important method in cellular immunology is the specific detection of surface proteins by way of specific antibodies. Considering cells of different types inevitably express different proteins on their cells surface, identifying specific protein signatures on their surface is the simplest direct means of identifying a given cell type. For instance, CD4 and CD8 form the basis of identifying T-cells in most applications.

Antibodies can be created in controlled conditions against specific proteins, or peptide fragments of proteins. This is simply achieved by injecting a laboratory animal, usually a mouse or rabbit, with a quantity of protein or peptide antigen. In biochemical applications it is often sufficient to use a preparation of the animal's blood to recover large amounts of antibodies, and are termed polyclonal antibodies, since multiple different antibody clones populate these preparations. In contrast, monoclonal antibody production utilizes cloning and characterisation of B-cells from the antigen-challenged animals. The basis for cellular and molecular cloning of antibodies will be discussed further in later sections, but for now we can see that specific single antibodies can be generated for any protein.

It is simply not enough to bind specific antibodies to a cell surface; there must also be a means of detecting each individual antibody. This is most commonly achieved by labelling each antibody with a specific fluorescent dye. Fluorescence simply describes the spectral properties of a molecule that can be excited with light of a specific colour, and will then emit light of a different colour. By labelling each antibody with a different colour, many different antibodies can be used to bind specific proteins on a cell surface, and each be quantitatively detected by the amount of fluorescent signal of each colour emitted by the cell when appropriately excited.

Excitation of different fluorescent dyes in the platforms that we will discuss is achieved by means of different coloured lasers. That is to say lasers emitting light of differing wavelengths. The instrument that often is used to detect multi-parameter fluorescence of cells is called a "flow cytometer". These instruments take cells suspended in solution and flow them, one-by-one, past an array of lasers and photodetectors. We are thus able to measure extremely accurately and rapidly the expression of specific proteins on the surface of individual cells. This technique forms the basis of the vast majority of cellular immunology analysis in both experimental and clinical settings Direct Cell Purification by FACS The use of flow cytometry to purify cells is called fluorescence-activated cell sorting (FACS). FACS instruments represent the same basic principle as analytical flow cytometers, though after the detection of cell fluorescence are able to physically sort cells. FACS instruments can sort cells in two basic manners. First, cells can be identified and sorted into up to four separate pools of cells. Second, single cells can be identified and deposited into single tubes. The single cell deposition is a powerful means of cell identity-based cloning, where individual cells represent clones that may be propa-gated, characterised and manipulated. A traditional method of single cell cloning is by 'limiting dilution'. This means you have a starting pool of cells, and you dilute these cells so there is on average less than one cell per given volume. The volume of cell suspension is then aliquoted such that you achieve single-cell distribution.

Direct Cell Purification by MACS Magnetic-activated cells sorting (MACS) technology is another method that can be used. The premise is basically that instead of a fluorescent label, specific antibodies are linked to magnetised microbeads. This in effect means that one is able to effectively magnetise specific cells based antibody binding. The largest drawback of this approach is the obvious limitation to the number of antibodies one can use, since a single antibody bound to a cell surface will magnetise the cell. It is most common to purify cells by a process of negative selection, that is, to magnetise all of the cells that you do not want to purify, and deplete these from your sample. The sophistication of the cell identities that can be purified is relatively low compared to FACS, and inevitably of much lower purity.

Treg Receptor Re-Patterning

It has been observed that the Tregs after manipulation may be devoid of one or more of the signatures. Especially, it has been observed that the MACS-enriched Treg cultures after expansion were almost devoid of small-bowel tropic homing receptor. Therefore, we developed a method to establish the signatures of the Tregs after having been expanded. The method involves a combination of low dose all-trans retinoic acid, TGF and IL10 to reintroduce the signatures $\alpha 4^+\beta 7^+CCR9^+$, for example.

LEGENDS TO FIGURES

FIG. 1. $CD4^+FOXP3^+$ $T_{regs}$ isolated from human intestinal LP carry higher levels of CCR9 than $CD4^+FOXP3^-$ $T_{eff}$ counterparts. (A) Single cell suspensions were prepared from LP dissected from histologically normal small and large bowel, resected from a representative CD patient with ileoceacal disease. Cells were stained for CD4, FOXP3, β7 and CCR9, then analysed by flow cytometry. Lymphocytes were gated for $CD4^+$, expressed as CD4vsFOXP3 dotplots (left hand panels), and Tregs defined as $CD4^+FOXP3^+$ with $CD4^+FOXP3^-$ defined as effector T-cells. Overlaid histograms of $CD4^+FOXP3^+$ and $CD4^+FOXP3^-$ populations are presented for CCR9 and β7 signal intensities relative to singly unstained controls. (middle panels) and for CCR9 intensity in the $CD4^+\beta 7^{hi}FOXP3^+$ in addition to $CD4^+\beta 7^{hi}FOXP3^-$ populations (right hand panels). Histogram gates in (A) were used to quantify percentage of positive cells (n=3), presented in (B).

Figure 2:
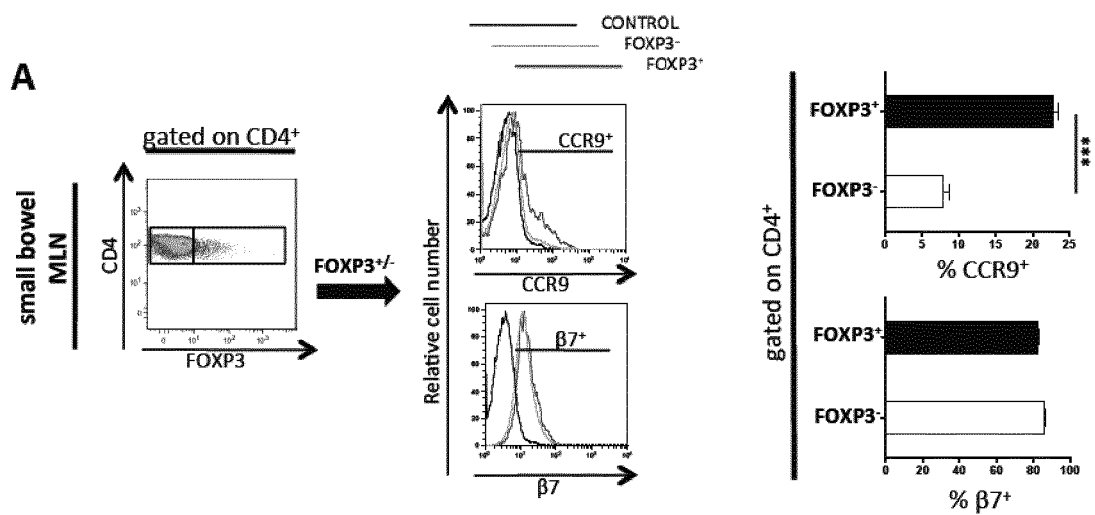

FIG. 2. $CD4^+FOXP3^+$ Tregs isolated from human MLN draining small bowel carry higher levels of CCR9 than $CD4^+FOXP3^-$ $T_{eff}$ counterparts. (A) Single cell suspensions were prepared from MLNs draining the small bowel, resected from a CD patient with ileoceacal disease. Cells were stained for CD4, FOXP3, β7 and CCR9, then analysed by flow cytometry. Lymphocytes were gated for $CD4^+$, expressed as CD4vsFOXP3 dotplots (left hand panel), and Tregs defined as $CD4^+FOXP3^+$ with $CD4^+FOXP3^-$ defined as effector T-cells. Overlaid histograms of $CD4^+FOXP3^+$ and $CD4^+FOXP3^-$ populations are presented for CCR9 and β7 signal intensities relative to singly unstained controls (right hand panels). Histogram gates in (A) were used to quantify percentage of positive cells (n=3), presented in (B).

Figure 3:
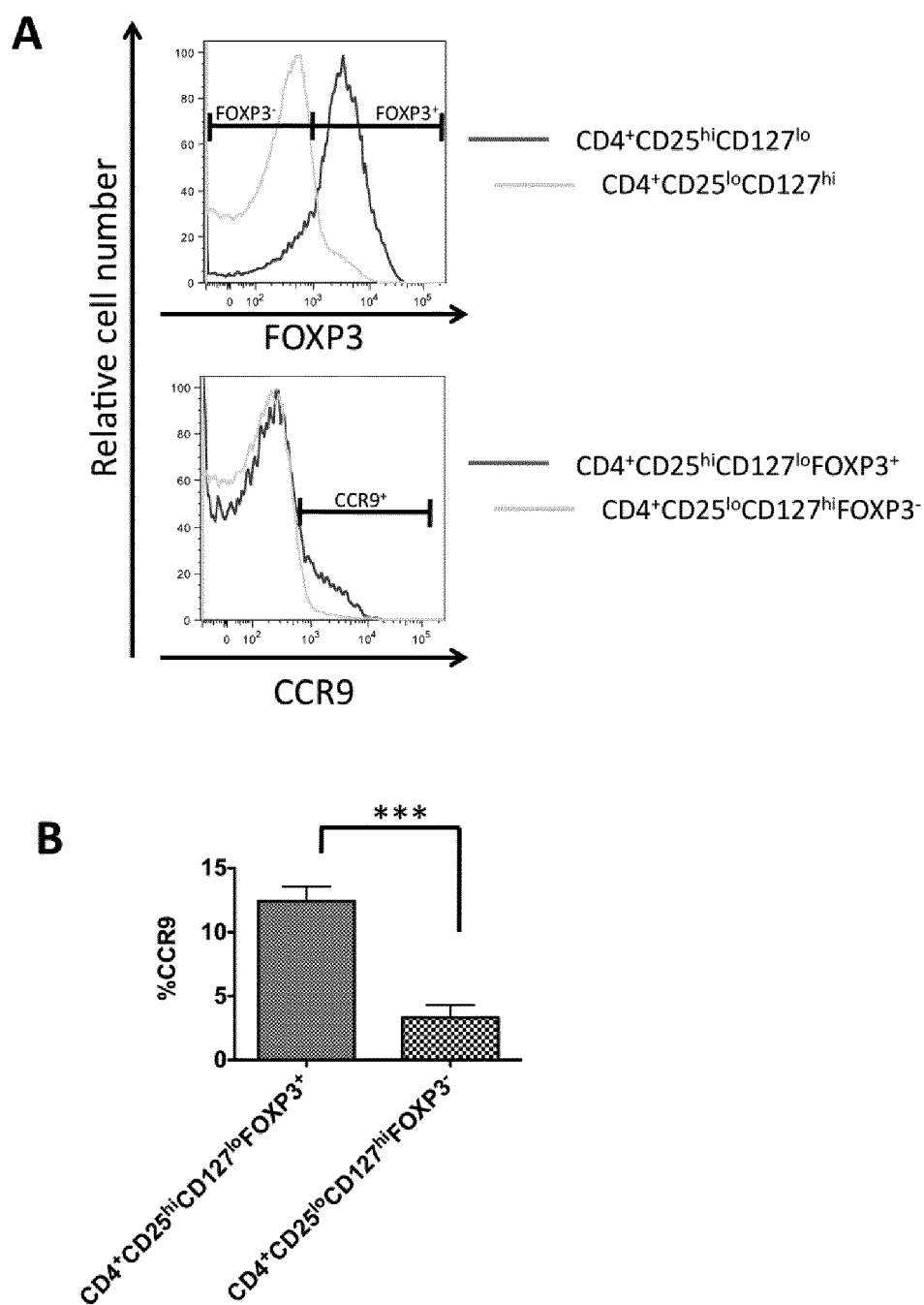

FIG. 3. $CD4^+CD25^{hi}CD127^{lo}FOXP3^+$ Tregs have higher CCR9 expression than $CD4^+CD25^{lo}CD127^{hi}FOXP3^-$ non-Tregs in MLN draining the small bowel. A) Single cell suspensions were prepared from small bowel draining MLNs resected from a CD patient and stained for CD4, CD25, CD127, FOXP3 and CCR9. $CD4^+CD25^{hi}CD127^{lo}$ Treg and $CD4^+CD25^{lo}CD127^{hi}$ effector T-cell populations were gated and overlaid as histograms of FOXP3 intensity (top panel). Histogram gates were used to select $FOXP3^+$ and $FOXP3^-$ populations and expressed as overlaid histograms of CCR9 intensity for $CD4^+CD25^{hi}CD127^{lo}FOXP3^+$ Treg and $CD4^+CD25^{lo}CD127^{hi}FOXP3^-$ effector populations (bottom panel). CCR9 histogram gate was used to quantify results (n=3) in (B).

Figure 4:
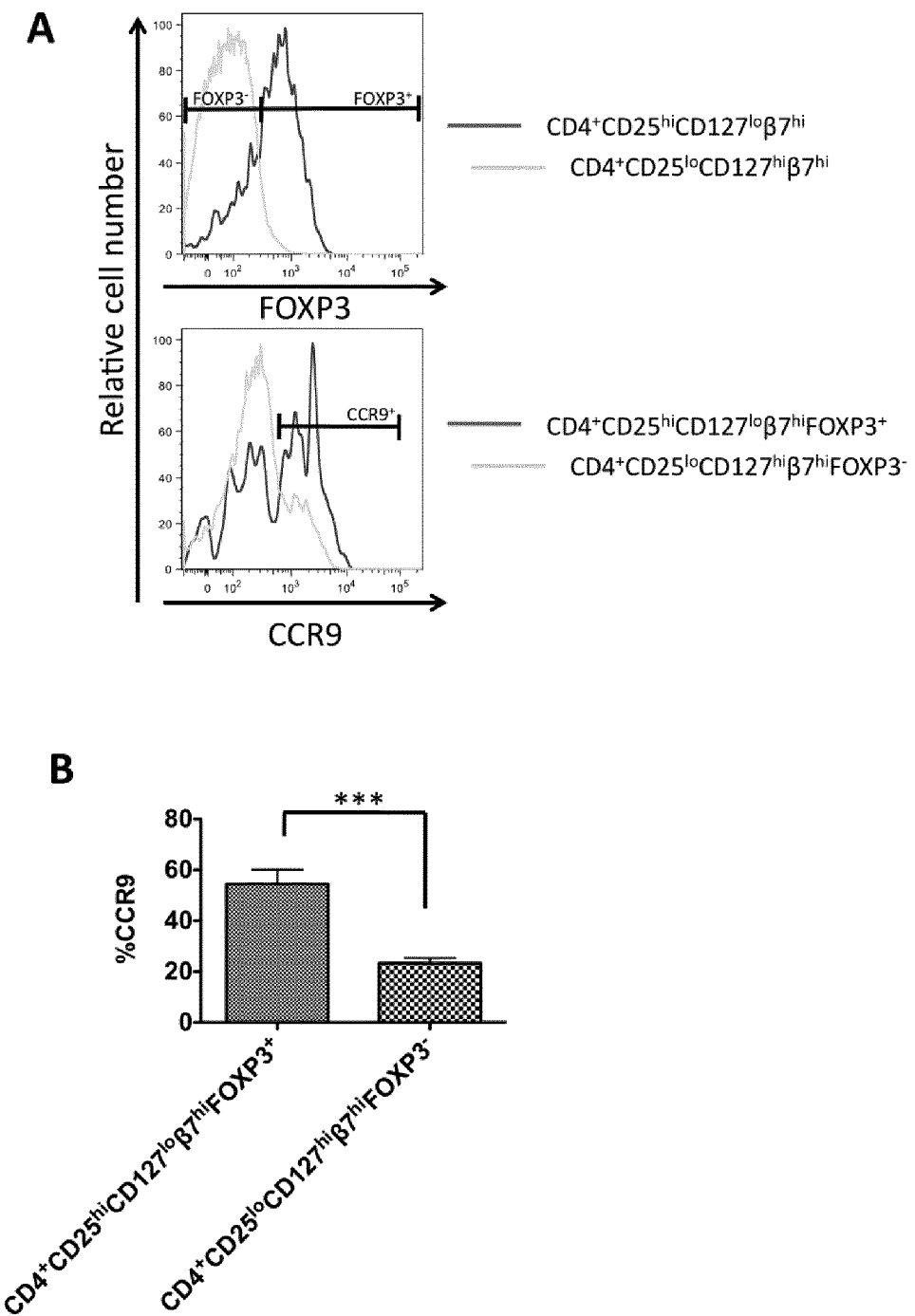

FIG. 4. $CD4^+CD25^{hi}CD127^{lo}\beta 7^{hi}FOXP3^+$ Tregs have higher CCR9 expression than $CD4^+CD25^{lo}CD127^{hi}\beta 7^{hi}FOXP3^-$ non-Tregs in peripheral blood. PBMCs were prepared from healthy controls and stained for CD4, CD25, CD127, FOXP3, β7 and CCR9. $CD4^+CD25^{hi}CD127^{lo}\beta 7^{hi}$ Treg and $CD4^+CD25^{lo}CD127^{hi}\beta 7^{hi}$ effector T-cell populations were gated and overlaid as histograms of FOXP3 intensity (top panel). Histogram gates were used to select $FOXP3^+$ and $FOXP3^-$ populations and expressed as overlaid histograms of CCR9 intensity for $CD4^+CD25^{hi}CD127^{lo}\beta 7^{hi}FOXP3^+$ Treg and $CD4^+CD25^{lo}CD127^{hi}\beta 7^{hi}FOXP3^-T_{eff}$ populations (bottom panel). CCR9 histogram gate was used to quantify results (n=3) in (B).

Figure 5:
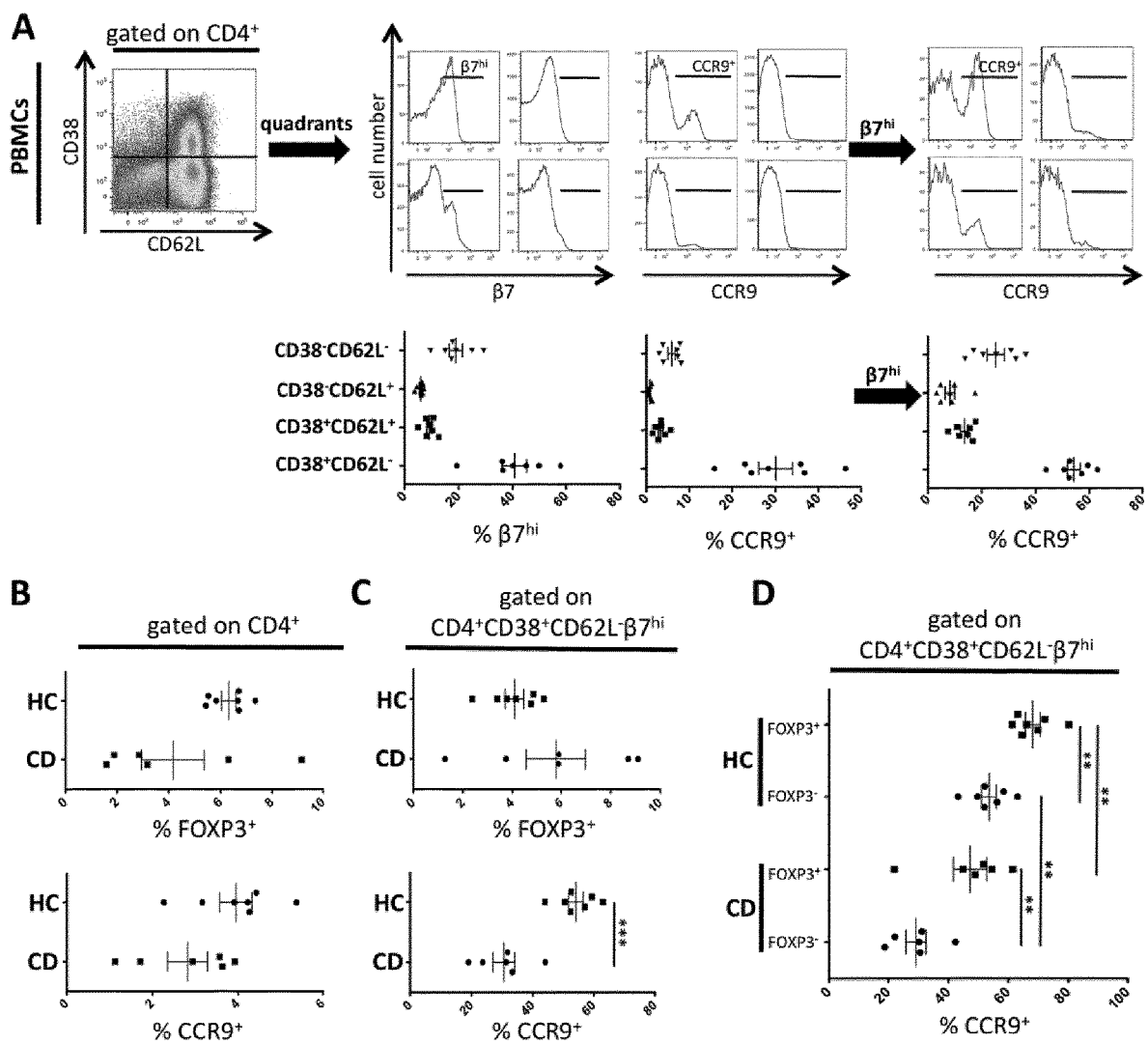

FIG. 5. $CD4^+CD38^+CD62L^-$ mucosal-educated $FOXP3^+$ $T_{regs}$ in peripheral circulation carry higher CCR9 marking than $FOXP3^-$ $T_{effs}$ and CD patients have diminished overall CCR9 marking on mucosal-educated T-cells. (A) PBMCs prepared from healthy controls (HC) were stained for CD4, FOXP3, CD38, CD62L, β7 and CCR9 then analysed by flow cytometry. Lymphocytes were gated for CD4, expressed as CD38vsCD62L dot plots and divided into quadrants (left hand panel). Histograms of each quadrant are displayed for signal intensity of β7, CCR9 and CCR9 after further gating on $\beta 7^{hi}$(upper panels). Histogram gates were used to quantify signal intensities in each quadrant (n=7, lower panels). (B-D) PBMCs isolated from HC (n=7) and small bowel CD patients (n=6) were analysed as in (A). (B) Percentage of $FOXP3^+$ (upper panel) and $CCR9^+$ (lower panel) cells among total CD4 cells. (C) Percentage of $FOXP3^+$ (upper panel) and $CCR9^+$ (lower panel) cells among gated $CD4^+CD38^+CD62L^-\beta 7^{hi}$ cells. (D) Percentage of $CCR9^+$ cells among gated $CD4^+CD38^+CD62L^-\beta 7^{hi}$ further gated on $FOXP3^+$ and $FOXP3^-$ cells.

Figure 6:
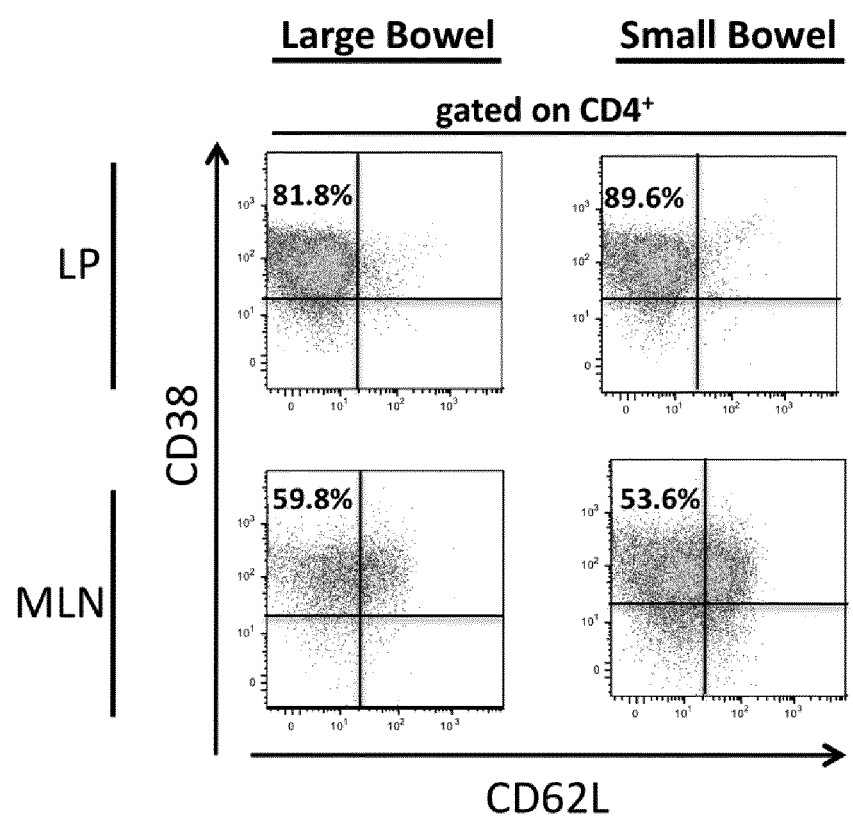

FIG. 6. T-cells of $CD38^+CD62L^-$ phenotype predominate in the LP of the small and large bowel. Single cell suspensions prepared from LP (top panels) and MLN (bottom panels) of large bowel (left panels) and small bowel (right panels) were stained for CD4, C38 and CD62L. $CD4^+$ cells were expressed as CD38vsCD62L dotplots. Values in upper left quadrant represent percentage of $CD38^+CD62L^-CD4$ cells in this quadrant (n=1). Small bowel LP and MLN were from the ileum, large bowel LP and MLN were from the right colon resected from patient undergoing surgery for colorectal cancer.

Figure 7:
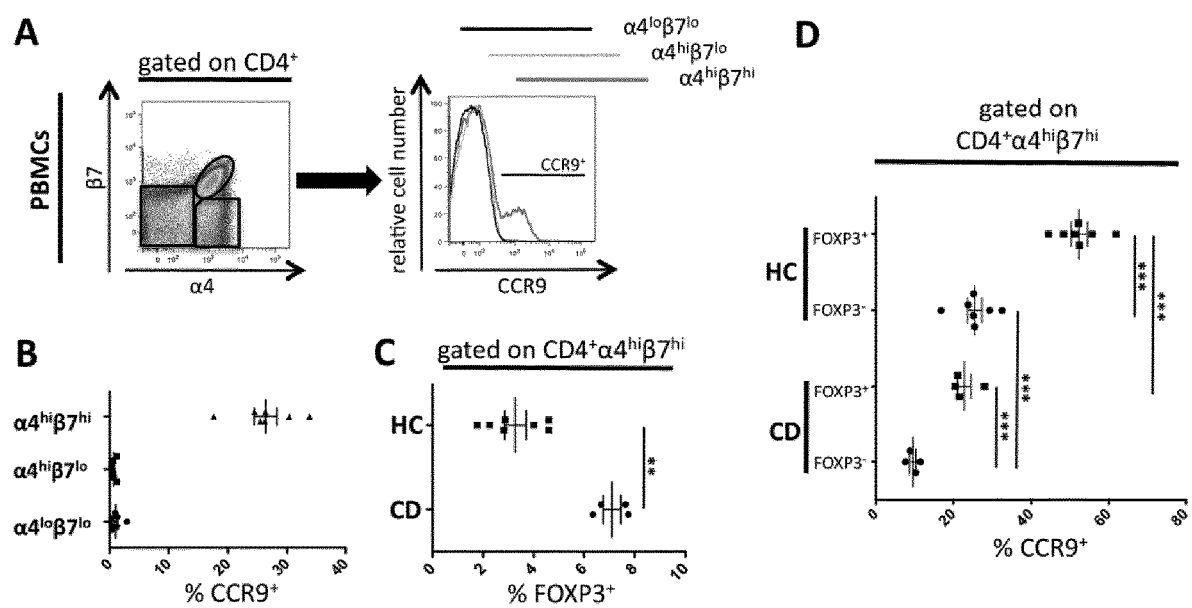

FIG. 7. $CD4^+\alpha 4^{hi}\beta 7^{hi}$ mucosal-tropic $FOXP3^+$ Tregs in peripheral circulation carry higher CCR9 marking than $FOXP3^-$ $T_{effs}$ and CD patients have diminished CCR9 marking on mucosal-tropic T-cells (A) PBMCs prepared from HC were stained for CD4, FOXP3, β7, α4 and CCR9 then analysed by flow cytometry. Lymphocytes were gated for CD4, expressed as β7vsα4 dot plots and gated for $\alpha 4^{hi}\beta 7^{hi}$, $\alpha 4^{hi}\beta 7^{lo}$, $\alpha 4^{lo}\beta 7^{lo}$ (left panel), and displayed as overlaid histograms of CCR9 intensity (right panel). (B) Quantified CCR9 positivity among HC (n=7), for analysis as performed in (A). (C-D) PBMCs isolated from HC (n=7) and CD patients (n=4) were analysed as in (A). (C) Percentage of $FOXP3^+$ cells among gated $CD4^+\alpha 4^{hi}\beta 7^{hi}$ cells. (D) Percentage of CCR9 cells among gated $CD4^+\alpha 4^{hi}\beta 7^{hi}$ cells, further gated on $FOXP3^+$ and $FOXP3^-$ cells.

Figure 8:
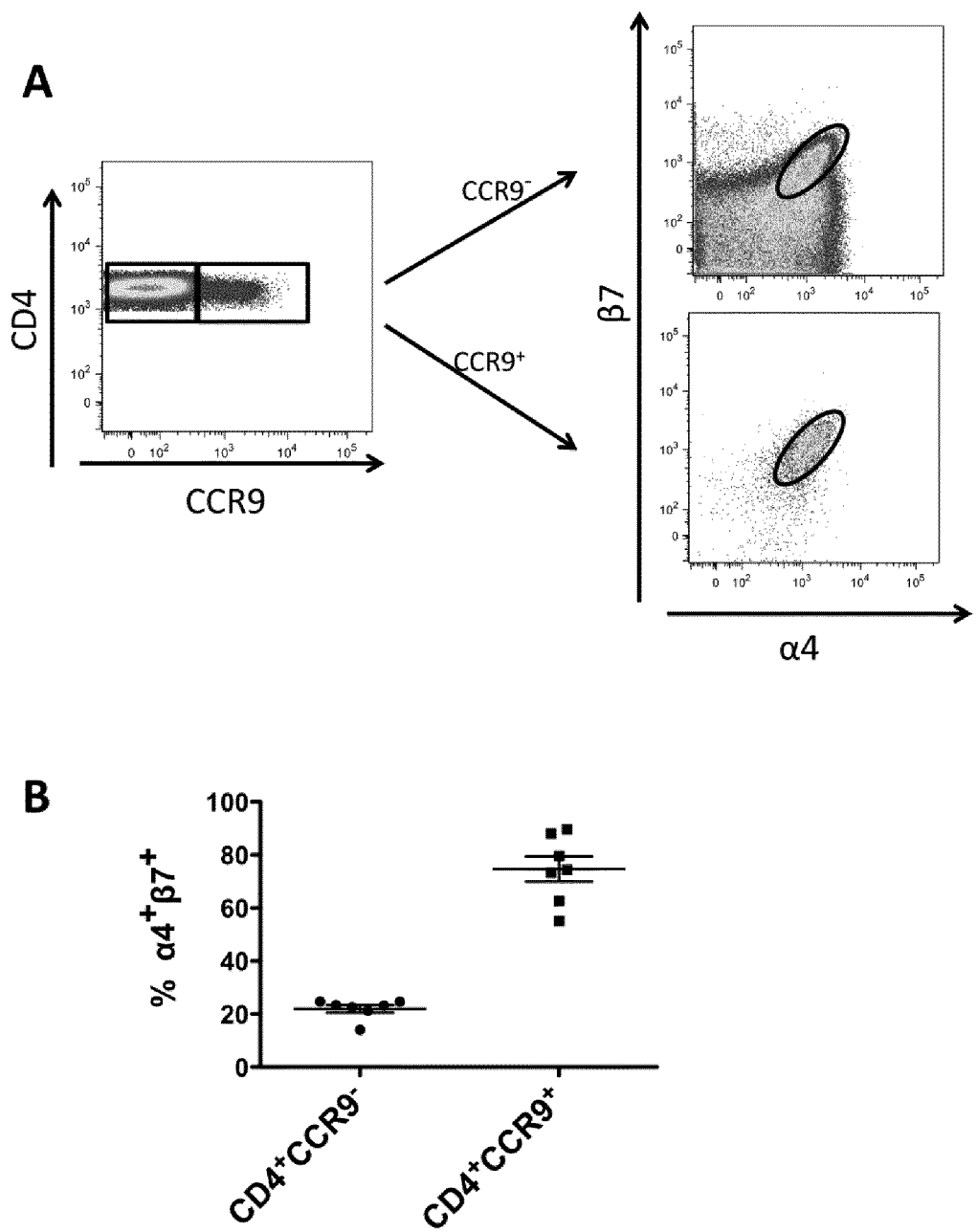

FIG. 8. The majority of $CD4^+CCR9^+$ T-cells in peripheral circulation carry $\alpha 4^{hi}\beta 7^{hi}$ expression. (A) PBMCs prepared from healthy controls and stained for CD4, α4, β7 and CCR9. $CD4^+$ cells were expressed as CD4vsCCR9 dotplots and $CD4^+CCR9^+$ and $CD4^+CCR9^-$ populations subsequently expressed as β7vsα4 dotplots. The percentage of cells inside the $\alpha 4^{hi}\beta 7^{hi}$ gate is quantified (n=7) in (B).

Figure 9:
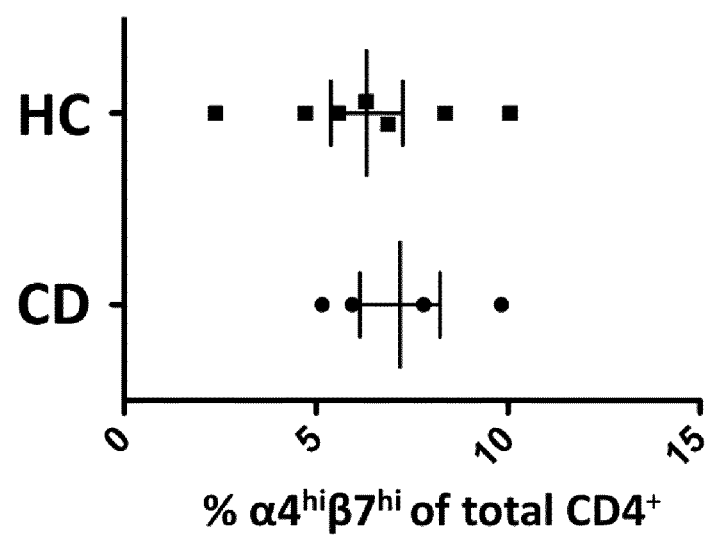

FIG. 9. No difference in total numbers of $CD4^+\alpha 4^{hi}\beta 7^{hi}$ T-cells in peripheral circulation of CD patients and healthy controls. PBMCs prepared from healthy controls (HC) and CD patients were stained for CD4, FOXP3, β7, α4 and CCR9 then analysed by flow cytometry. Lymphocytes were gated for CD4+ and expressed as β7vsα4 dotplots. The percentage of CD4 cells inside the α4β7$^{hi}$ is shown for HC (n=7) and CD patients (n=4).

Figure 10:
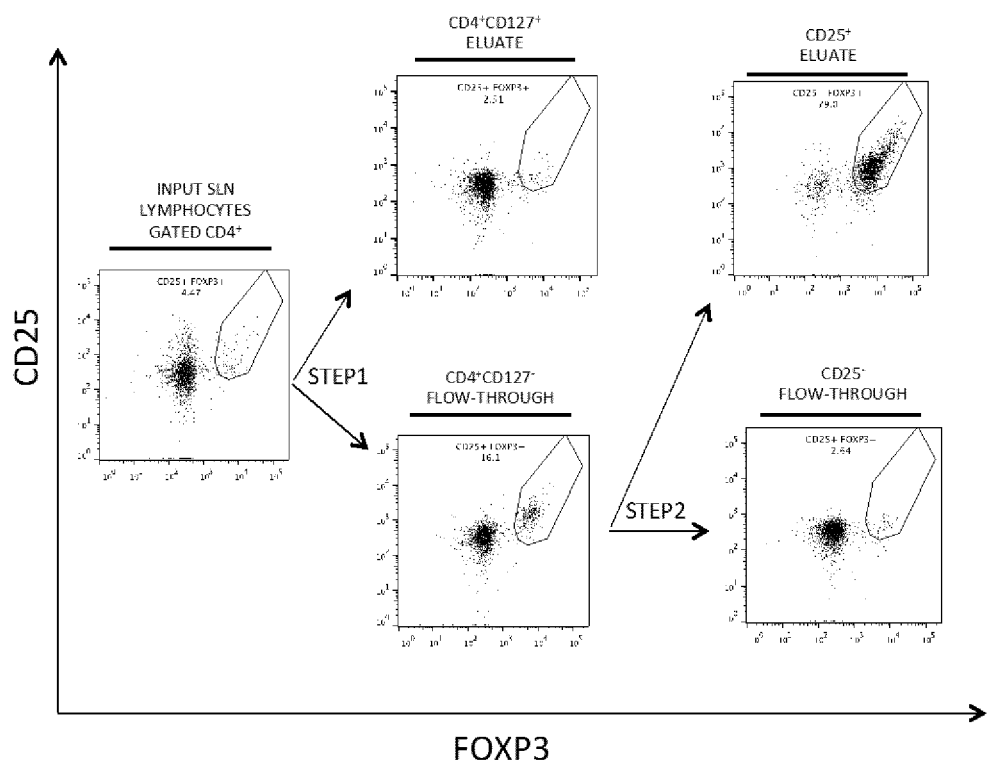

FIG. 10. MACS 2-Step enrichment of MLN Tregs. Total lymphocytes recovered from MLN of patient with CD were processed using Miltenyi Regulatory T Cell Isolation Kit II and an autoMACSpro instrument. Input cells are displayed in the far left plot, gated on CD4, and expressed as CD25vsFOXP3. CD25$^{hi}$FOXP3+ cells are enriched in the CD4+CD127− flow-through of the first negative selection step, then compared to CD4+CD127+ positively selected eluate from the same step (middle panels). Further enrichment of CD25$^{hi}$FOXP3+ cells to approximately 80% is observed in the positive selection eluate of the second MACS step.

Figure 11:
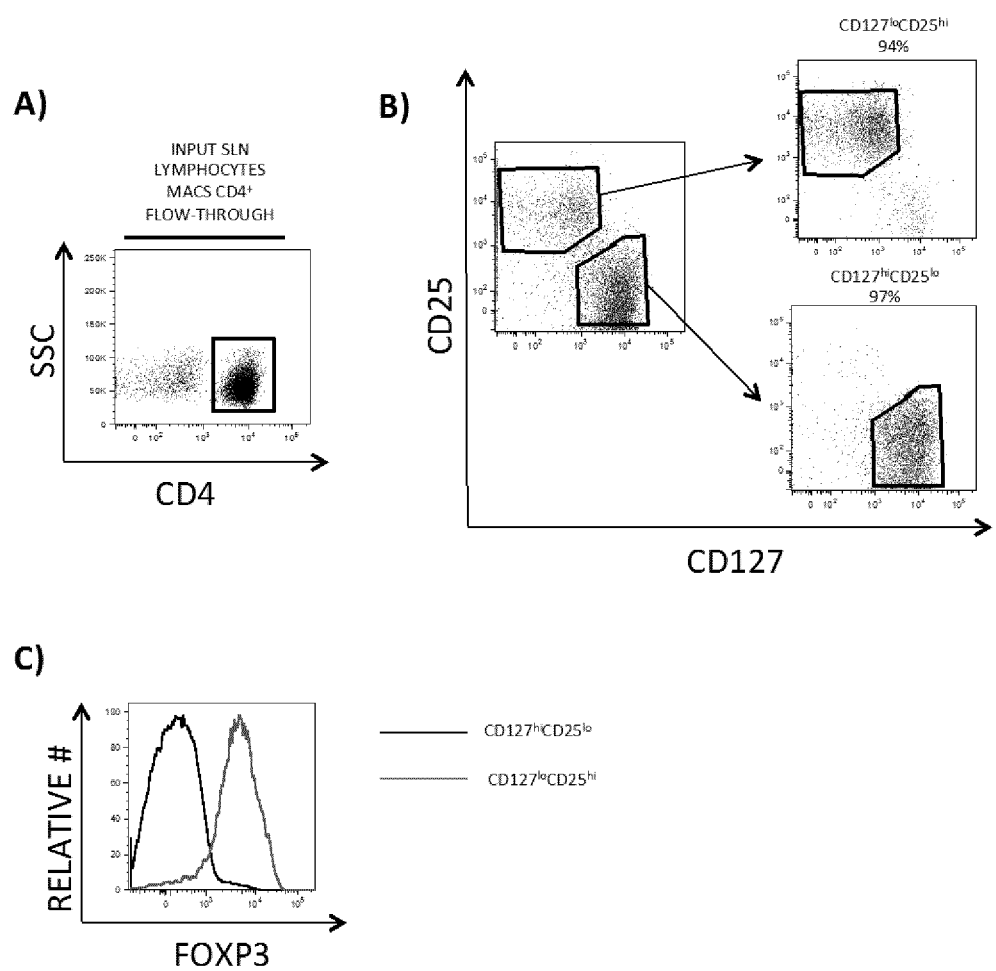

FIG. 11. MACS enrichment and FACS purification of Tregs from MLN. Total lymphocytes recovered from MLN of patient with CD were processed using Miltenyi CD4+ T Cell Isolation Kit II and an autoMACSpro instrument. Cells were immediately labeled with CD4, CD25 and CD127 antibodies and run on FACSaria II instrument. Ungated events are displayed as SSCvsCD4 to assess enrichment (A). CD4-gated events in A) are displayed in the left panel of B). CD25$^{hi}$CD127$^{lo}$ and CD25$^{lo}$CD127$^{hi}$ gates of the resulting plot represent sorting-gates (left panel). A small amount of resulting sorted populations were immediately re-acquired on the FACSaria and displayed in the same plot format (right panels) to assess purity. A portion of the resulting cell population was fixed/permeabilised and stained for FOXP3. Cells were acquired on a FACScalibur instrument, and displayed as FOXP3 histograms of CD25$^{lo}$CD127$^{hi}$ and CD25$^{hi}$CD127$^{lo}$ populations (C).

Figure 12:
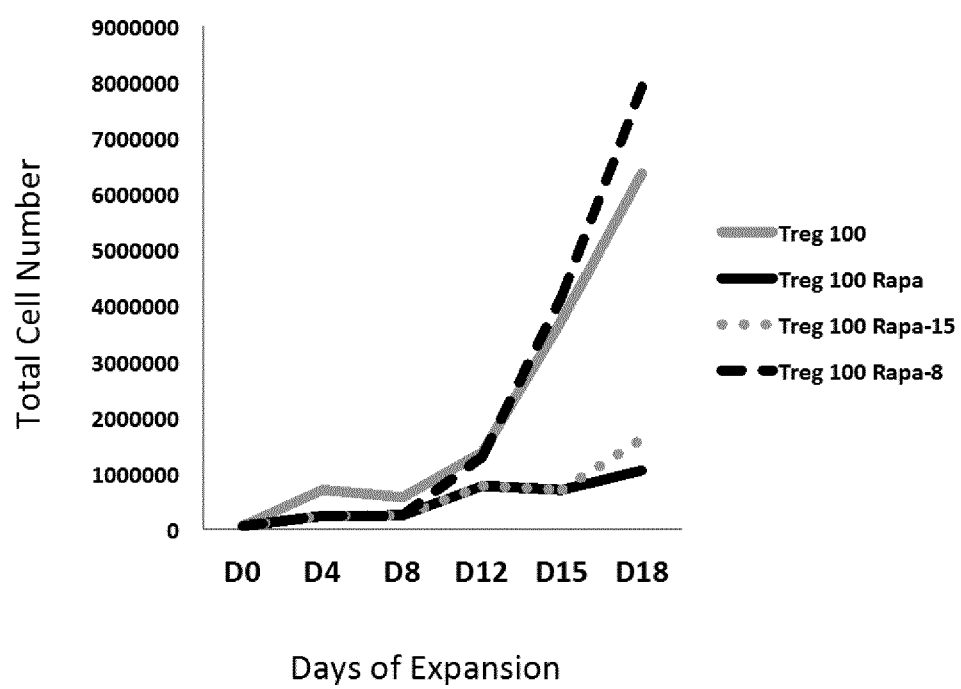

FIG. 12. Viable cell numbers of MACS-enriched MLN Tregs over 18 days of ex vivo expansion. Total lymphocytes recovered from MLN of patient with CD were processed using Miltenyi Regulatory T Cell Isolation Kit II and an autoMACSpro instrument. Resulting CD4+CD25$^{lo}$CD127$^{hi}$ cells were rested overnight before being activated for 24 hrs with antiCD3/CD28 magnetic microbeads. After 24 hours of activation IL2 (100 IU·mL) was added in the presence or absence of Rapamycin. Magnetic beads were removed after 24 hrs further culture, and IL2 and rapamycin were refreshed every 24 to 48 hrs while maintaining cell density below $3 \times 10^6$ .mL by addition of fresh media and culture vessel exchanges. All cells were restimulated with antiCD3/CD28 magnetic microbeads for 24 hrs starting on day 12. Treg100 group was cultured without rapamycin supplement for the entire 18 day experiment, where Treg100 Rapa groups was cultured with rapamycin for the entire 18 days.

Figure 13:
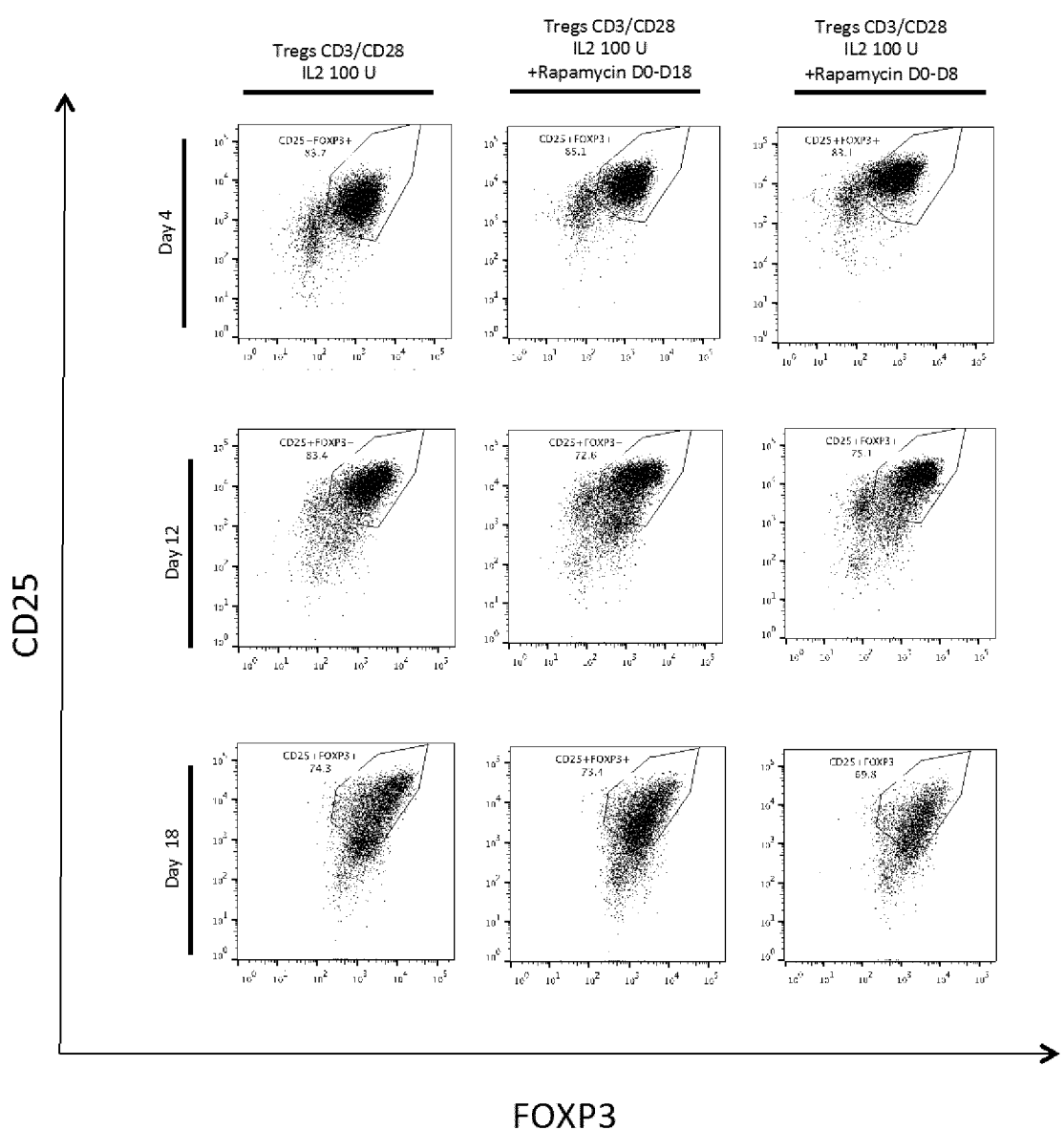

FIG. 13. CD25–FOXP3 expression on MACS-enriched MLN Tregs on days 4, 12 and 18 of 18-day of ex vivo expansion. MLN Treg expansion from FIG. 12 analysed at days 4, 12 and 18 for expression of CD25 and FOXP3. Cells were recovered for counting of viable population of each day, and a small aliquot stained for CD25 and FOXP3. Data was acquired on a FACScalibur instrument. Dead cells were excluded by Live/Dead fixable viability stain.

Figure 14:
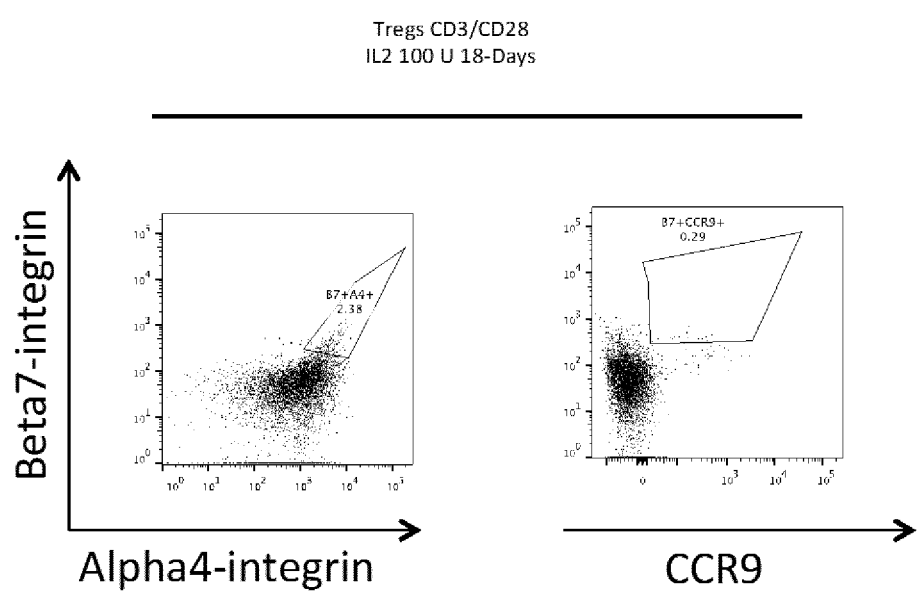

FIG. 14. Homing receptor pattern on MACS-enriched MLN Tregs after 18-days of ex vivo expansion. MLN Treg expansion from FIG. 12 analysed at day 18 for expression of beta7– and alpha4– integrins and CCR9 expression. Cells were recovered for experimental manipulation, and a small aliquot stained for beta7– and alpha4– integrins and CCR9. Data was acquired on a FACScalibur instrument. Dead cells were excluded by Live/Dead fixable viability stain.

Figure 15:
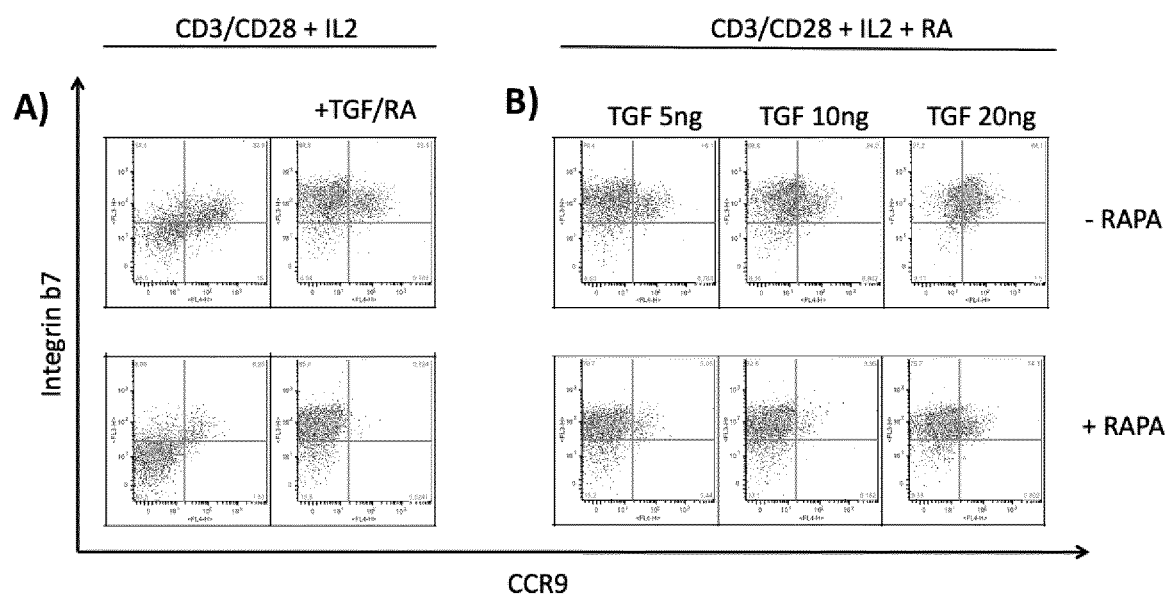

FIG. 15. Homing receptor expression and repatterning on MACS-enriched and FACS-purified MLN Tregs after 4-days of ex vivo expansion. Total lymphocytes recovered from MLN of patient with CD were processed using Miltenyi CD4+ T Cell Isolation Kit II and an autoMACSpro instrument. Cells were immediately labeled with CD4, CD25 and CD127 antibodies and sorted on FACSaria II instrument for CD4+CD25$^{hi}$CD127$^{lo}$ cells. Resulting purified population of Tregs was rested overnight before 24 hr activation with antiCD3/CD28 magnetic microbeads. After 24 hours IL2 and all other indicated stimuli were added, and cultures left for a further 72 hrs. all-trans retinoic acid (RA) was added an 1 nM final concentration, IL2 at 100 IU·mL and microbeads at a ratio of 1:1 beads to cells. TGF in A) was added at 5 ng·mL. Rapamycin was added at 100 nM final concentration. Cells were recovered in 5-volumes of FACS-buffer, washed briefly, and stained for beta7-integrin and CCR9 before analysis on FACScalibur instrument.

Figure 16:
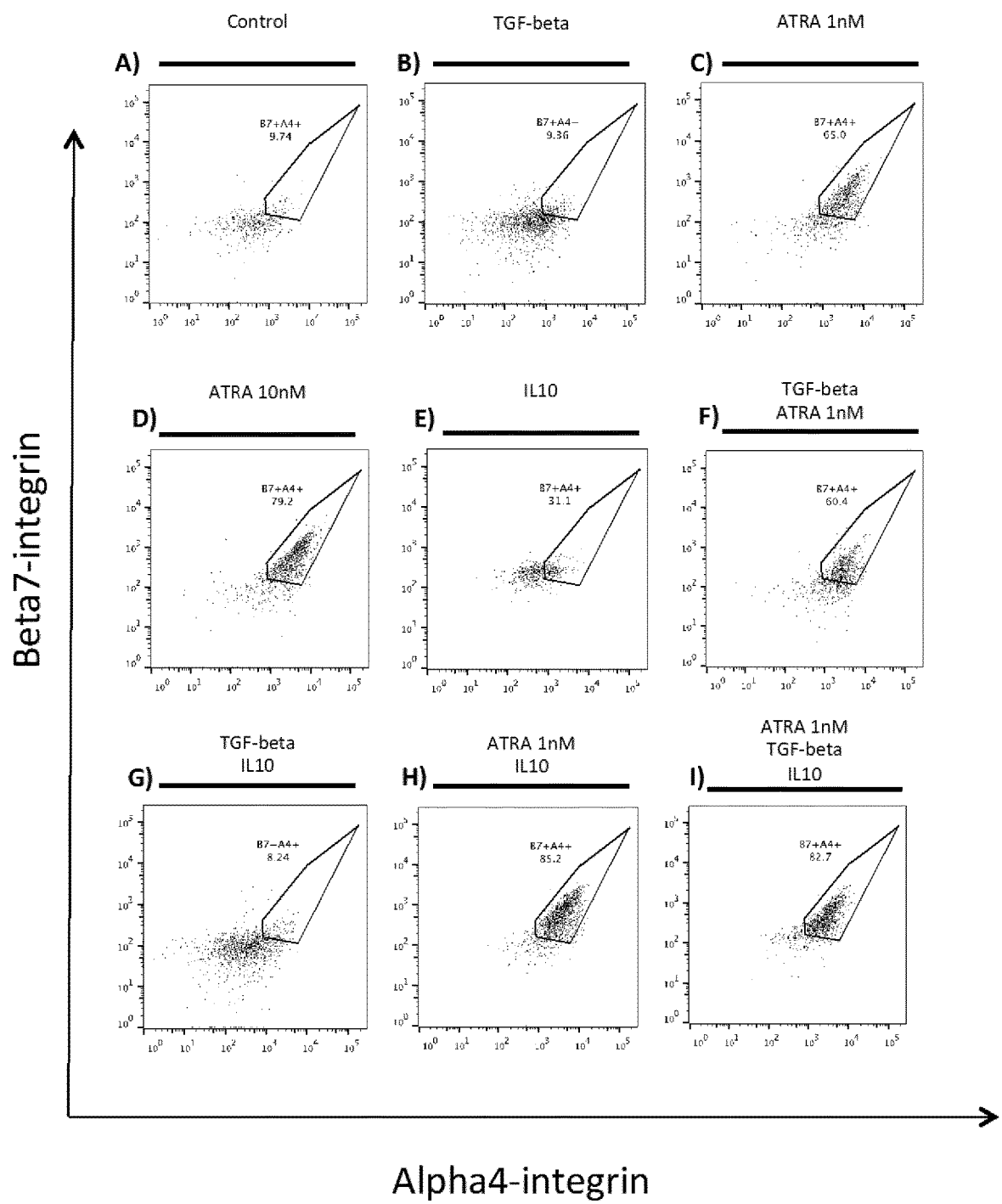

FIG. 16. α4β7 receptor pattern on MACS-enriched MLN Tregs after 18-days of ex vivo expansion and 6-days of receptor repatterning stimulation. MLN Treg expansion from FIGS. 12 and 14 were recovered and aliquoted at 200 thousand cells per well of a 96-well U-bottom plate in 150 uL medium. Cells were stimulated with 100 IU·mL IL2, and indicated stimuli. Control was unstimulated other than IL2. TGF-beta concentration was 12.5 ng·mL. IL10 concentration was 1 ng·mL. Cell medium and stimuli were refreshed at days 2 and 4 by pipetting 50 μL of media supernatant (SN), and resuspending the entire well with 50 μL fresh supplemented media. On day-6 cells were recovered in 5-volumes of FACS-buffer, washed briefly and stained for beta7– and alpha4– integrins, and CCR9, before analysis on FACScalibur instrument. Dead cells are excluded by Live/Dead fixable viability stain.

Figure 17:
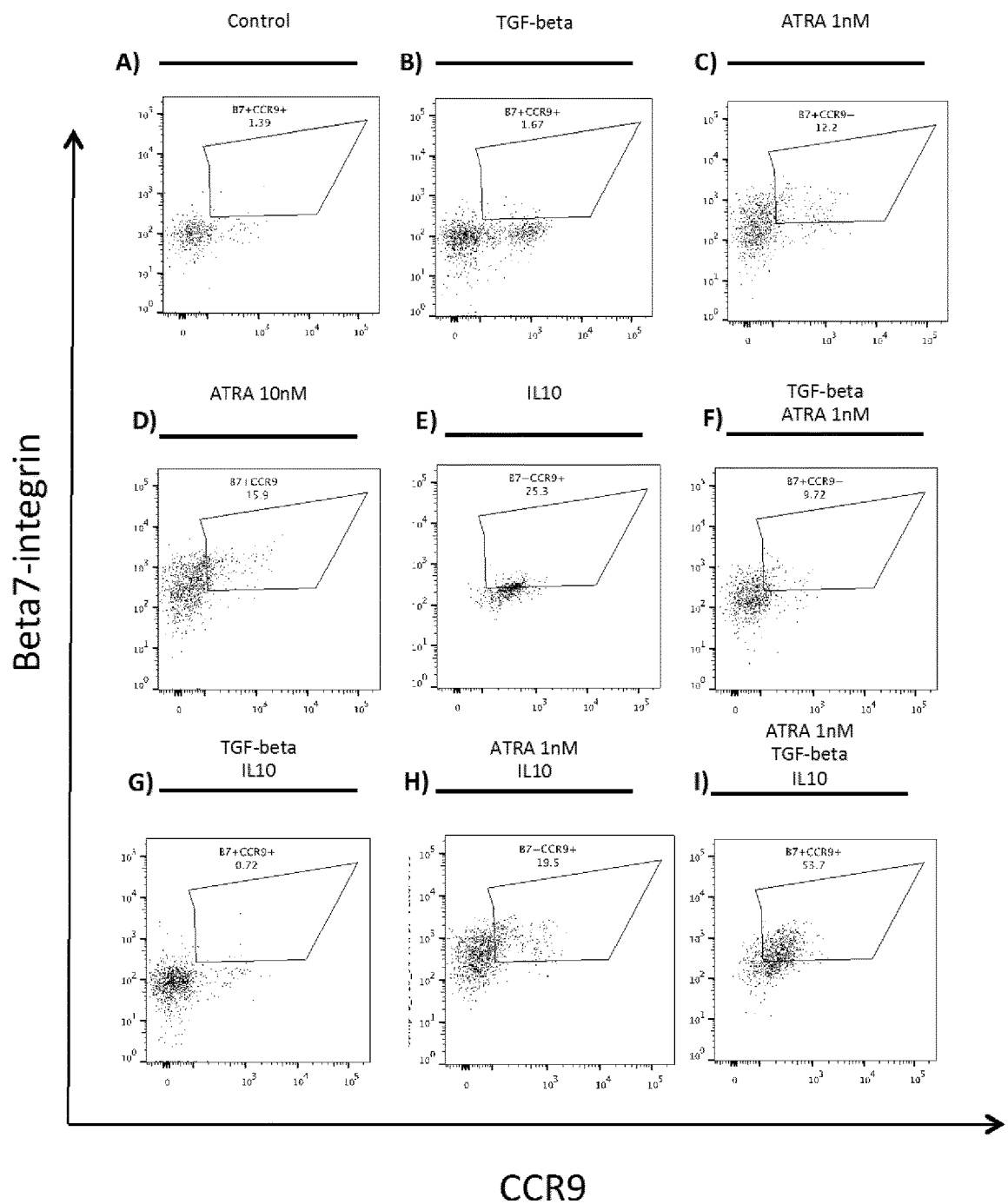

FIG. 17. α4β7 receptor pattern on MACS-enriched MLN Tregs after 18-days of ex vivo expansion and 6-days of receptor repatterning stimulation. Analysis from FIG. 16 re-presented as beta7-integrin vs CCR9.

Figure 18:
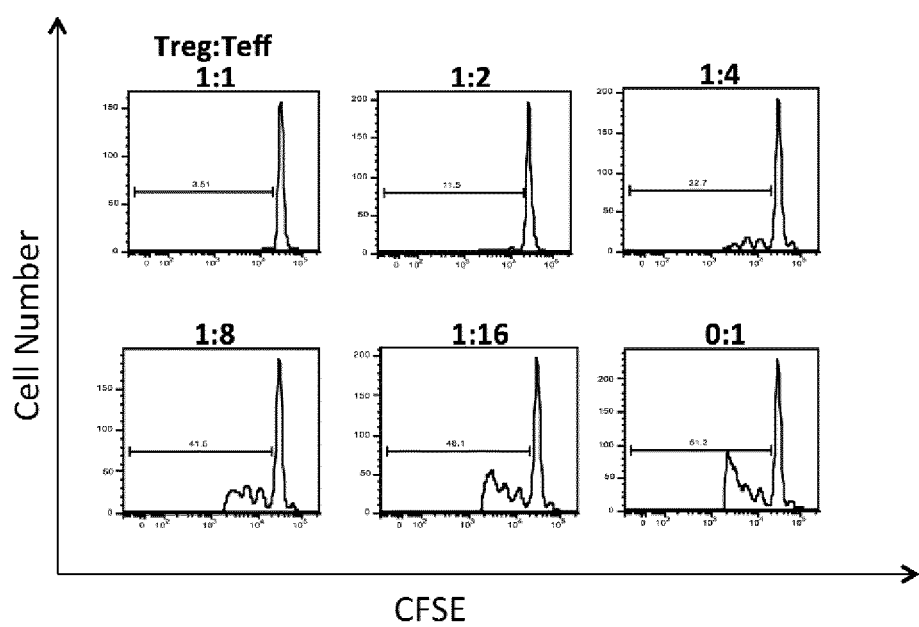

FIG. 18. Day-18 expanded SLN Tregs suppress fresh-thawed CD4 Teff proliferation. Cryopreserved total SLN cells were thawed on Day 15 of Treg expansion and cultured for 48 hours in the presence of IL2. On day 17 Teff cells were sorted as CD4+CD127hiCD25lo and stimulated overnight with CD3/CD28 dynal beads. On day 18 expanded Treg cells were harvested and mixed at indicated ratios with bead-depleted and CFSE labelled Teff cells. CFSE fluorescence was assessed by flow cytometry 4 days after initiation of assay with FOXP3 counterstaining, where histogram show FOXP3– cells.

Figure 19:
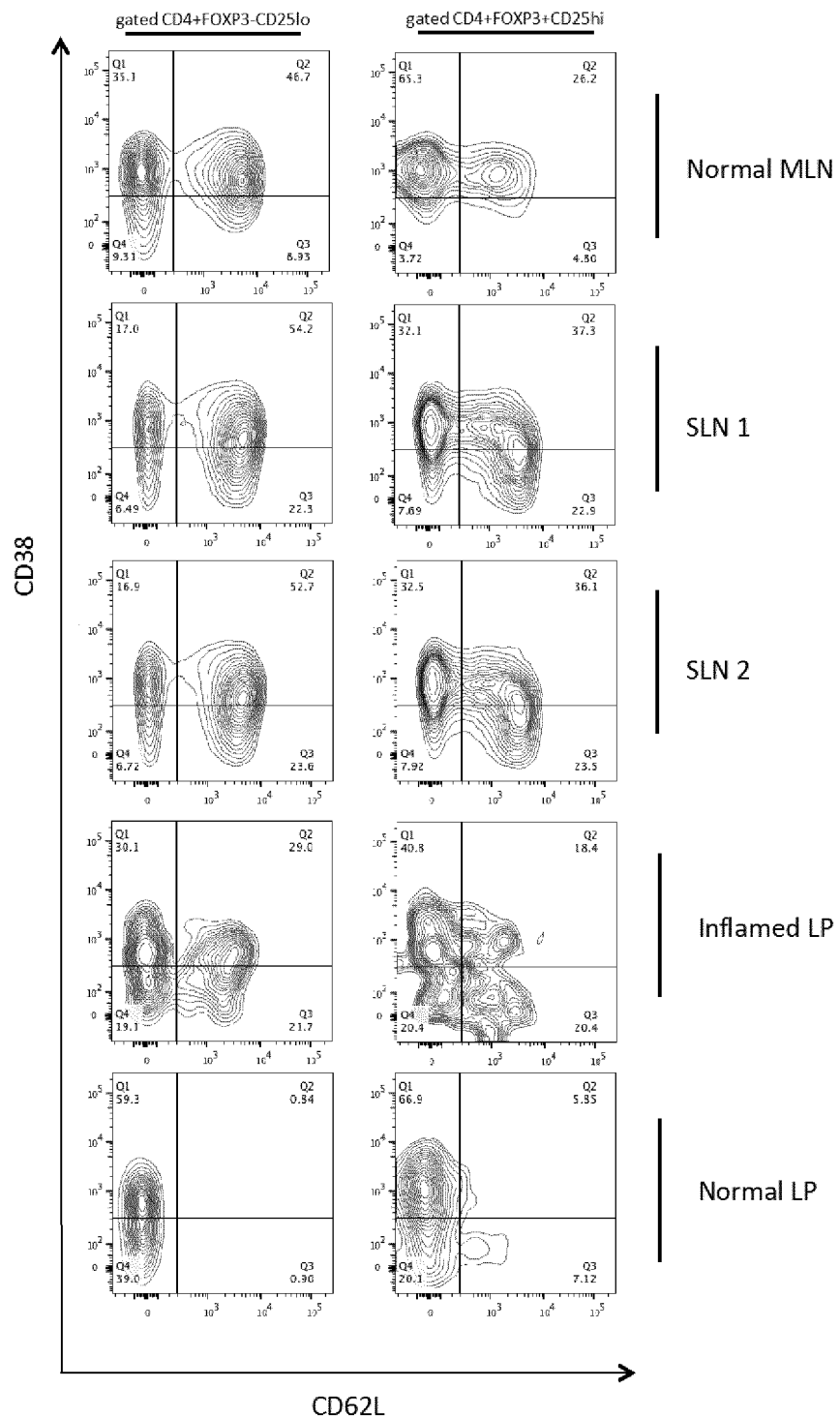

FIG. 19. CD4+CD25$^{hi}$FOXP3+ Tregs and CD4+CD25$^{lo}$FOXP3− Teffs have altered CD38+CD62L− distribution in inflamed tissues of CD patients. Single cell suspensions prepared from indicated resected tissues of a representative CD patient with ileocaecal disease were immediately stained with the indicated antibodies. All plots display CD38 vs CD62L of CD4+CD25$^{hi}$FOXP3+ Tregs (right panels) and CD4+CD25$^{lo}$FOXP3− Teffs (left panels).

Figure 20:
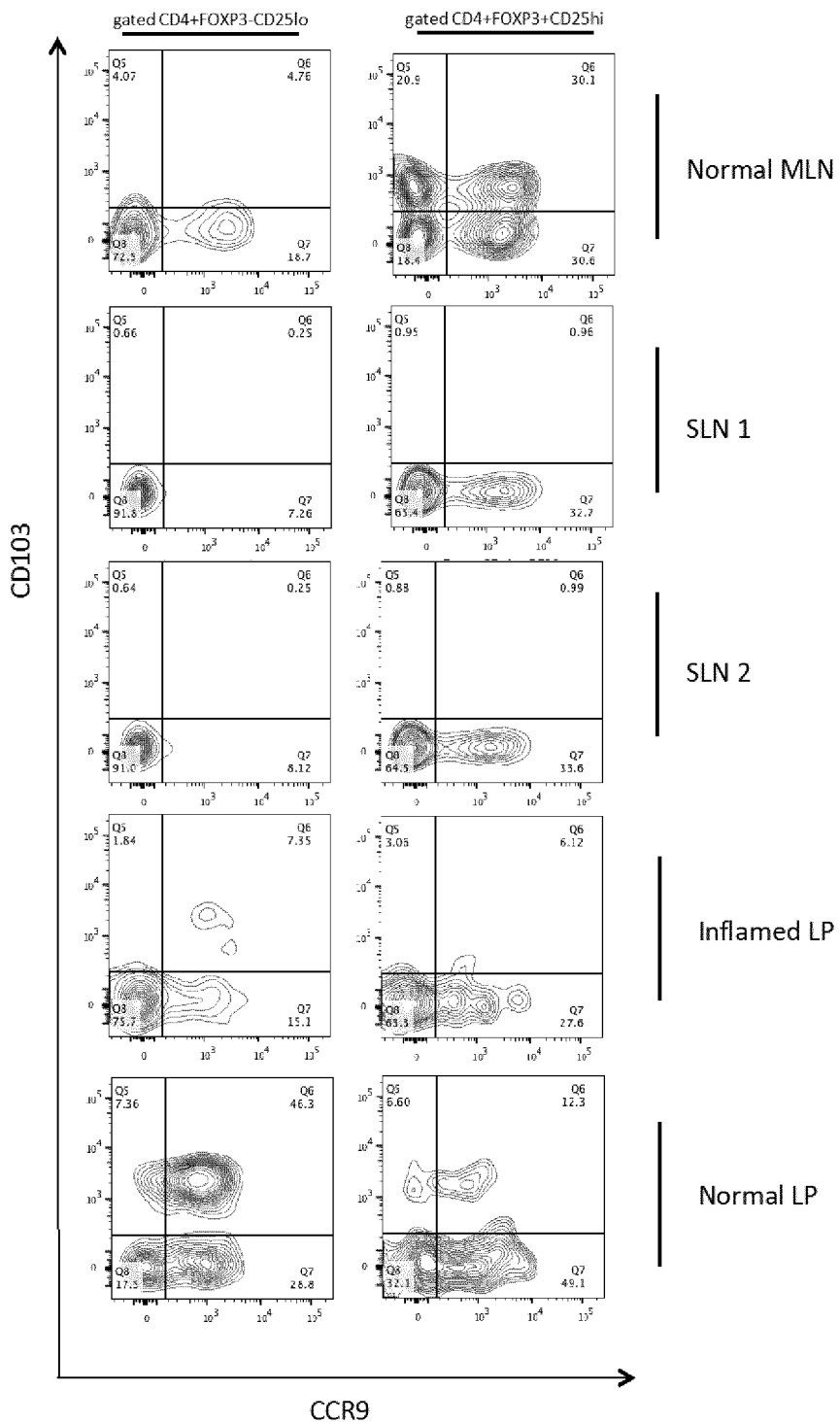

FIG. 20. CD4+CD25$^{hi}$FOXP3+ Tregs and CD4+CD25$^{lo}$FOXP3− Teffs have altered CD103 and CCR9 expression in inflamed tissues of CD patients. Single cell suspensions prepared from indicated resected tissues of a representative CD patient with ileocaecal disease were immediately stained with the indicated antibodies. All plots display CD103 vs CCR9 of CD4+CD25$^{hi}$FOXP3+ Tregs (right panels) and CD4+CD25$^{lo}$FOXP3− Teffs (left panels).

Figure 21:
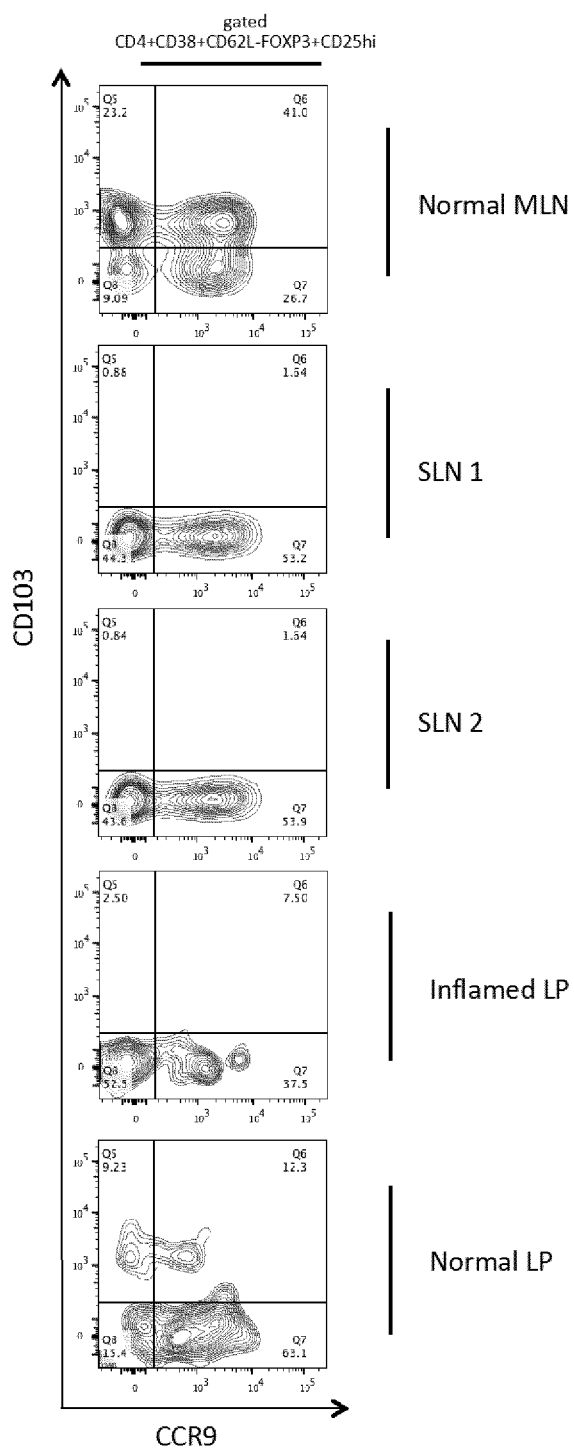

FIG. 21. CD4+CD25$^{hi}$FOXP3+CD38+CD62L− Tregs have altered CD103 and CCR9 expression in inflamed tissues of CD patients. Single cell suspensions prepared from indicated resected tissues of a representative CD patient with ileocaecal disease were immediately stained with the indicated antibodies. All plots display CD103 vs CCR9 of CD4$^+$CD25$^{hi}$FOXP3$^+$CD38$^+$CD62L$^-$ Tregs.

Figure 22:
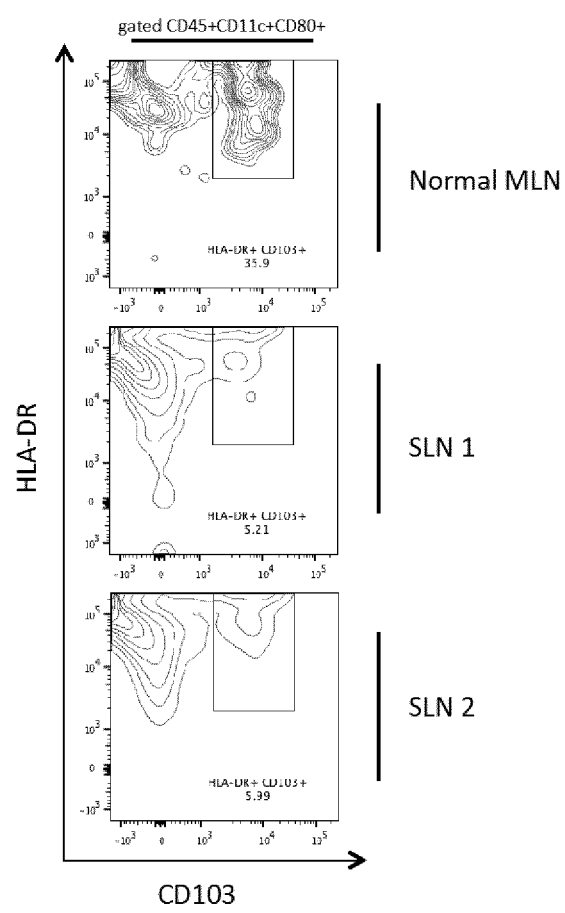

FIG. 22. Diminished representation of CD45$^+$ CD11c$^{hi}$CD80$^+$HLA-DR$^{hi}$CD103$^+$ DCs in inflamed MLN of CD patients. Single cell suspensions prepared from indicated resected tissues of a representative CD patient with ileocaecal disease were immediately stained with the indicated antibodies. All plots display HLA-DR vs CD103 of CD45$^+$CD11c$^{hi}$CD80$^+$ cells.

Figure 23:
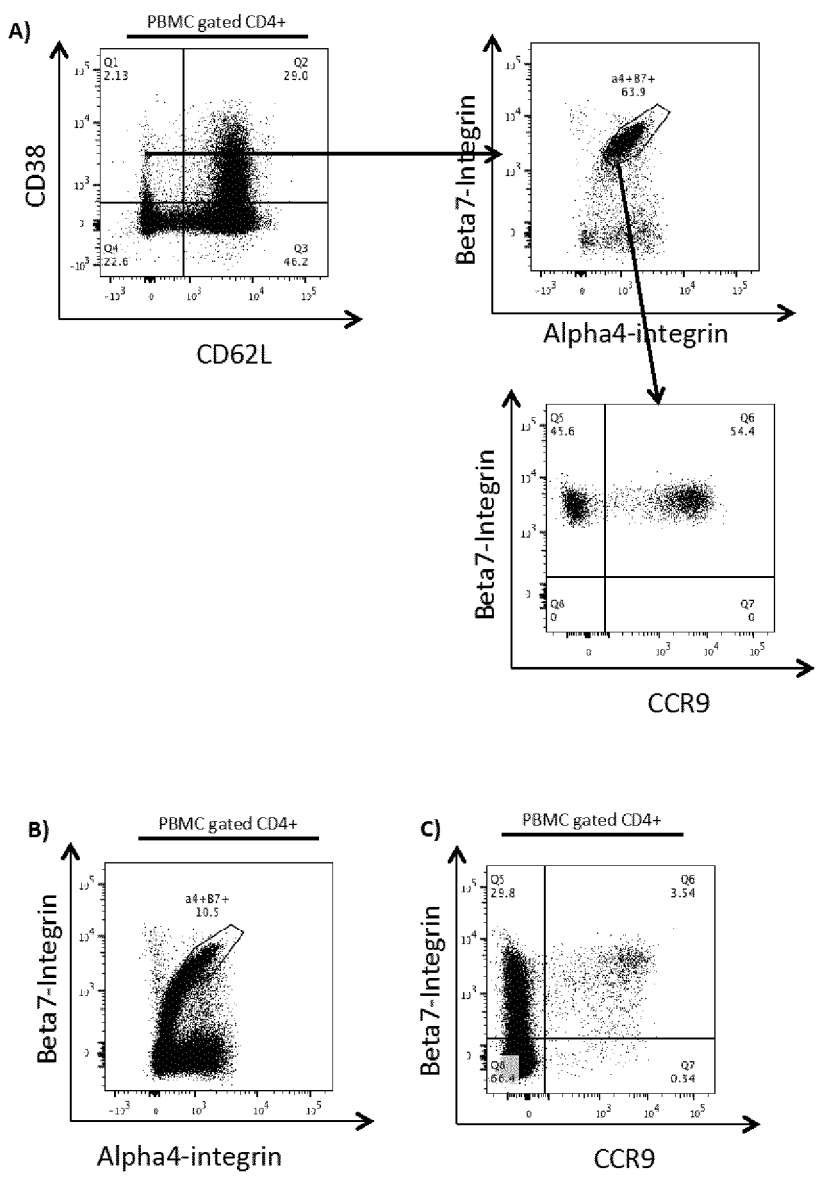

FIG. 23. CCR9 enrichment in CD4$^+$CD38$^+$CD62L$^-$α4$^+$ β7$^+$ T-cells in the peripheral blood. PBMC recovered from healthy donor blood over ficoll were immediately labelled with indicated antibodies and analysed by flow cytometry. A) Displays gating strategy flow with arrows. B) and C) display total CD4$^+$ PBMCs as reference.

Figure 24:
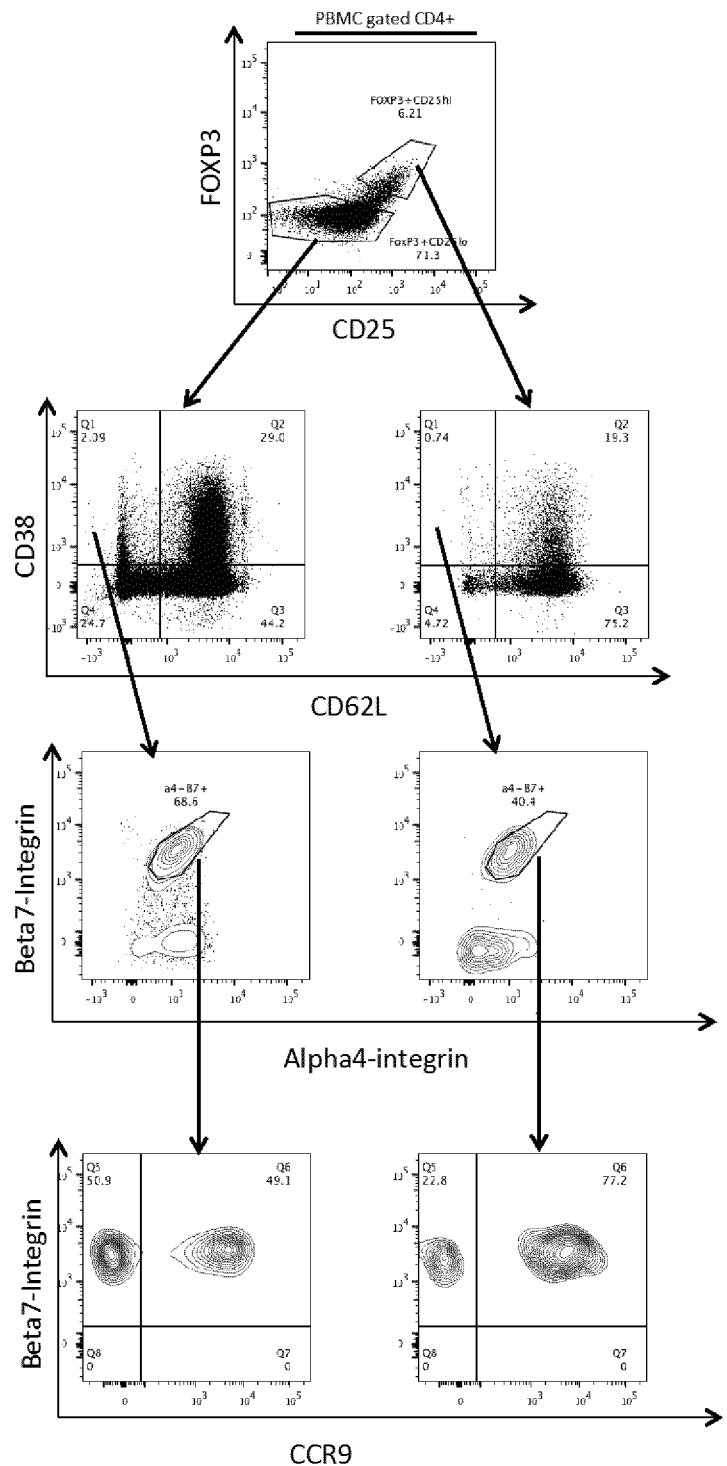

FIG. 24. CCR9 enrichment in CD4$^+$FOXP3$^+$ CD25$^{hi}$CD38$^+$CD62L$^-$α4$^+$β7$^+$ T-cells in the peripheral blood. PBMC recovered from healthy donor blood over ficoll were immediately labelled with indicated antibodies and analysed by flow cytometry. A) Displays gating strategy flow with arrows. Left panels display FOXP3$^-$CD25$^{lo}$Teffs and right panels display FOXP3$^+$CD25$^{hi}$ Tregs.

Figure 25:
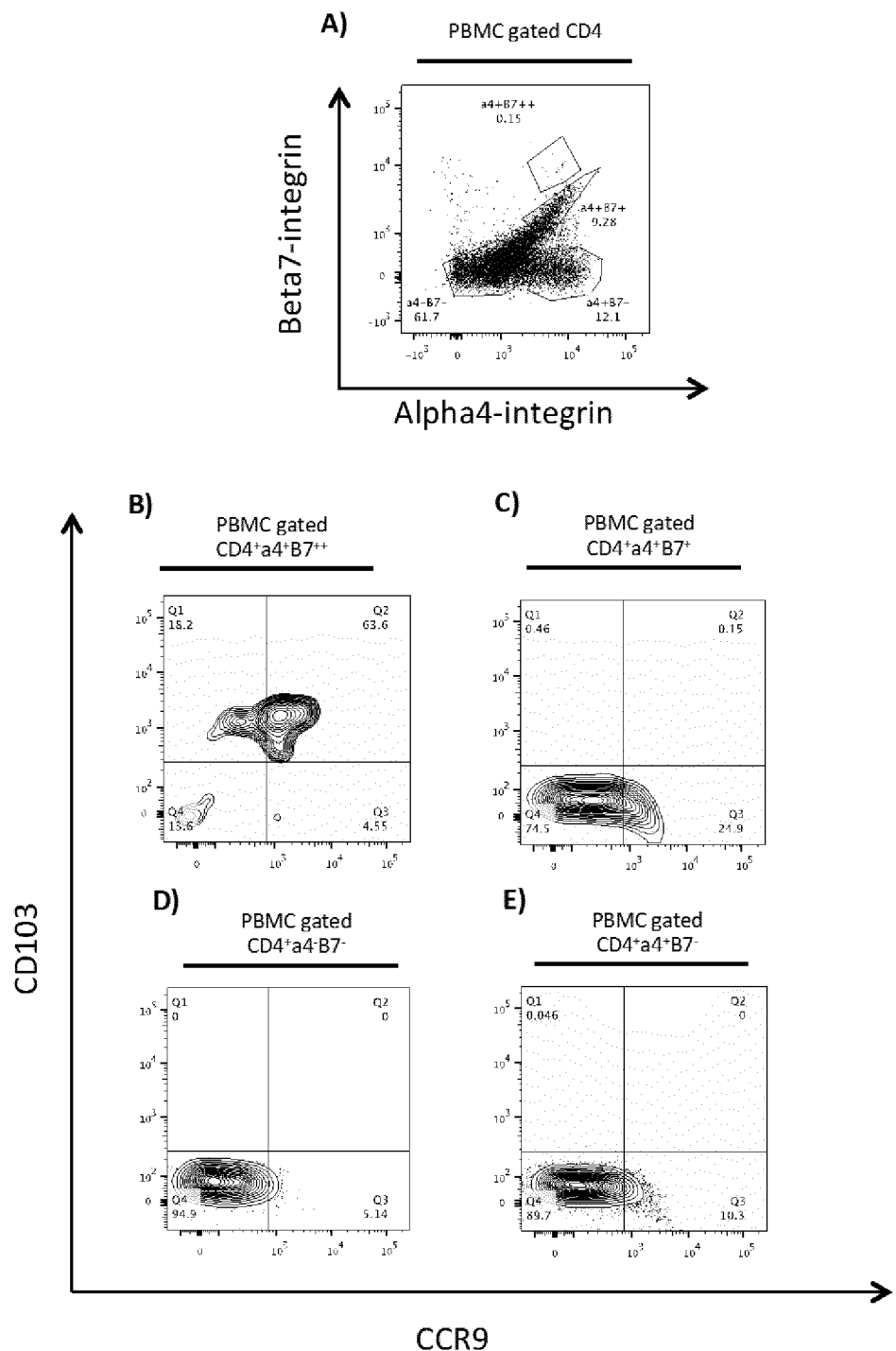

FIG. 25. CD4$^+$α4$^+$β7$^{high}$ T-cells in the peripheral blood are enriched for CD103 and CCR9 expression. PBMC recovered from healthy donor blood over ficoll were immediately labelled with indicated antibodies and analysed by flow cytometry. A) Total CD4 lymphocytes expressed as beta7− vs alpha4− integrin dot plots. Each gate defining alpha4+beta7++, alpha4+beta7+, alpha4−beta7− and alpha4+beta7− are redisplayed as CD103 vs CCR9 contour plots in B), C), D) and E), respectively.

Figure 26:
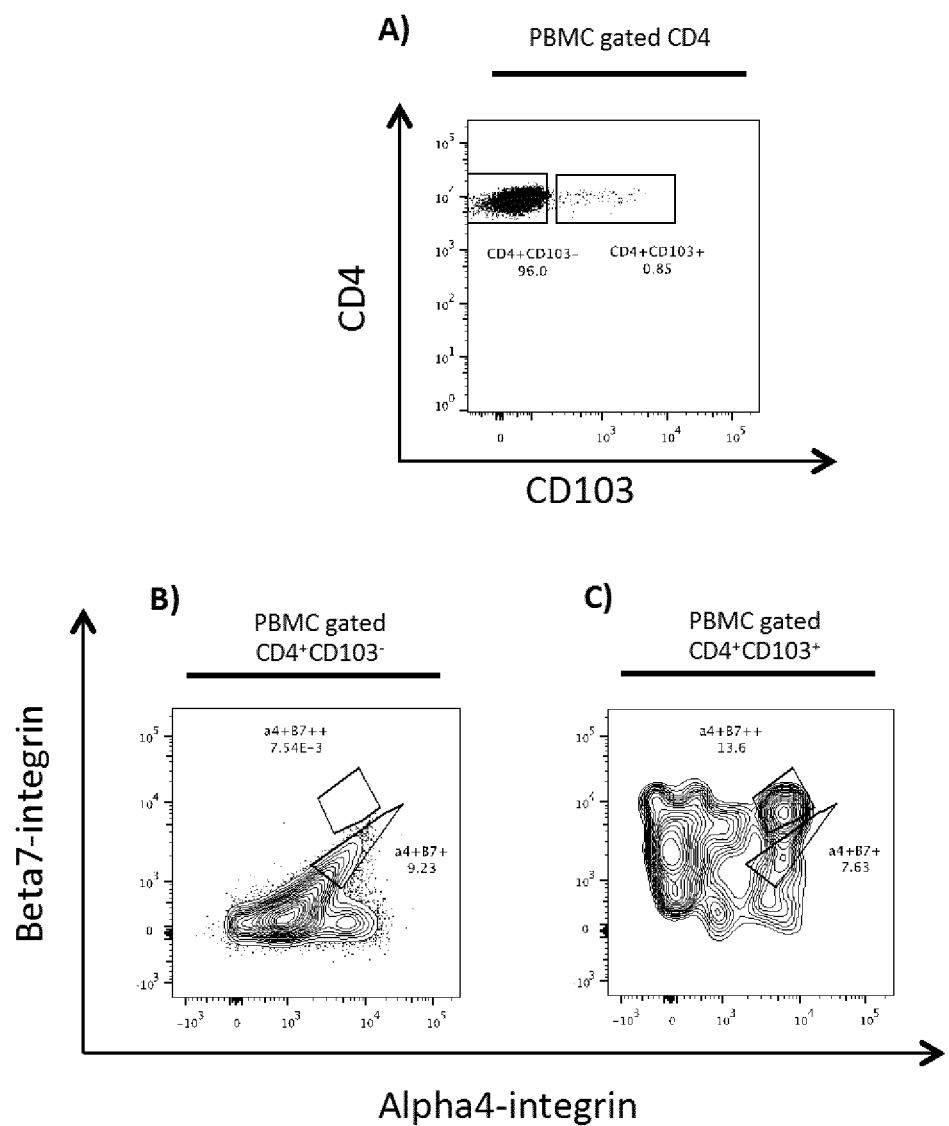

FIG. 26. CD4$^+$CD103$^+$ T-cells in peripheral circulation are highly enriched for α4$^+$β7$^{high}$ expressing T-cells. PBMC recovered from healthy donor blood over ficoll were immediately labelled with indicated antibodies and analysed by flow cytometry. A) Total CD4 lymphocytes expressed as CD4 vs CD103 dot plots. Each gate defining CD4+CD103− and CD4+CD103+ is redisplayed as beta7− vs alpha4− integrin contour plots in B) and C), respectively.

Figure 27:
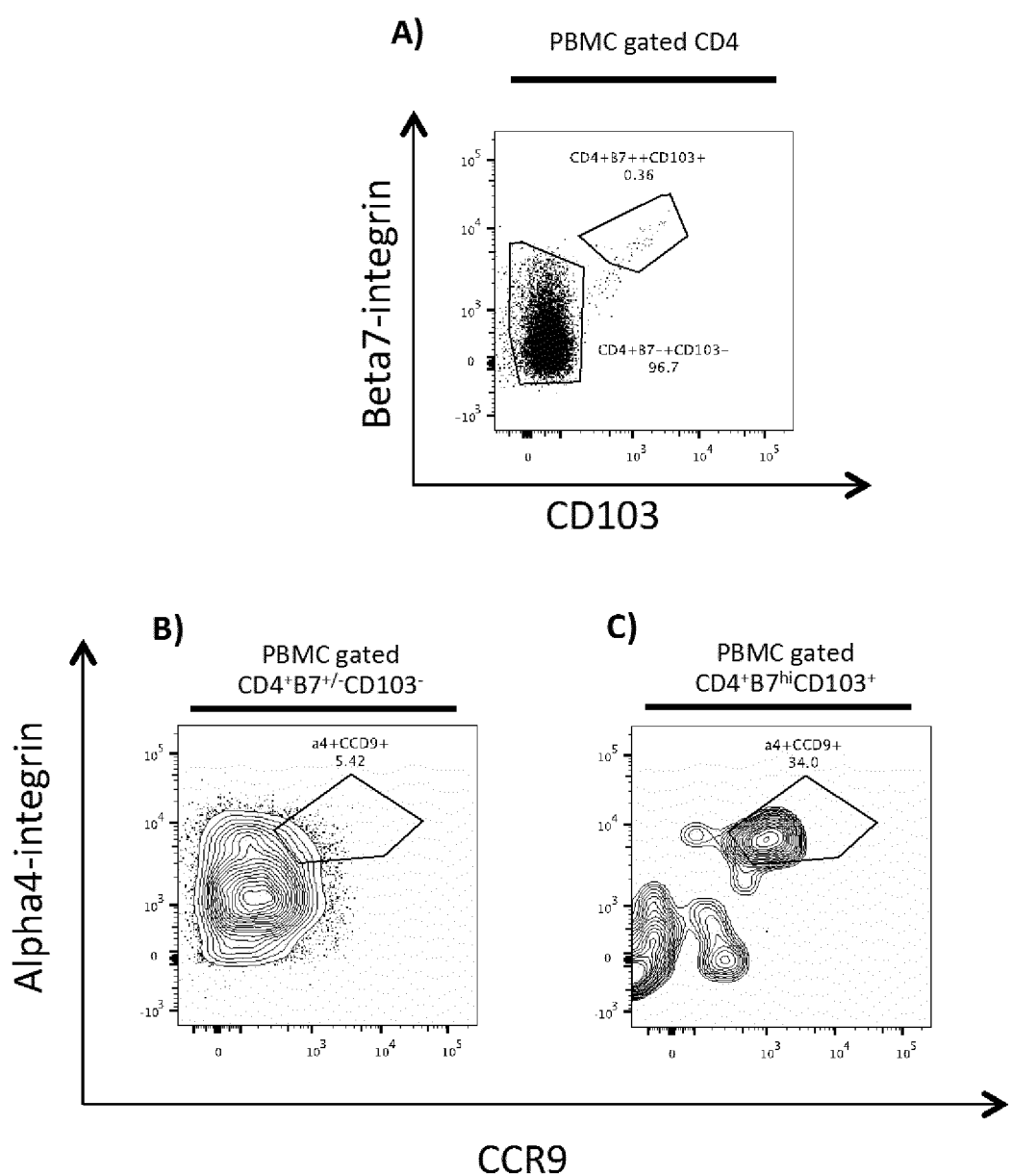

FIG. 27. CD4$^+$β7$^{high}$CD103$^+$ T-cells in peripheral circulation are enriched for α4$^+$CCR9 expressing T-cells. PBMC recovered from healthy donor blood over ficoll were immediately labelled with indicated antibodies and analysed by flow cytometry. A) Total CD4 lymphocytes expressed as beta7-integrin vs CD103 dot plots. Each gate defining beta7+−CD103− and beta7++CD103+ is redisplayed as alpha4− integrin vs CCR9 contour plots in B) and C), respectively.

Figure 28:
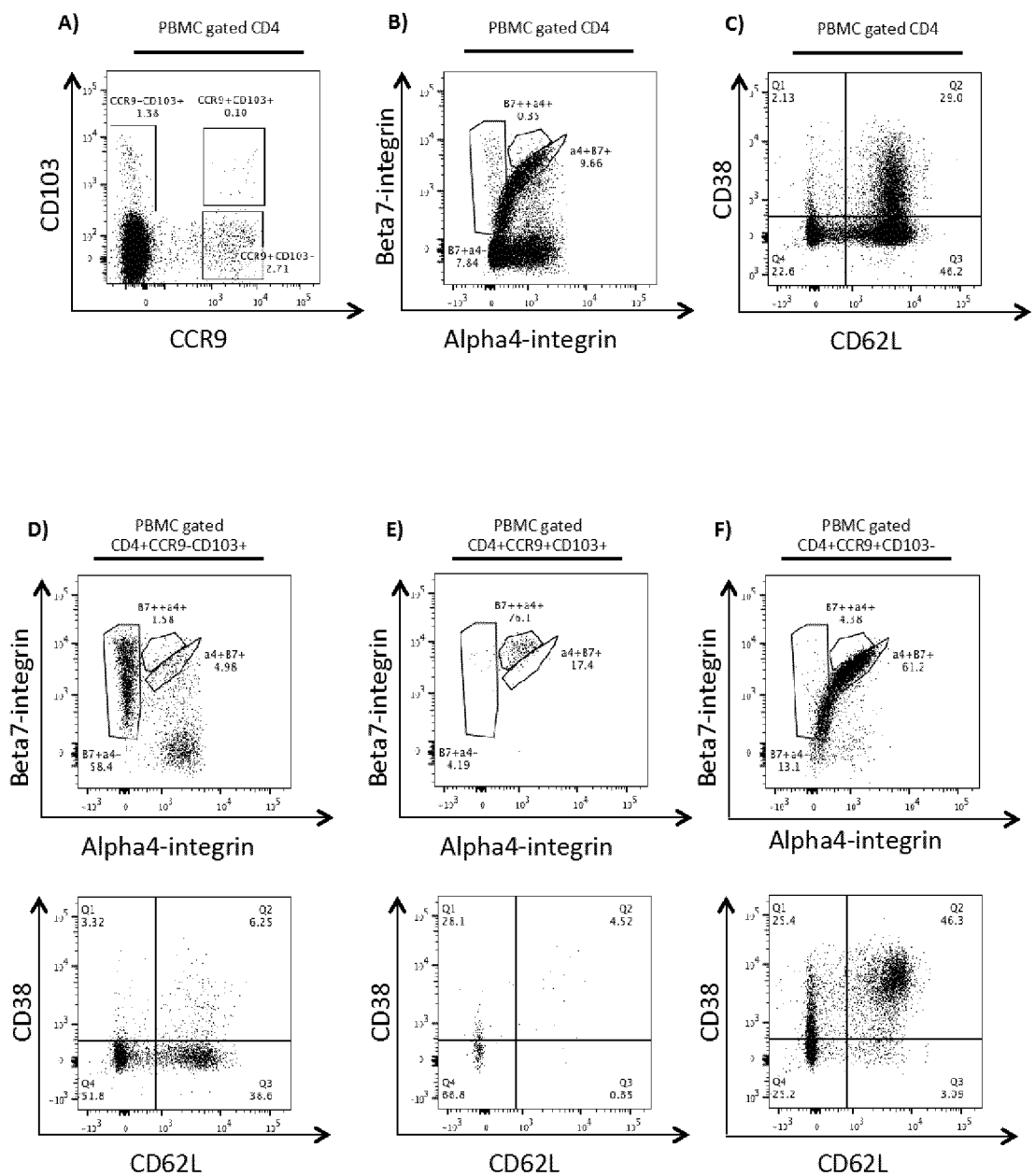

FIG. 28. CD4$^+$α4$^+$β7$^{high}$CD103$^+$CCR9$^+$ T-cells in peripheral circulation contain an enriched proportion of CD38$^+$ CD62L$^-$ mucosal emigrants. PBMC recovered from healthy donor blood over ficoll were immediately labelled with indicated antibodies and analysed by flow cytometry. A) Total CD4 lymphocytes expressed as CD103 vs CCR9 dot plots. B) Total CD4 lymphocytes expressed as B7 vs a4 dot plots. C) Total CD4 lymphocytes expressed as CD38 vs CD62L dot plots. D) to F) gates of single and double positive CD103 and CCR9 cells in A) redisplayed as B7 vs a4 (top panels) and CD38 vs CD62L (bottom panels) dot plots.

Figure 29:
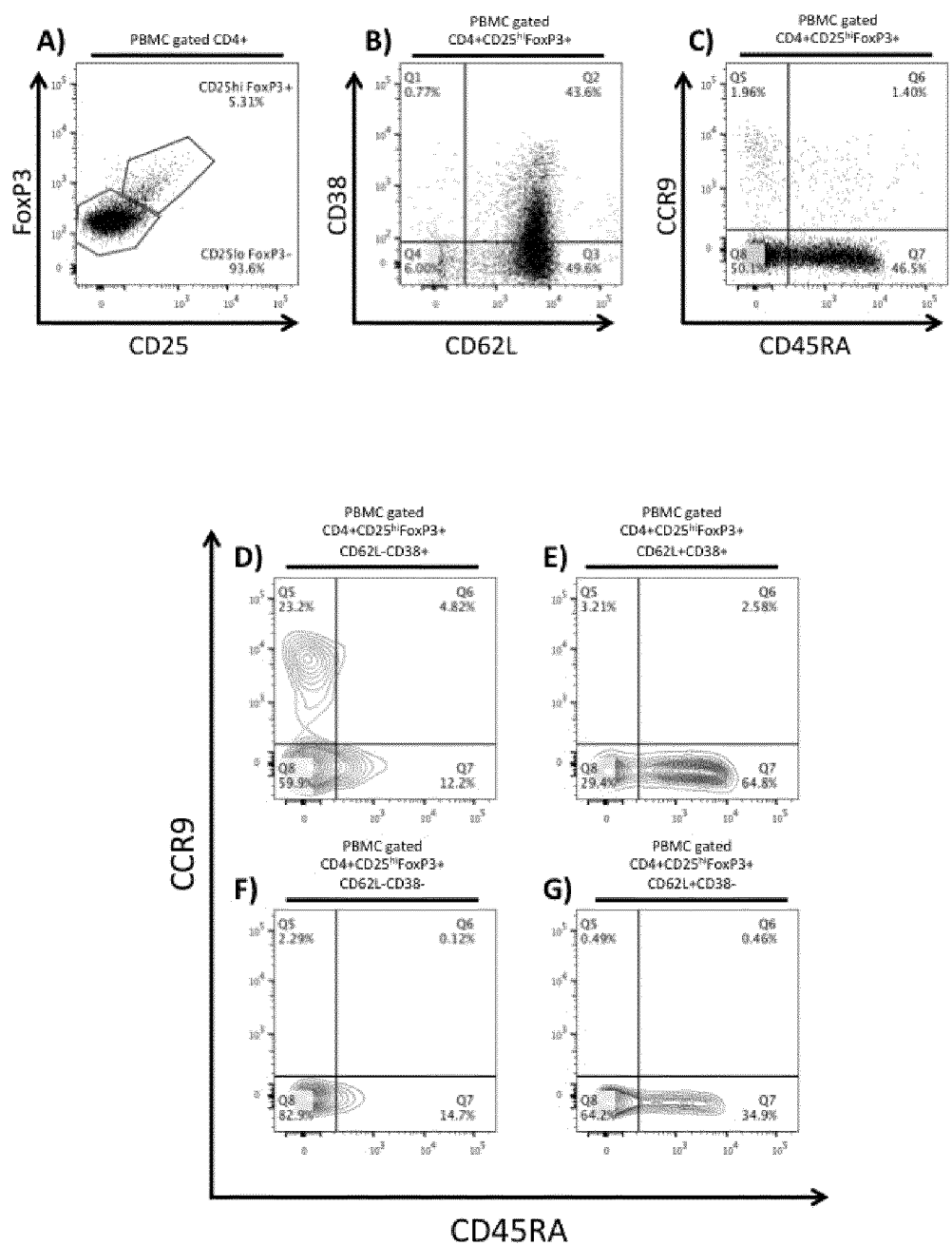

FIG. 29. CD4$^+$CD25$^{hi}$FoxP3$^+$CD38$^+$CD62L$^-$CCR9$^+$ T-cells do not express CD45RA. PBMC recovered from healthy donor blood over ficoll were immediately labelled with indicated antibodies and analysed by flow cytometry. A) Total CD4+ lymphocytes expressed as FoxP3 vs CD25 dot plot. B) and C) display CD4$^+$CD25$^{hi}$FoxP3$^+$ cells as CD38 vs CD62L and CCR9 vs CD45RA dot plots, respectively. D) to G) display CCR9 vs CD45RA contour plots of gated populations from B) as indicated.

Figure 30:
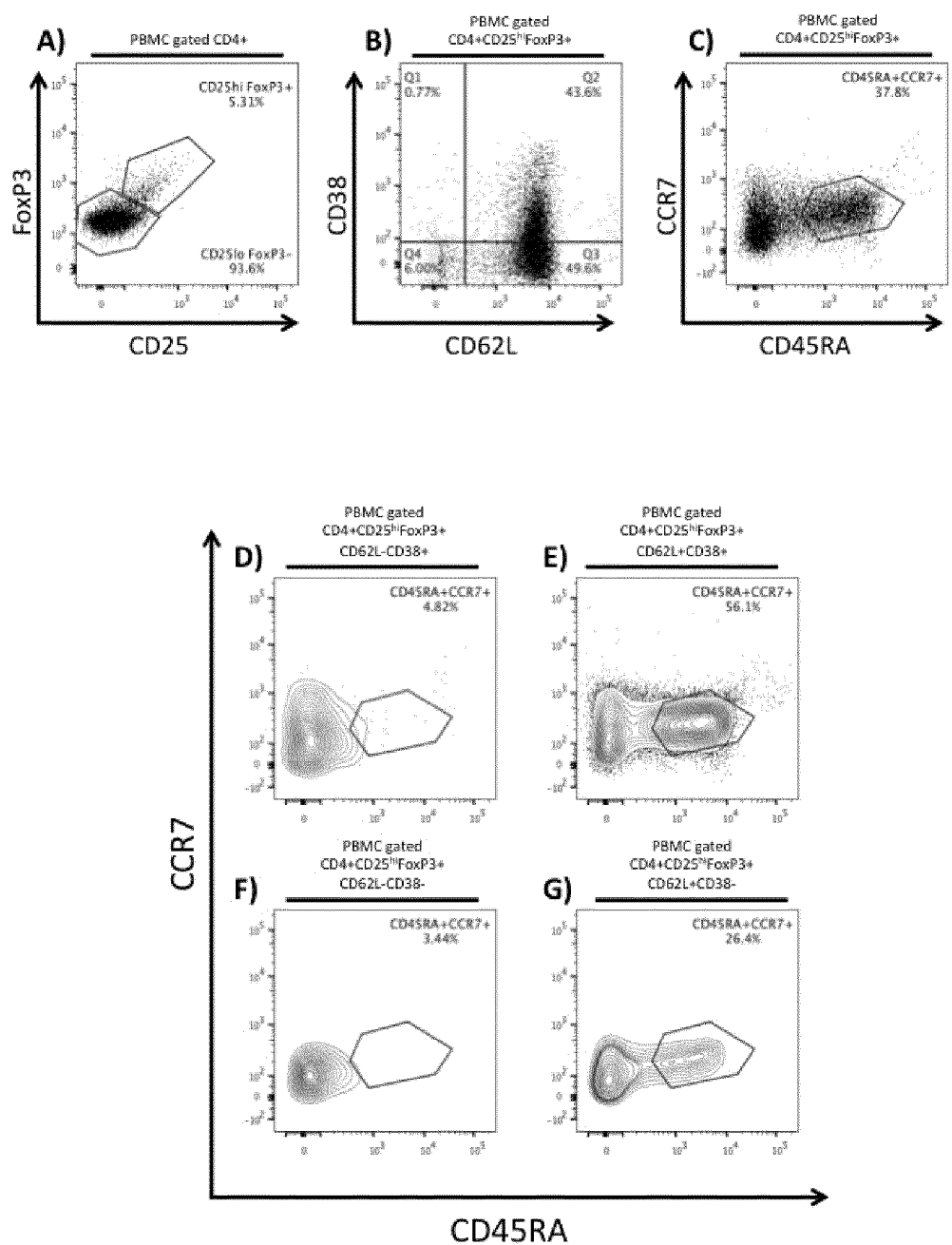

FIG. 30. CD4$^+$CD25$^{hi}$FoxP3$^+$CD38$^+$CD62L$^-$ T-cells do not contain CD45RA/CCR7 double positives but CD4$^+$ CD25$^{hi}$FoxP3$^+$CD62L$^+$ T-cells are enriched for CD45RA/CCR7 double positive nave cells. PBMC recovered from healthy donor blood over ficoll were immediately labelled with indicated antibodies and analysed by flow cytometry. A) Total CD4$^+$ lymphocytes displayed as FoxP3 vs CD25 dot plot. B) and C) display CD4$^+$CD25$^{hi}$FoxP3$^+$ cells as CD38 vs CD62L and CCR7 vs CD45RA dot plots, respectively. D) to G) display CCR7 vs CD45RA contour plots of gated populations from B) as indicated.

FIG. 31. T-cell migratory-type surface markers correlated with CD4$^+$CD62L$^-$CCR9$^+$ mucosal T-cells. PBMC recovered from healthy donor blood over ficoll were immediately labelled with indicated antibodies and analysed by flow cytometry in a high throughput screen. A) Total CD4$^+$ lymphocytes displayed as CD62L vs CCR9 dot plot. B) displays CD4$^+$CD62L$^-$CCR9$^-$ cells as SSC vs β7 contour plot. C) and D) display SSC vs CD195 contour plots of CD4$^+$CD62L$^-$CCR9$^-$β7$^+$ cells and CD4$^+$CD62L$^-$CCR9$^+$ cells, respectively. E) Summary of ranked preferable migratory markers of X$^+$/X$^-$ condition for identification of small bowel tropic T-cells. Markers noted with 'hi' in parenthesis indicate that the population with high expression of the indicated marker is of interest, indicating that both low and negative expression populations may also exist FIG. 32. T-cell migratory-type surface markers correlated with CD4$^+$CD62L$^-$CCR9$^-$β7$^+$ mucosal T-cells. PBMC recovered from healthy donor blood over ficoll were immediately labelled with indicated antibodies and analysed by flow cytometry in a high throughput screen. A) Total CD4$^+$ CD62L$^-$CCR9$^-$ lymphocytes displayed as SSC vs β7 contour plot. B) and C) display SSC vs CD29 contour plots of CD4$^+$CD62L$^-$CCR9$^-$β7$^-$ cells and CD4$^+$CD62L$^-$CCR9$^-$ β7$^+$ cells, respectively. D) Summary of ranked preferable migratory markers of Y$^+$/Y$^-$ condition for identification of mucosal tropic regulatory T-cells. Markers noted with 'hi' in parenthesis indicate that the population with high expression of the indicated marker is of interest, indicating that both low and negative expression populations may also exist.

FIG. 33. T-cell functional-type surface markers correlated with CD4$^+$CD25$^{hi}$CD127$^{lo}$α4$^+$β7$^+$ mucosal T-cells. PBMC recovered from healthy donor blood over ficoll were immediately labelled with indicated antibodies and analysed by flow cytometry in a high throughput screen. A) Total CD4$^+$ α4$^+$β7$^+$ lymphocytes displayed as CD127 vs CD25 dot plot. B) and C) show SSC vs CD39 contour plots of CD4$^+$α4$^+$ β7$^+$CD25$^{lo}$CD127$^{hi}$ cells and CD4$^+$α4$^+$β7$^+$CD25$^{hi}$CD127$^{lo}$ cells, respectively. D) Summary of ranked preferable functional markers of Z$^+$/Z$^-$ condition for identification of regulatory mucosal T-cells. Markers noted with 'hi' in parenthesis indicate that the population with high expression of the indicated marker is of interest, indicating that both low and negative expression populations may also exist.

Figure 34:
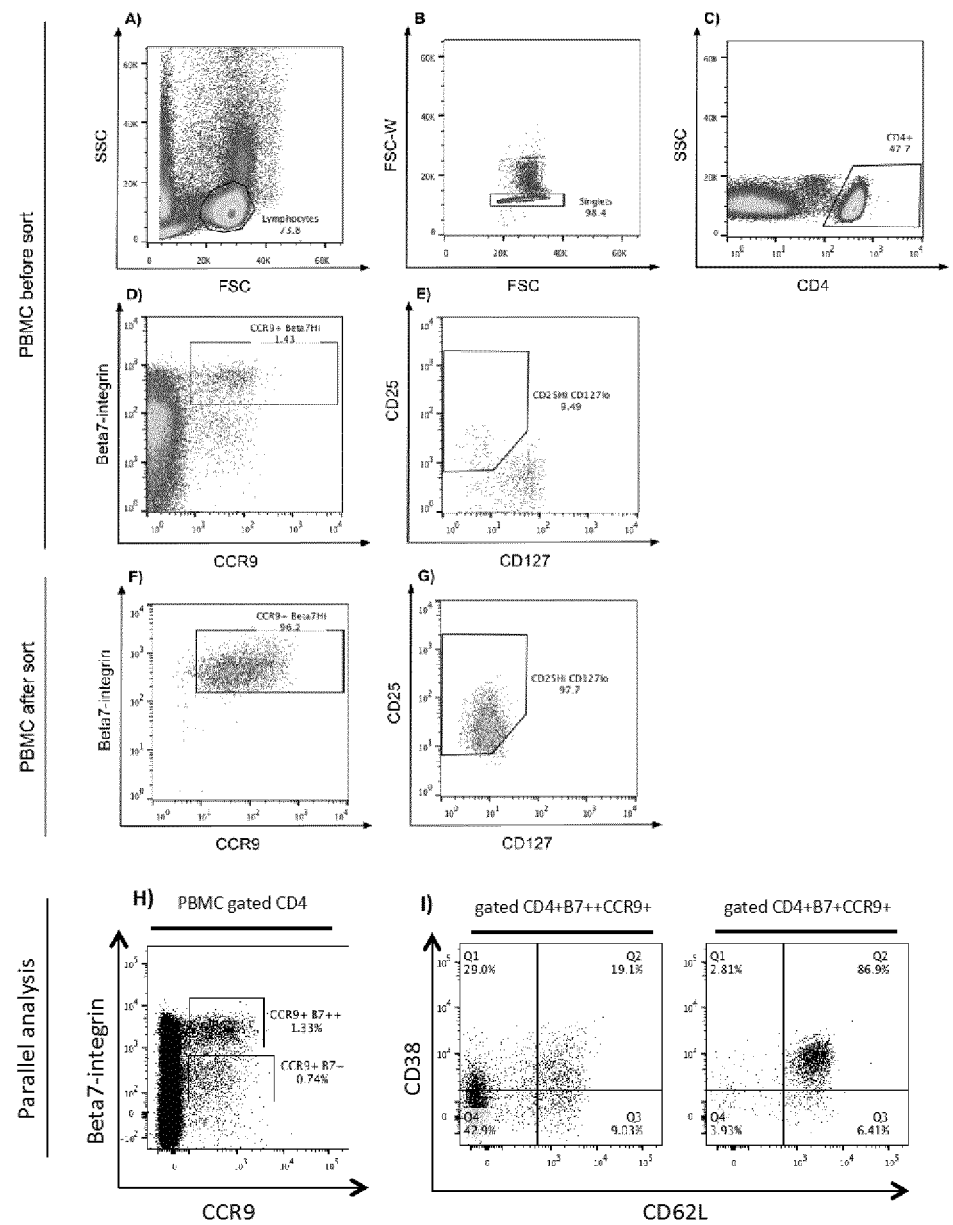

FIG. 34. Purification of a distinct subset of CD4$^+$ CD25$^{hi}$CD127$^{lo}$β7$^{hi}$CCR9$^+$ Tregs from peripheral blood. PBMC recovered from healthy donor blood over ficoll were immediately labelled with indicated antibodies and purified by fluorescent-activated cell sorting (FACS). Pseudo-color plots from A) to C) show lymphocytes gated from total PBMC in A) and subsequent sub-gates for single cells in B) and CD4+ cells in C). Plot D) redisplays total CD4+ lymphocytes as Beta7-integrin vs CCR9. The sub-population Beta7-integrin$^{Hi}$ CCR9$^+$ defined in plot D is re-displayed in plot E) as CD127 vs CD25 to define the subpopulation CD25$^{hi}$CD127$^{lo}$ of T-regs. Plot F) and G) show the enrichment of the rare Beta7-integrin$^{hi}$CCR9$^+$ CD25$^{hi}$CD127$^{lo}$ population of CD4 cells sorted according to the gating strategy outlined in plots A) to E) and re-analyzed by flow cytometry for the degree of sort purity. Panels H) and I) shows a parallel analyses of B7$^{hi}$CCR9$^+$ cells with CD38 vs CD62L dotplots of panel I) being the daughters of populations gated in panel H).

Figure 35:
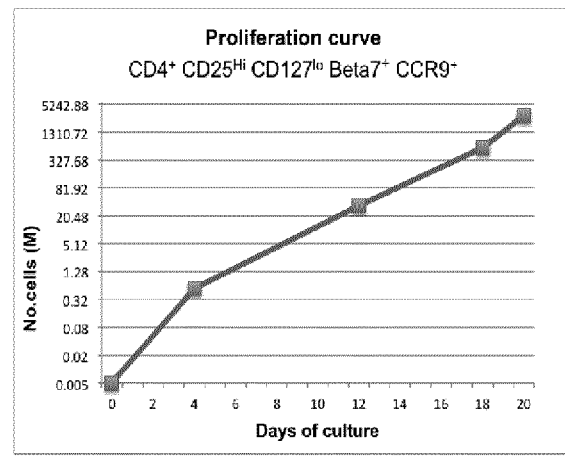

FIG. 35. Expansion of sorted CD4$^+$ CD25$^{hi}$CD127$^{lo}$β7$^{hi}$CCR9$^+$ Tregs in culture. The subset of CD4$^+$CD25$^{hi}$CD127$^{lo}$β7$^{hi}$CCR9$^+$ T-cell purified by FACS was cultured over several days. The proliferation curve displays the expansion of a starting pool of 5000 sorted CD4$^+$CD25$^{hi}$CD127$^{lo}$CCR9$^+$Beta7$^{hi}$ T-cell reaching almost 3 billions cells over 20 days of culture.

Figure 36:
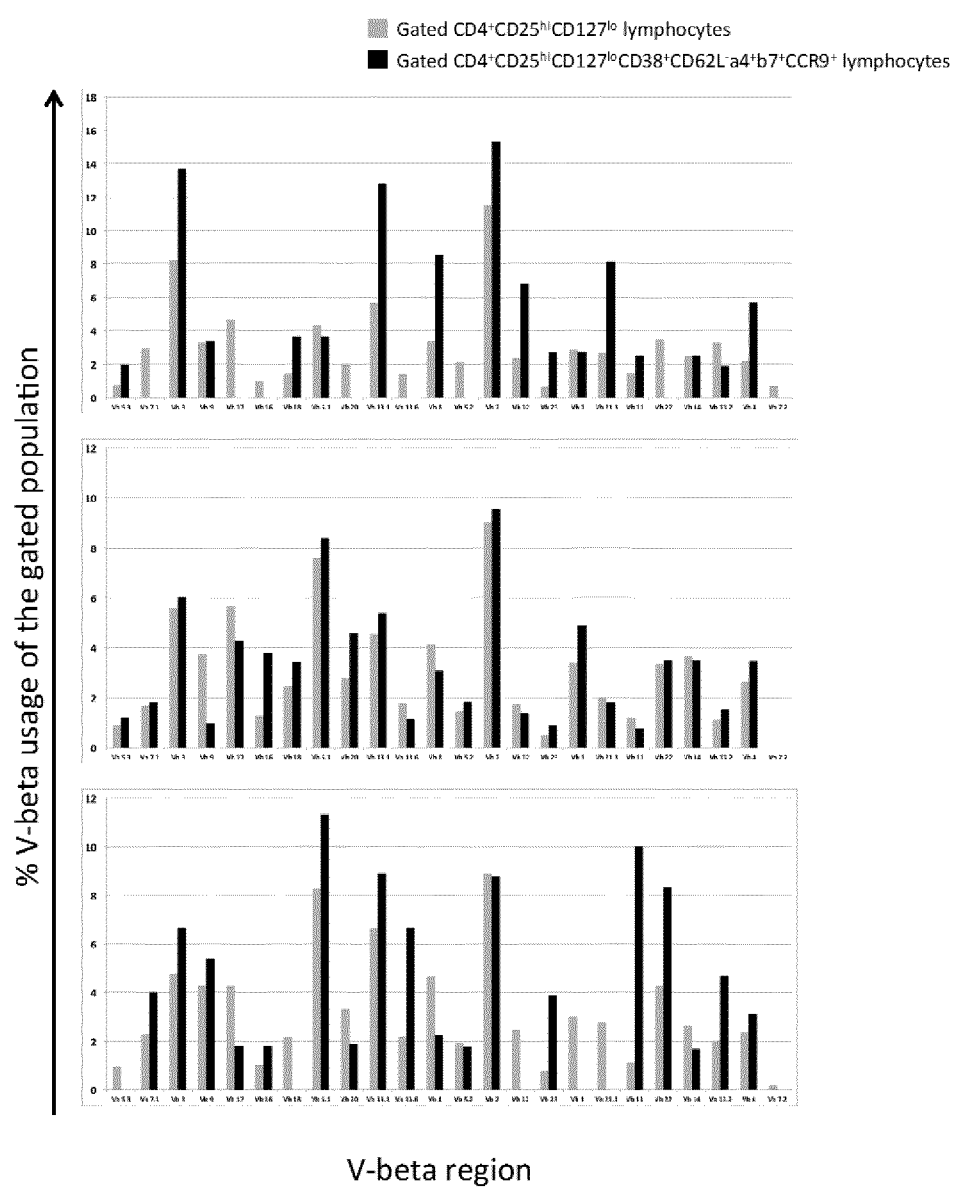

FIG. 36. Peripheral CD4$^+$CD25$^{hi}$CD127$^{lo}$CD62L$^-$CD38$^+$α4$^+$β7$^+$CCR9$^+$ T-cells have skewed Vβ usage compared to CD4$^+$CD25$^{hi}$CD127$^{lo}$ cells. PBMC recovered from blood of three healthy donors over ficoll were immediately labelled with CD4, CD25, CD127, CD38, CD62L, CD49d, β7 and CCR9 antibodies in addition to panels of Vβ-specific antibodies and analysed by flow cytometry. Coverage of donor C12 (top panel) was CD4$^+$CD25$^{hi}$CD127$^{lo}$ 75% and CD4$^+$ CD25$^{hi}$CD127$^{lo}$CD62L$^-$CD38$^+$α4$^+$β7$^+$CCR9$^+$ 95%. Coverage of donor C6 (middle panel) was CD4$^+$CD25$^{hi}$CD127$^{lo}$ 72% and CD4$^+$CD25$^{hi}$CD127$^{lo}$CD62L$^-$CD38$^+$α4$^+$β7$^+$CCR9$^+$ 77%. Coverage of donor C26 (bottom panel) was CD4$^+$CD25$^{hi}$CD127$^{lo}$ 77% and CD4$^+$ CD25$^{hi}$CD127$^{lo}$CD62L$^-$ CD38$^+$α4$^+$β7$^+$CCR9$^+$ 93%.

Based on experiments, the inventors have made the following observations:

CD4$^+$ Tregs in human small bowel tissues and in peripheral blood preferentially carry small bowel-tropic markers when compared to Teff counterparts. The numbers of CCR9-expressing Tregs in the peripheral blood and inflamed tissues of CD patients are significantly diminished, though the total number of mucosal-tropic Tregs is increased. This apparent defect in small bowel homing related to CCR9 expression deficiency among T-cells can be correlated to a numerical deficiency of CD103$^+$ DC in inflamed patient MLN. Mucosal emigrant and mucosal tropic Tregs as defined by the presented marker sets are proposed therapeutic candidates for the management of CD and other IBDs. Disease-draining MLN were used as an enriched starting source of these cells and may be purified and expanded to high numbers in vitro. Cells of the various identified compositions can be non-invasively recovered from peripheral blood preparations and expanded in vitro. In general, expanded cells retain suppressive capacity with regard to suppressing proliferation of autologous Teffs. These cells may then be repatterned to express correct homing receptors with addition of specific recombinant protein and chemical stimuli. Preparing targeted Treg subpopulations in this manner is proposed to restrict TCR clonal diversity to clonotypes specific for tissue- and thus disease-associated antigens.

Firstly the inventors addressed whether CD4$^+$FOXP3$^+$ T$_{regs}$ in the human gut displayed higher CCR9 expression than CD4$^+$FOXP3$^-$ counterparts. FIG. 1A shows flow cytometry analyses of single cell suspensions prepared from relatively proximal healthy tissue of the small intestine of a representative CD patient. CD4$^+$FOXP3$^+$ cells show greater CCR9 expression relative to CD4$^+$FOXP3$^-$ Teffs in both small and large bowel LP (mucosal lamina propria). CCR9 marking of CD4$^+$FOXP3$^+$ cells is greater overall in the small bowel LP, consistent with the regional differences in CCR9 marking reported previously (Papadakis et al. Gastroenterology 2001, 121, pp 246-254). The CD4$^+$FOXP3$^+$ population also carried a greater proportion of cells with integrin β7$^{hi}$ phenotype, particularly in the small bowel LP. Cells with a CD4$^+$FOXP3$^+$β7$^{hi}$ phenotype almost exclusively expressed CCR9 (FIG. 1B). The preferential marking of CD4$^+$FOXP3$^+$ cells was also reflected in the mesenteric lymph nodes (MLNs) draining the small bowel (FIG. 2). Tregs more stringently gated on CD4$^+$CD127$^{lo}$CD25$^{hi}$FOXP3$^+$ phenotype(9), similarly have higher CCR9 expression than Teffs with CD4$^+$CD127$^{hi}$CD25$^{lo}$FOXP3$^-$ phenotype in small bowel MLN (FIG. 3); and in peripheral blood after further analytical enrichment by gating on β7$^+$ (FIG. 4). These results are consistent with a stronger CCR9-dependent small-bowel tropism of Tregs compared to Teff counterparts from human gut. Moreover, direct parallels can be drawn with recent results regarding CCR9 expression on mouse T-cells, and the CCR9-dependency of oral tolerance (Wermers et al. Gastroenterology 2011, 140 (5), pp. 526-1535, and Cassani et al. Gastroenterology 2011, 141 pp 2109-2118).

These observations reveal some interesting features of the co-expression of markers in the small and large bowel mucosal lamina propria (LP), and by association the MLN draining these tissues. Specifically, the presence of a β7-high population dominantly in small bowel is suggestive of the presence of and additional integrin pairing within this small bowel population. At the time it was speculated that this could be the αEβ7 pairing, which is addressed and confirmed herein.

Strikingly, the β7-high population in LP has the almost exclusive CCR9 marking in the healthy tissue analysed here. Thus β7-high and its integrin co-markers represent a proxy CCR9 marker at least in these tissues. This has implications for the understanding of fundamental migration mechanisms of T-cells in humans, but also provides analytical and therapeutic possibilities as mentioned herein.

Mucosal-Educated FOXP3$^+$ Tregs in Peripheral Circulation Carry Higher CCR9 Marking than FOXP3$^-$ Teffs and CD Patients have Diminished Overall CCR9 Marking on Mucosal-Educated T-Cells The inventors excluded that preferential CCR9 marking was only occurring on resident Tregs in the LP and MLN, by investigating CCR9 expression of both mucosal-educated and mucosal-tropic Tregs in peripheral blood. A CD38$^+$CD62L$^-$ phenotype was used to enrich T-cells educated within the intestinal mucosa in flow cytometric analysis of peripheral blood mononuclear cells (PBMCs) from healthy controls (HC) and CD patients with small bowel disease. Observations confirmed the enrichment of β7 and CCR9 marking on CD38$^+$CD62L$^-$ T-cells, and showed that the CD38$^+$CD62L$^-$β7$^+$ sub-population is further enriched for CCR9 positivity (FIG. 5A). Furthermore, T-cells of CD38$^+$CD62L$^-$ phenotype predominate in both the human small and large bowel LP (FIG. 6). CD4$^+$FOXP3$^+$ Treg numbers in circulation are not significantly diminished in CD patients compared to healthy controls as previously reported, although trend in this direction (FIG. 5B). There is no significant difference in the total number of mucosal-educated CD4$^+$CD38$^+$CD62L$^-$ Tregs between CD patients and healthy controls, while overall CCR9 positivity in this sub-population is strikingly reduced in CD patients (FIG. 5C). Preferential CCR9 marking of CD4$^+$FOXP3$^+$ T$_{regs}$ over CD4$^+$FOXP3$^-$ effectors is observed in CD38$^+$CD62L$^-$β7$^+$ mucosal emigrants present in peripheral circulation of healthy controls (HC). This preferential CCR9 marking of Tregs is maintained in CD patients, however the overall numbers of CCR9+ Tregs and non-Tregs are diminished in the mucosal-educated sub-population relative to healthy controls (FIG. 50).

There are two intriguing aspects to this directed analysis of peripheral recent mucosal emigrants. The overall numbers of Tregs in peripheral circulation is trending towards a deficiency in CD compared to healthy controls. However, when we look only at the recent emigrants that are also likely destined for recirculation to mucosa (CD38+CD62L− β7), then we actually observe a trend towards increased numbers of Tregs. In addition these recent emigrant and recirculating T-cells have a marked reduction in CCR9 expression. Taken together, these data suggest that CD is not a disease defined by a deficiency of Tregs per se, but a deficiency in their ability to recirculate to the small bowel. This could also be construed as a strong retention of CCR9-carrying T-cells in the inflamed bowel of CD patients.

It is possible that the Treg population under the strong inflammatory conditions in the inflamed lamina propria is undergoing atrophy. The general inflammatory state would also draw more nave Tregs from peripheral circulation, decreasing the apparent incidence of total Tregs in the periphery. It appears that T-cells can still be exported from the inflamed mucosa-associated lymphoid tissues (i.e. MLN), though lack the important chemokine receptor trigger (CCR9) to facilitate re-import to the inflamed mucosa.

CD4+α4+β7+ Mucosal-Tropic FOXP3+ Tregs in Peripheral Circulation Carry Higher CCR9 Marking than FOXP3− $T_{\it effs}$ and CD Patients have Diminished CCR9 Marking on Mucosal-Tropic T-Cells In addition to investigating CCR9 expression on mucosal-educated T-cells having emigrated to peripheral circulation, the total pool of mucosal-tropic T-cells in peripheral blood was examined through analytical enrichment of α4+β7+ expressing CD4+ T-cells. We show that T-cells with this α4+β7+ phenotype in peripheral circulation are highly enriched for CCR9 positivity (FIG. 7A-B); indeed on average greater than 75% of all CCR9+ cells in peripheral circulation carry α4+β7+ expression (FIG. 8). Surprisingly, even though the total number of CD4+α4+β7+ T-cells is similar in healthy controls and CD patients (FIG. 9), CD4+ FOXP3+ Treg numbers are relatively increased in this mucosal-tropic subpopulation in the peripheral blood of CD patients (FIG. 7C). The CD4+FOXP3+ Tregs in the peripheral mucosal-tropic population carry significantly higher CCR9 marking when compared to CD4+FOXP3− Teffs in both healthy controls and CD patients, while overall CCR9 positivity is diminished in CD patients (FIG. 7D). These results strongly suggest that there are relatively more Tregs in the peripheral circulation of CD patients with the capacity to traffic to mucosal tissues, but these mucosal-tropic cells lack small-bowel specificity due to reduced levels of CCR9 expression. Explanations may be either a defect in CCR9 imprinting in the LP/MLN of CD patients, or a strong migration of CCR9-expressing T-cell subclasses to the inflamed small bowel mucosa in CD patients.

This data for the total pool of mucosal-tropic T-cells is in agreement with the data above regarding recent mucosal emigrants, revealing a striking defect in CCR9 expression on Tregs from CD patients. More interestingly, while the total numbers of mucosal-tropic T-cells are similar, the percentage of Tregs is actually higher. This is in contrast with the proportion of Tregs among all CD4 cells in circulation, and to the concept that CD is a disease defined by a deficiency in Treg populations. This data further supports the notion that CD is defined by Tregs being unable to recirculate to the small bowel mucosa and indeed there is an apparent excess of mucosal-targeted Tregs available.

Treg Purification

Two different purification strategies were used to purify Treg populations from mesenteric lymph nodes of patients, a full MACS enrichment, or a MACS pre-enrichment followed by FACS purification. The recovered populations are highly enriched in cells with the desired characteristics. That is, of character CD4+CD25$^{hi}$CD127$^{lo}$CD62L−CD38+α4+ β7+CCR9+, simply owing to their MLN origin (see FIGS. 1, 2, 3 and 6). Both of these enrichment and purification types were used to study Treg cell growth, homing receptor pattern stability and dynamics, and functionality, ex vivo. The enrichment/purification methods used in the present context are for illustrative purposes due to limiting yields for larger scale preparative experiments from peripheral blood. Purification of target populations from peripheral blood is presented below. Other suitable methods enrichment and purification may also be applied.

MACS 2-Step Enrichment of Tregs from MLN

For research-graded preparations of Tregs from MLN and other tissues Miltenyi MACS approaches have primarily been used. FIG. 10 presents purification data using a Regulatory T Cell Isolation Kit II and an autoMACSpro instrument. This procedure uses a negative affinity selection on non-CD4-expressing and CD127-expressing cells. A subsequent positive affinity selection purifies the final CD4+ CD127$^{lo}$CD25$^{hi}$ population based on CD25 labelling.

MACS Enrichment and FACS Purification of Tregs from MLN

A second means of Treg purification from MLN material is a 2-step approach using Miltenyi MACS enrichment of total CD4+ cells, then FACS purification on various parameters including CD25 and CD127 (FIG. 11). The pre-enrichment was routinely conducted due to limitations in both FACS instrumentation and biological reagent resources at the time this work was conducted.

Treg Expansion

The expansion of Tcells ex vivo utilises standardised methods that rely on stimulation of three core T-cell activating inputs. The minimal signals that a Tcell requires to activate and proliferate are stimulation of the TCR (aka CD3), co-stimulation via CD28 receptor, and a secondary mitogenic stimulation via Interleukin-2 receptor (IL2R).

Standardized approaches use antibodies to stimulate both CD3 and CD28. Recombinant IL2 is used for the mitogenic input. Various modifications of the general method are used with regard to the vehicle, dosage and duration of CD3 and CD28 stimulation, in addition to the subsequent IL2 input. A general method is described in detail in the methods section, but it is believed that the T-cells can be expanded by generic methods. FIG. 12 shows typical ex vivo expansion curve of MACS-purified Tregs from patient MLN, where approximately 120- to 150-fold population expansion is achieved over 18 days of culture. Rapamycin was included in selected cultures to assess impact on Treg growth and culture stability. Rapamycin is routinely used to limit the growth of Teff subclasses in human Treg cultures, and thus polarise to a Treg phenotype over time. Three different Rapamycin dosing strategies were used here, where it was present for the entire 18 days, or just the first 8 or 15 days of expansion. In our hands Rapamycin strongly inhibited Treg growth (FIG. 12), and did not promote Treg characteristic stability (FIG. 13). The reason for this may be the MLN source of the cells, where we expect a bulk to be induced/experience Tregs, and not nave Treg precursors isolated from peripheral circulation as investigated by others. In addition to the basic CD25-FOXP3 parameters presented in FIG. 13, we monitored CD127 levels, which mirrored the CD25-FOXP3 population. Moreover, we expanded and manipulated Teff populations in parallel to ensure accurate comparison of what were likely to be stable Treg cells (not shown). These complimentary analyses suggest that the CD25-FOXP3 expression was indeed indicative of a true Treg phenotype, and not a sole result of strong activating stimuli.

Despite a natural enrichment for cells of mucosal emigrant and mucosal-tropic characteristics in our MACS-enriched Treg cultures (refer FIGS. 2 to 8), we found that after 18 days of expansion the resultant T-regs were almost devoid of small-bowel tropic homing receptor expression (FIG. 14). In vivo, these receptors are imprinted by tolerogenic stimuli provided directly by DCs. In the absence of such inputs to maintain receptor expression, it is clear why we observe little or no receptor expression after 18 days of culture This absence of gut-tropic homing receptors presents a caveat for our method of therapy. Namely, we select the Treg populations based on their inherent homing characteristics, however, once expanded in vitro by generic methods, they lack the qualities required to traffic back to the diseased bowel on re-infusion to the patient. It has been established, mainly using mouse tissues, that T-cells can be forced to express small-bowel homing receptors including α4– and β7– intergrins, and CCR9.

In the following a simple set of observations outlines the considerations and method behind homing receptor 'repatterning' after expansion.

Treg Receptor Re-Patterning

To determine the culture parameters required for receptor repatterning on ex vivo expanded Tregs, we first used short term (4 days) growth of Treg cells in the presence of absence of the tolerogenic stimuli ATRA (all-trans retinoic acid, also referred to as RA in some figures), and transforming growth factor-beta (TGF or TGF-beta). In addition, we assessed the impact of Rapamycin on the expression of homing receptors of the short-term, and on the tolerogenic induction of homing receptors.

FIG. 15a shows 4-day expansions of MACS-enriched and FACS-purified Tregs in the presence of the indicated stimuli. The top left panel shows cells activated and grown in a generic manner without further stimulation. These cells retain significant levels of β7– intergrin and CCR9 co-expression. Strikingly, the addition of Rapamycin (RAPA) strongly attenuates the expression of β7– intergrin and CCR9 (bottom left panel). Addition of TGF/ATRA to these cultures strongly induces β7– intergrin, but not CCR9 (top right). Rapamycin attenuates CCR9 expression, but not β7– intergrin (bottom right).

FIG. 15b demonstrates that increasing concentrations of TGF on a background of ATRA stimulation can almost completely polarise Tregs towards a β7$^+$CCR9$^+$ phenotype. Rapamycin addition almost completely abrogates CCR9 positivity in this system.

These experiments establish the basic parameters of receptor repatterning, in as much that we now appreciate that any such approach should be done in the absence or Rapamycin, and with minimal ATRA and TGF stimuli. FIG. 16 shows day-18 expanded MACS-enriched Tregs that have been stimulated for a further 6 days with combinations of three tolerogenic stimuli. These stimuli were part of a much larger titration, and are presented in this focused context for clarity. FIG. 16a shows that the lack of α4β7 expression on Tregs after 18-days of expansion (refer FIG. 14) persists after 6 further days of culture without additional stimuli. ATRA alone is sufficient to induce α4β7 expression in a dose-dependent manner (FIG. 16c,d). IL10 is sufficient to weakly induce β7– but not α4– integrin expression (FIG. 16e), an effect that appears to be anergised by TGF (FIG. 16g). The most effective stimuli for α4β7 induction were found to be low doses ATRA in combination with IL10, or IL10 and TGF (FIG. 16h, i).

The expression of CCR9 on these stimulated cells was further assessed in parallel, which is displayed against β7 expression in FIG. 17. Several important interactions of the stimuli can be observed when considered in context with the above α4β7 data. First, while TGF alone is insufficient to induce α4β7 expression (FIG. 16b), it is a moderately effective inducer of CCR9 expression at the dosage presented (FIG. 17b). While IL10 is a strong inducer of CCR9 expression ((FIG. 17e), TGF and IL10 appear to have an anergistic effect when provided as co-stimuli (FIG. 17g). ATRA alone is a moderate inducer of CCR9 expression (FIG. 17c,d), an effect that may be marginally enhanced in combination with IL10 (FIG. 17h). However, all three tolerogenic stimuli in combination have a strong polarising effect on CCR9 expression, while maintaining a correct α4β7 pattern (FIG. 17i) and (FIG. 16i).

Overall, conditions were established with which to 'repattern' the correct α4$^+$β7$^+$CCR9$^+$ homing characteristics on ex vivo expanded Tregs. A combination of low-dose ATRA, TGF and IL10 is sufficient to achieve correct homing receptor patterns with acceptable efficiency.

Treg Functionality

The standard manner in which to test the immunosuppressive functionality of Tregs in vitro is a mixed culture assay. Part of Treg immunosuppressive function is to suppress Teff cell division, we thus measure the degree of Teff cell division in the presence of Treg cells. In our setup we used partially purified Teffs from MLN to test the functionality of ex vivo expanded Tregs from the same patient. Teffs are labeled with carboxyfluorescein succinimidyl ester (CFSE), which is a strongly fluorescent compound that is taken up by the Teff cells. Rapid crossing of the plasma membrane is facilitated by the succinimidyl group, which is subsequently cleaved by intrinsic cellular esterase activity, ensuring retention of the fluorescent carboxyfluorescein in the cell. On cell division, the diffuse carboxyfluorescein is partitioned approximately equally between the two resulting cells. Therefore, one can monitor the cell division of Teff cells in vitro in the presence of (unlabeled) Tregs by monitoring step-wise decrease in Teff fluorescence intensity.

FIG. 18 shows the suppression of freshly purified Teff cells by 18-day expanded autologous Tregs. This demonstrates the suppressive capacity of expanded Treg cells in this system.

Mucosal Emigrant and Homing Markers on Small Bowel Tregs in Inflamed CD Patient Tissues The experimental data presented above regarding purification and expansion of Tregs utilised disease-draining SLN as Treg source material. It is reasoned that SLN will be highly enriched in Tregs with relevant TCR clonotypes, considering their physical disease and/or tissue association. Moreover, SLN and MLN in general will be highly enriched for the tropic and emigrant populations that are of general interest for therapeutic purposes, with their observed deficiencies in peripheral blood. While the SLN are indeed highly enriched for these populations when compared to the peripheral blood compartment, close analysis of patient material provides further insights into the observed peripheral deficiency of CCR9-expressing Tregs.

FIG. 19 shows the contour plots of CD38 vs CD62L of total CD4+FOXP3−CD25lo Teffs (left panels) and CD4+FOXP3+CD25hi Tregs (right panels) recovered from resected tissues of a representative CD patient with ileocaecal disease. Normal MLN in the surgical field, two SLN (1 and 2), inflamed lamina propria (LP) and normal LP is presented from top to bottom. When observing both Tregs and Teffs from normal MLN one can see the expected CD38 positivity and CD62L negativity that correlates with mucosal emigrant populations. This population is more strongly represented in the Treg cells. In both SLNs analysed, the proportion of CD62L+ cells, that is likely to represent direct MLN immigrants from peripheral circulation, is notably increased in both Treg and Teff populations. This may either be due to increased direct immigration to the SLNs compared to healthy MLN, or relatively diminished trafficking of cells from the LP to the SLN. In the four bottommost panels we can observe significant CD62L+ cell numbers in the inflamed LP, but not adjacent healthy tissue. Again, this could reflect a strong and aberrant immigration of cells from circulation, and/or a poor patterning of correct receptors of the T-cells within the LP.

To test whether correct patterning was being achieved on T-cells in inflamed and adjacent healthy CD tissue, CD103 and CCR9 expression was assessed. FIG. 20 shows CD103 vs CCR9 contour plots of total CD4+FOXP3−CD25lo Teffs (left panels) and CD4+FOXP3+CD25hi Tregs (right panels) recovered from resected tissues of a representative CD patient with ileocaecal disease from tissues as above. In normal MLN one can immediately observe the fundamental difference between Teffs (left) and Tregs (right), in that Tregs in the MLN carry very high levels of CD103 and CCR9 and Teffs do not. This could indicate that Tregs are more attuned to trafficking from LP to MLN, and/or they are more likely to be patterned in this way by MLN DCs. The latter is consistent with the tolerogenic function of CD103$^+$ DCs that pattern both CCR9 and CD103 expression. The second striking contrast that may be observed here is the complete loss of both CD103 and CCR9 expression on cells in disease-draining SLN. Moreover, a similar though less dramatic decrease in CD103 and CCR9 expression can be observed in the inflamed LP compared to the healthy tissue. Interestingly, it is the Teff cells that are most strongly expressing CD103 and CCR9 in the normal LP, not the Tregs as in the normal MLN. This may indicate that Teffs are more likely to be retained in the LP than the Tregs, and thus express high levels of the retention integrin CD103. This is consistent overall with the balance of Tregs and Teffs in these two compartments.

To ensure that the observed loss of CD103 and CCR9 expression was not simply due to the dilution of these cells by immigrants from circulation (see FIG. 19), CD38$^+$CD62L$^-$ Tregs were analysed in the same compartments as FIG. 20. FIG. 21 shows a similar analysis of Tregs as in FIG. 20, though a further analytical enrichment of CD38$^+$CD62L$^-$ was used. These data demonstrate that there appears to be a deficiency in CD103 and CCR9 expression on Tregs in the inflamed tissues, despite expression of a mucosal phenotype (CD38$^+$CD62L$^-$). One can also note the relative enrichment in the expression of CD103 and CCR9 (FIG. 21) when compared to the right hand panels of FIG. 20.

The data presented above collectively suggest a defect in the CD103 and CCR9 patterning of T-cells within inflamed tissues of CD patients. The DC subset that is responsible for patterning this receptor expression on T-cells are known to be a CD103+ DC subset. The possibility of a numerical deficiency in this CD103+ DC population was tested as a possible cause of CCR9 and CD103 deficiency. FIG. 22 shows analysis of CD45$^+$CD11c$^{hi}$CD80$^+$HLA-DR$^{hi}$CD103$^+$ DC in the healthy MLN and disease-draining SLN of a CD patient. Strikingly, there is huge numerical deficiency in the CD103+ subset of HLA-DR$^{hi}$DC cells in the SLN. Sufficient cell numbers could not be recovered for a reliable analysis of inflamed and normal LP from this patient. However, limited analyses show a similar trend (not shown).

Identification of Mucosal Emigrant and Small Bowel Tropic Tregs in Peripheral Blood Aside from the obvious practical limitations of harvesting Tcell material from SLN for therapeutic applications, and the strong CCR9 expression defect observed in some patients even within inflamed tissue, the recovery of mucosal emigrant and small bowel tropic Tcells (Tregs?) directly from peripheral blood is attractive. In FIGS. 5 and 7, these populations were treated somewhat separately. While mucosal emigrants were defined as CD38$^+$CD62L$^-$ β7$^+$, this does not fully embody a fully pure candidate for sorting of this target population from peripheral blood. FIG. 23a shows the full gating strategy used for analytical identification of mucosal emigrant and small bowel tropic Tcells in peripheral blood. Full enrichment is achieved by the addition of alpha4-integrin to the staining panel, allowing for exclusion of β7$^+$ cells that are α4 negative, a major contaminant using just β7+ criteria. An antibody for staining of a shared α4β7 epitope was not available for this study, though the two dimensional plot of these parameters reveals novel relationships as described in subsequent sections. FIGS. 23b and 23c show the staining of total PBMCs for the enriched parameters, demonstrating the strong enrichment of desired cell populations.

FIG. 24 displays the use of the gating strategy to analytically enrich Teffs and Tregs for comparison. Here FOXP3 vs CD25 is used to identify fixed cells. Exchanging FOXP3 for CD127 can be used to target viable cells. The very high enrichment of the target α4$^+$β7$^+$CCR9$^+$ small bowel tropic population can be seen within the total CD4 T-cell population (refer FIG. 23), and compared to the Teff population.

Addition of CD103 Mucosal Retention Marker Identifies Peripheral T-Cell Subsets

In the above data was presented that indicated two distinct populations of T-cells with regard to their positive expression of β7-integrin, a β7$^+$ and a β7$^{hi}$ population. It was shown that the β7$^{hi}$ population in both the small and large bowel LP displayed almost 100% CCR9 positivity, in healthy tissue. The quantitative difference in β7 expression is clearly due to the co-expression of a second integrin pair, in this case αE (CD103). The majority of β7$^+$ cells were presumed to be cells expressing solely the α4β7 pair, while β7$^{hi}$ cells express higher levels of β7 owing to the fact that they require additional β7 to pair with αE, suggesting β7$^{hi}$ cells express both the α4β7 and αEβ7 integrin pairs. The significance of this is that α4β7 is thought to be required for migration into mucosal tissues, while αEβ7 is required for retention.

Given that αEβ7 is regarded as a retention marker for mucosal T-cells, it is obvious why we observe high levels β7$^{hi}$ cells in mucosal tissues. What was not clear is why we observed a significantly greater proportion of β7$^{hi}$ cells in the small bowel, when compared to the large bowel (FIG. 1). An explanation comes from co-expression of CCR9 on β7$^{hi}$ cells. It is known that both αE and CCR9 are strongly induced by a similar set of stimuli, including ATRA and TGFbeta, which are likely to be provided by CD103$^+$ DCs in the LP and MLN environments. Cells recovered from the bowel LP thus represent cells that are being environmentally imprinted with α4β7 and αEβ7 integrin pairs and CCR9. Interestingly, CD103 is often cited as being of higher expression on CD4 Tregs, and has been proposed to be a defining marker of a subset of CD8 Tregs. This relationship was investigated in peripheral blood. Although CD103/αE is considered a mucosal retention marker, one does indeed observe CD103 positive cells in the peripheral blood. This is because the retention of αEβ7-expressing cells within mucosal tissue is likely to be directed by short-range homing. That is, cells that emigrate from the local mucosal tissues into blood stream will dominantly and selectively re-enter mucosa when expressing αEβ7 due to binding of cognate receptors (E-cadherin) on local (high endothelial venule) HEVs.

FIG. 25a presents an analysis of blood from a healthy donor where CD4 cells are gated and displayed as β7 vs α4 dotplots, as in FIGS. 7 and 8. Our expectation is that CD4 cells with a α4+β7$^{hi}$ phenotype will be highly enriched for CD103, and naturally CCR9 as a strongly co-expressed marker (note, figures designate β7$^{hi}$ as B7++). Cells within gates presented in FIG. 25a are displayed as CD103 vs CCR9 contour plots in FIG. 25b to FIG. 25e. As anticipated, the α4+β7$^{hi}$ population is highly enriched for CD103, with some 80% of all cells expressing CD103. This population is also highly enriched for CCR9 expression (FIG. 25b).

To confirm and expand the relationship between CD103 expression and the expression of α4 and β7- integrins, one can treat the same data in a differing manner. FIG. 26a simply shows gated CD4 cells as a CD4 vs CD103 dotplot. From here, total gated CD103- and CD103+ cells are displayed a β7 vs α4 dotplots in FIGS. 26b and 26c respectively. The negative population appears as a standard pool of CD4 T-cells with regard to β7 and α4 expression, although strikingly lack the expression of a α4+β7$^{hi}$ population (FIG. 26b). In contrast the CD103+ population is highly enriched for the α4+β7$^{hi}$ (FIG. 26bc, and compare FIG. 25a). We can also observe the enrichment of cells of another rare population, those that carry β7 expression, but lack α4. The tissue origin of these cells that likely express the αEβ7 pair in the absence of α4β7, is unclear.

Finally, this data can be used to visualise the quite clear expression of CD103 on the β7$^{hi}$ population (FIG. 27a). This CD4+β7$^{hi}$CD103+ population is highly enriched for α4+CCR9+ cells (FIGS. 27b and 27c).

Overall, these simple analyses demonstrate an analytical enrichment strategy for identifying CD4+α4+β7$^{hi}$αE+CCR9+ cells in the peripheral blood. These cells are likely to represent mucosal emigrants with a very strong propensity to recirculate to the small bowel. Therefore one could predict the CD4+α4+β7$^{hi}$αE+CCR9+ population to be highly represented in the CD38+CD62L- population. This is confirmed in the analyses presented in FIG. 28. Panels B) and C) display the now familiar parameters of total CD4 T-cells in a β7 vs α4 dotplot and CD38 vs CD62L dotplot, respectively, while panel A) displays CD103 vs CCR9 dotplot of total CD4 T-cells. Single positive CD103 cells are re-displayed in panel D), CD103 CCR9 double positives in panel E), and CCR9 single positives in panel F). These populations reveal the expected α4 and β7 staining consistent with above analyses. Both of the CD103 CCR9 double positive and CCR9 single positives show an enrichment of the CD38+CD62L- mucosal emigrant population. CCR9 single positives are also enriched for CD38+CD62L+, and are very likely to represent recent thymic emigrants.

In summary, the preliminary identification of CD4+α4+β7$^{hi}$αE+CCR9+ population in peripheral blood, which is likely to represent mucosal emigrants with a strong propensity to recirculate to the small bowel, presents a further means to identify Treg cells based on homing receptor patterns for adoptive immunotherapy. Coupled to Treg markers and the CD38CD62L marker sets, we are able to identify the signatures described with therapeutic potential in Crohn's disease, in particular the following two overlapping subsets of Tregs.
1) CD4+CD25$^{hi}$CD127$^{lo}$α4+β7$^{high}$αE+CCR9+
2) CD4+CD25$^{hi}$CD127$^{lo}$CD62L-CD38+α4+β7$^{high}$αE+CCR9+

The significance of the CD103+CD4 Treg population is underscored by the recent work defining the role of CCR9 in establishment of oral tolerance. A new theory suggests that dominant recirculation of iTregs from the LP back to the LP is required for establishment of oral tolerance in a CCR9-dependent manner. Thus, CD4+CD25$^{hi}$CD127$^{lo}$α4+β7$^{high}$αE+CCR9+ Tregs could represent a Treg population that makes a major contribution to intestinal homeostasis, despite their low numbers in the periphery.

To further confirm both thymic emigrant nature of CD4+CD38+CD62L+ cells, and indeed the expected antigen-experienced nature of CD4+CD38+CD62L- cells, the expression of CCR7 and CD45RA was analysed on these subpopulations. Firstly, FOXP3+ Tregs gated for CD38+CD62L+ were most highly enriched for CD45RA expression (FIG. 29e), supporting their enrichment for nave cells. In contrast, CD38+CD62L- cells expressed little CD45RA, and were enriched for CCR9 expression FIG. 29d). The recent thymic emigrant nature of CD4+CD25$^{hi}$CD127$^{lo}$CD38+CD62L+CCR9+ cells was further confirmed by the high enrichment of CCR7 expression within this population (FIG. 30e).

In order to more define the recent mucosal emigrant population of Treg cells of the small bowel, a high throughput screen was conducted using CD4+CD62L-CCR9+ as the test population (small bowel emigrant and tropic) and CD4+CD62L-CCR9-β7+ as the generally mucosal-tropic reference population. FIG. 31 shows an example of different adhesion molecule expression in the CD4+CD62L-CCR9+ population in comparison to the CD4+CD62L-CCR9-β7+ population that is targeted to mucosal tissues in general (FIG. 31 A to D). In this example, CD195 (CCR5) is almost absent in the CD4+CD62L-CCR9+ population. It is thus anticipated that CD195 may be used as a marker of preferred condition X-, with which to select for mucosal emigrant, immigrant and educated CD4+ Treg cells with small bowel tropism. The table presented in FIG. 31 E summarises other migratory-type markers associated with the CD4+CD62L-CCR9+ population. The markers positively correlated are of condition X+ and the markers negatively correlated are of condition X-. In the preferred aspect markers denoted X+ are used as a positive selection marker and markers denoted X- are used as a negative selection marker for the purification of mucosal emigrant, immigrant and educated CD4+ Treg cells with small bowel tropism. Each marker in this table is also assigned a class, where class 1 represents a strong association with the CD4+CD62L-CCR9+ population and high functional significance. Class 2 represents a strong association with the CD4+CD62L-CCR9+ population or high functional significance. Class 3 represents weak association and/or uncertain functional significance.

In a similar high throughout approach, the FIG. 32 shows an example of different adhesion molecule expression in the CD4+CD62L-CCR9-β7+ population in comparison to the CD4+CD62L-CCR9-β7- population (FIG. 32 A to C). In this example, CD29 (β1 integrin) is almost absent in the CD4$^+$CD62L$^-$CCR9$^-$β7$^+$ population. It is thus anticipated that CD29 may be used as a marker of preferred condition Y−, with which to select for mucosal emigrant, immigrant and educated CD4+ Treg cells. The table presented in FIG. 32 D summarises other migratory-type markers associated with the CD4$^+$CD62L$^-$CCR9$^-$β7$^+$ population. The markers positively correlated are of condition Y+ and the markers negatively correlated are of condition Y−. In the preferred aspect markers denoted Y+ are used as a positive selection marker and markers denoted Y− are used as a negative selection marker for the purification of mucosal emigrant, immigrant and educated CD4+ Treg cells. Marker class is defined and presented in table in FIG. 32D as above.

The aforementioned markers relate to tissue localisation, emigration, immigration and retention. In a similar experiment a high throughput screen was conducted to identify functional markers that are enriched within mucosal-tropic Treg populations when contrasted against mucosal-tropic cells that are non-treg in nature. Analyses of cells with CD4$^+$CD25$^{hi}$CD127$^{lo}$α4$^+$β7$^+$ character revealed strong enrichment of surface markers that denote regulatory function, and a restriction of markers that generally denote pro-inflammatory functions.

FIG. 33 shows an example of a functional marker, CD39 (ENTPD1), which is a putative immunosuppressive element on the surface of T-cells, and which is enriched in the CD4$^+$CD25$^{hi}$CD127$^{lo}$α4$^+$β7$^+$ population. It is thus anticipated that CD39 may be used as a marker of preferred condition Z+, with which to select for Treg cells within mucosal emigrant, immigrant and educated CD4+ T-cell populations. The table presented in FIG. 33D summarises other functional-type markers associated with the CD4$^+$CD25$^{hi}$CD127$^{lo}$α4$^+$β7$^+$ population. The markers positively correlated are of condition Z+, and largely represent entities with putative immunosuppressive activities, where in the preferred aspect they are used as a positive selection marker for the purification of Treg cells from mucosal emigrant, immigrant and educated CD4+ T-cell populations. The markers negatively correlated are of condition Z−, and largely represent entities with putative pro-inflammatory activities, where in the preferred aspect they are used as a negative selection marker for the purification of Treg cells from mucosal emigrant, immigrant and educated CD4+ T-cell populations. Each marker in this table is also assigned a class, where class 1 represents a strong association with the CD4$^+$CD25$^{hi}$CD127$^{lo}$α4$^+$β7$^+$ population and high functional significance. Class 2 represents a strong association with the CD4$^+$CD25$^{hi}$CD127$^{lo}$α4$^+$β7+ population or high functional significance. Class 3 represents weak association and/or uncertain functional significance.

In order to assess the feasibility of recovering the rare mucosal emigrant and tropic CD4 Tregs from peripheral circulation, CD4$^+$CD25$^{hi}$CD127$^{lo}$β7$^{hi}$CCR9$^+$ Tregs ere sorted from peripheral blood at high purity; PBMCs from healthy donors were labelled and sorted on the basis of these defined markers (FIG. 34). FIG. 34 *a* to *e* show the basic gating strategy of FACS-based purification of these cells, and FIGS. 34 *f* and *g* displays achieved purity of greater than 95%. FIGS. 34 *h* and *i* and *l* show that CD4$^+$CD25$^{hi}$CD127$^{lo}$β7$^{hi}$CCR9$^+$ target cells are largely of antigen experienced and recent activation character.

As proof of concept that, CD4$^+$CD25$^{hi}$CD127$^{1}$β7$^{hi}$CCR9$^+$ purified from peripheral blood of could be expanded as a therapeutic population, cells purified by FACS as described in FIG. 34 were expanded with recombinant stimuli in vitro. FIG. 35 displays a representative growth curve of such an expansion.

Finally, to test the hypothesis that mucosal emigrant CD4$^+$ Tregs in peripheral circulation are in some way clonally restricted due to their activated, emigrant and recirculating nature, an assessment of Vβ usage among CD4$^+$CD25$^{hi}$CD127$^{lo}$α4$^+$β7$^+$CD38$^+$CD62L$^-$CCR9$^+$ in peripheral circulation was conducted with total peripheral Tregs (CD4$^+$CD25$^{hi}$CD127$^{lo}$) as reference. (FIG. 36). Across three healthy donors, the usage of Vβ segments was markedly different between CD4$^+$CD25$^{hi}$CD127$^{lo}$α4$^+$β7$^+$CD38$^+$CD62L$^-$CCR9$^+$ and the total pool of CD4$^+$CD25$^{hi}$CD127$^{lo}$ lymphocytes. This indirectly supports the proposal that CD4$^+$CD25$^{hi}$CD127$^{lo}$α4$^+$β7$^+$CD38$^+$CD62L$^-$CCR9$^+$ mucosal emigrant Tregs are activated against a restricted set of antigens in the mucosa, and exported for recirculation in order to support regional and/or systemic tolerance.

Experimental—Material and Methods
Material

Fluorochrome-conjugated antibodies were obtained from BD Biosciences or BioLegend; CD4-FITC, CD4-PE/Cy7 (OKT4), CD25-APC (2A3, M-A251), CD25-PE/Cy7 (BC960, M-A251), CD38-BV421 (HIRT2), CD38-PE (HIT2), CD45RO-PerCP/Cy5.5 (UCHL1) CD49d-PE/Cy7 (9F10), CD62L-PE/Cy7 (DREG-56), CD127-PerCP/Cy5.5, CD127-PE (A019D5, HIL-7R-M21), FOXP3-PE (259D/C7), FOXP3-AlexaFluor647 (206D), integrinβ7-PerCP/Cy5.5, integrinβ7-FITC (FIB27) CD62L BV421 (DREG-55), CD4 BV510 (SK3), CD25 BV605 (2A3), CD1c PE (L161), CD3 FITC (HIT3a), CD3 PE-CF594 (UCHT1), CD3 APC-H7 (SK7), CD4 BV605 (RPA-T4), CD4 PerCP (SK3), CD4 APC (RPA-T4), CD4 APC-H7 (RPA-T4), CD8 BV510 (RPA-T8), CD8 BV605 (SK1), CD8 BV786 (RPA-T8), CD8 Alexa 488 (RPA-T8), CD8 PerCP-Cy5.5 (RPA-T8), CD8 PE (RPA-T8), CD8 PE-Cy7 (RPA-T8), CD8 APC-H7 (SK1), CD11a PE (HI111), CD11 b BV510 (ICRF44), CD11 b PE-Cy7 (ICRF44), CD11c BV421 (B-ly6), CD11c BV605 (B-ly6), CD11c PE (B-ly6), CD14 BV510 (MφP9), CD14 BV711 (MφP9), CD14 APC (M5E2), CD16 PerCP-Cy5.5 (3G8), CD16 PE (B73.1), CD18 BV421 (6,7), CD19 BV510 (SJ25C1), CD19 BV711 (SJ2501), CD19 PE-Cy7 (SJ25C1), CD25 BV510 (M-A251), CD25 BV786 (M-A251), CD25 PerCP-Cy5.5 (M-A251), CD25 PE-Cy7 (M-A251), CD28 BV421 (CD28.2), CD28 BV605 (CD28.2), CD28 BV711 (CD28.2), CD28 FITC (CD28.2), CD28 PE-Cy7 (CD28.2), CD28 PerCP-Cy5.5 (CD28.2), CD28 APC-H7 (CD28.2), CD29 BV510 (MAR4), CD29 PE (MAR4), CD29 APC (MAR4), CD31 BV605 (WM59), CD38 FITC (HIT2CD38), PE-CF594 (HIT2CD38), PE-Cy7 (HIT2CD38), Alexa700 (HIT2), CD38 APC-H7 (HB7), CD39 BV711 (Tü66), CD39 FITC (Tü66), CD45 BV605 (HI30), CD45 BV786 (HI30), CD45 FITC (HI30), CD45 PE (HI30), CD45 PE-Cy7 (HI30), CD45RA BV421 (HI100), CD45RA BV605 (HI100), CD45RA BV711 (HI100), CD45RA PerCP-Cy5.5 (HI100), CD45RA PE (HI100), CD45RO BV605 (UCHL1), CD45RO BV711 (UCHL1), CD45RO APC (UCHL1), CD49a PE (SR84), CD49b PE (12F1), CD49c PE (C3 II.1), CD49d BV510 (9F10), CD49d BV711 (9F10), CD49d PerCP-Cy5.5 (9F10), CD49d PE (9F10), CD49d PE-CF594 (9F10), CD49e PE (IIA1), CD49f PE (GoH3), CD56 BV510 (NCAM16.2), CD56 BV711 (NCAM16.2), CD62L BV510 (DREG-56), CD62L BV605 (DREG-56), CD69 BV605 (FN50), CD69 BV711 (FN50), CD69 PerCP-Cy5.5 (FN50), CD69 PE-Cy7 (FN50), CD73 BV605 (AD2), CD79a BV421 (HM47), CD79a PE (HM47), CD79a APC (HM47), CD79b PE (3A2-2E7), CD79b PE-Cy5 (CB3-1), CD80 BV605 (L307.4), CD80 PE (L307.4), CD80 PE-Cy7 (L307.4), CD80 APC (2D10), CD83 PerCP-Cy5.5 (HB15e), CD83 APC (HB15e), CD86 BV421 (2331), CD86 PerCP-Cy5.5 82331), CD86 APC (2331), CD103 BV711 (Ber-ACT8), CD103 FITC (Ber-ACT8), CD103 PE (Ber-ACT8), CD127 BV421 (HIL-7R-M21), CD127 BV605 (HIL7R-M21), CD127 BV650 (HIL-7R-M21), CD127 BV711 (HIL-7R-M21), CD127 FITC (HIL-7R-M21), CD141 BV510 (1A4), CD141 PE (1A4), CD152 BV421 (BNI3), CD152 BV786 (BNI3), CD163 PerCP-Cy5.5 (GHI/61), CD192 BV421 (K03602), CD196 BV421 (11A9), CD197 FITC (3D12), CD197 PerCP-Cy5.5 (150503), CD199 Alexa 488 (112509), CD199 FITC (112509), CD199 PE (112509), CD199 PE (L053E8), CD199 PE (248621), CD199 PE-Cy7 (L053E8), CD199 Alexa 647 (112509), CD199 Alexa 647 (L053E8), CD199 Alexa 647 (BL/CCR9), CD199 APC (112509), CD303 BV421 (201A), CD357 APC (621), Annexin V APC, β7 integrin BV421 (FIB504), β7 integrin BV605 (FIB504), β7 integrin PE (FIB504), β7 integrin APC (FIB504), CX3CR1 PerCP-Cy5.5 (2A9-1), FoxP3 Alexa 488 (259D/C7), Granzyme B BV421 (GB11), Granzyme B FITC (GB11), Granzyme B PE-CF594 (GB11), Helios PE (22F6), HLA-A2 PE-Cy7 (BB7.2), HLA-A,B,C PE-Cy5 (G46-2.6), HLA-E PE (3D12), HLA-G PE (87G), HLA-DM PE (MaP.DM1), HLA-DR PerCP-Cy5.5 (G46-6), HLA-DR PE-Cy7 (G46-6), HLA-DR APC (G46-6), HLA-DRB1, HLA-DR, DP, DQ FITC (Tü39), HLA-DR, DP, DQ Alexa 647 (Tü39), HLA-DQ FITC (Tu169), IFN-g Alexa 647 (4S.B3), IL-1b PE (AS10), IL-2 FITC (MQ1-17H12), IL-2 FITC (MQ1-17H12), IL-4 FITC (MP4-25D2), IL-10 APC (JES3-19F1), IL-12 FITC (C11.5), IL-17A PE (SCPL1362), IL-35 PE (B032F6), Ig κ light chain PE (G20-193), Light chain λ PE (JDC-12), IgM BV605 (G20-127), IgM FITC (G20-127), IgM FITC IgM PE-Cy5 (G20-127), Lineage cocktail FITC, Perforin BV421 (5G9), Perforin Alexa 488 (5G9), Syk FITC (4D10), Syk PY352 PE (17A/P-ZAP70), Syk PY352 PE-Cy7 (17A/P-ZAP70), Syk PY352 Alexa 647 (17A/P-ZAP70), TCR αβ BV510 (T10139.1A-31), TCR αβ BV786 (T10139.1A-31), TCR γδ FITC (B1), TCR γδ-1 FITC (11F2), TCR γδ PE-CF594 (B1), TGF-b1 BV421 (TW4-9E7), TNF-a APC (MAb11), and unlabelled antibodies were obtained from BD Biosciecnes; CD1a (HI149), CD28 (L293), CD51/61 (2306), CD1b (M-T101), CD29 (HUTS-21), CD53 (HI29), CD1d (CD1d42), CD30 (BerH8), CD54 (LB-2), CD2 (RPA-2.10), CD31 (WM59), CD55 (IA10), CD3 (HIT 3a), CD32 (FL18.26), CD56 (B159), CD4 (RPA-T4), CD33 (HIM3-4), CD57 (NK-1), CD4v4 (L120), CD34 (581), CD58 (1C3), CD5 (L17F12), CD35 (E11), CD59 (p282, H19), CD6 (M-T605), CD36 (CB38, NL07), CD61 (VI-PL2), CD7 (M-T701), CD37 (M-B371), CD62E (68-5H11), CD8a (SK1), CD38 (HIT 2), CD62L (Dreg 56), CD8b (2ST 8.5H7), CD39 (TU66), CD62P (AK-4), CD9 (M-L13), CD40 (503), CD63 (H506), CD10 (HI10a), CD41a (HIP8), CD64 (10.1), CD11a (G43-25B), CD41b (HIP2), CD66 (a,c,d,e) (B1.1/CD66), CD11 b (D12), CD42a (ALMA.16), CD66b (G10F5), CD11c (B-ly 6), CD42b (HIP1), CD66f (11D1), CD13 (WM15), CD43 (1G10), CD69 (FN50), CD14 (M5E2), CD44 (G44-26), CD70 (Ki-24), CD15 (HI98), CD45 (HI30), CD71 (M-A712), CD15s (CSLEX1), CD45RA (HI100), CD72 (J4-117), CD16 (3G8), CD45RB (MT4), CD73 (AD2), CD18 (6.7), CD45RO (UCHL1), CD74 (M-B741), CD19 (HIB19), CD46 (E4.3), CD75 (LN1), CD20 (2H7), CD47 (B6H12), CD77 (5B5), CD21 (B-ly 4), CD48 (T U145), CD79a (CB3-1), CD22 (HIB22 CD49a SR84 CD80 L307.4 CD23 EBVCS-5 CD49b AK-7 CD81 JS-81), CD24 (ML5), CD49c (C3 II.1), CD83 (HB15e), CD25 (M-A251), CD49d (9F10), CD84 (2G7), CD26 (M-A261), CD49e (VC5), CD85 (GHI/75), CD27 (M-T271), CD50 (TU41), CD86 (2331, FUN-1), CD123 (9F5), CD172b (B4B6), CD87 (VIM5), CD124 (hIL4R-M57), CD177 (MEM-166), CD88 (D53-1473), CD126 (M5), CD178 (NOK-1), CD89 (A59), CD127 (hIL-7R-M21), CD180 (G28-8), CD90 (5E10), CD128b (6C6), CD181 (5A12), CD91 (A2MR-alpha 2), CD130 (AM64), CD183 (1C6/CXCR3), CDw93 (R139), CD134 (ACT35), CD184 (12G5), CD94 (HP-3D9), CD135 (4G8), CD193 (5E8), CD95 (DX2), CD137 (4B4-1), CD195 (2D7/CCR5), CD97 (VIM3b), CD137 (Ligand 065-485), CD196 (11A9), CD98 (UM7F8), CD138 (Mi15), CD197 (2H4), CD99 (TU12), CD140a (alpha R1), CD200 (MRC OX-104), CD99R (HIT 4), CD140b (28D4), CD205 (MG38), CD100 (A8), CD141 (1A4), CD206 (19.2), CD102 (CBR-1C2/2.1), CD142 (HTF-1), CD209 (DCN46), CD103 (Ber-ACT8), CD144 (55-7H1), CD220 (3B6/IR), CD105 (266), CD146 (P1H12), CD221 (3B7), CD106 (51-10C9), CD147 (HIM6), CD226 (DX11), CD107a (H4A3), CD150 (A12), CD227 (HMPV), CD107b (H464), CD151 (14A2.H1), CD229 (HLy9.1.25), CD108 (KS-2), CD152 (BNI3), CD231 (M3-3D9, SN1a), CD109 (TEA 2/16), CD153 (D2-1173), CD235a (GA-R2, HIR2), CD112 (R2.525), CD154 (TRAP1), CD243 (17F9), CD114 (LMM741), CD158a (HP-3E4), CD244 (2-69), CD116 (M5D12), CD158b (CH-L), CD255 (CARL-1), CD117 (Y B5.B8), CD161 (DX12), CD268 (11C1), CD118 (12D3), CD162 (KPL-1), CD271 (C40-1457), CD119 (GIR-208), CD163 (GHI/61), CD273 (MIH18), CD120a (MABTNFR1-A1), CD164 (N6B6), CD274 (MIH1), CD121a (HIL1R-M1), CD165 (SN2), CD275 (2D3/67-H2), CD121b (MNC2), CD166 (3A6), CD278 (DX29), CD122 (Mik-beta 3), CD171 (5G3), CD279 (MIH4), fMLP receptor (5F1), Ms IgG2a IC (G155-178), CD282 (11G7), γδTCR (B1), Ms IgG2b IC (27-35), CD305 (DX26), HPC (BB9), Ms IgG3 IC (J606), CD309 (89106), HLA-A,B,C (G46-2.6), CD49f (GoH3), CD314 (1D11), HLA-A2 (BB7.2), CD104 (439-9B), CD321 (M.AB.F11), HLA-DQ (TU169), CD120b (hTNFR-M1), CDw327 (E20-1232), HLA-DR (G46-6, L243), CD132 (TUGh4), CDw328 (F023-420), HLA-DR, DP, DQ (TU39), CD201 (RCR-252), CDw329 (E10-286), Invariant NK T (61311), CD210 (3F9), CD335 (9E2/NKp46), Disialoganglioside GD2 (14.G2a), CD212 (2B6/12beta 2), CD336 (P44-8.1), MIC A/B (6D4), CD267 (1A1-K21-M22), CD337 (P30-15), NKB1 (DX9), CD294 (BM16), CD338 (5D3), SSEA-1 (MC480), SSEA-3 (MC631), CD304 (Neu24.7), SSEA4 (MC813-70), CLA (HECA-452), αβT CR (T10139.1A-31), TRA-1-60 (TRA-1-60), Integrin β7 (F16504), β2-microglobulin (TU99), TRA-1-81 (TRA-1-81), Rt IgM IC (R4-22), BLTR-1 (203/14F11), Vβ 23 (AHUT 7), Rt IgG1 IC (R3-34), CLIP (CerCLIP), Vβ 8 (JR2), Rt IgG2a IC (R35-95), CMRF-44 (CMRF44), CD326 (EBA-1), Rt IgG2b IC (A95-1), CMRF-56 (CMRF56), Ms IgM IC (G155-228), EGF Receptor (EGFR1), Ms IgG1 IC (MOPC-21) and Zombie NIR™ Fixable Viability Kit or BD Biosciences; CD4-PacificBlue (RPA-T4); collagenaseIV, DNaseI, DTT, EDTA and sodium azide from SigmaAldrich; FicollPaquePlus from GEHealthcare, RPMI media, BSA and FCS from Life Technologies; IOTest Beta Mark TCR V Kit from Beckman Coulter.

Patients and Tissue Preparation

All subjects gave their written informed consent under the Helsinki guidelines and local ethics committee. CD patients undergoing ileoceacal resection were recruited to the study. We collected small bowel (ileum) and large bowel (ceacum/ascending colon), including MLN draining these regions. Control samples were from colorectal cancer patients undergoing right-sided hemicolectomy. Intestinal lamina propria from the small and large bowel was separated via microdissection. The dissected lamina propria was minced into 1-2 mm pieces and single cell suspensions were prepared in RPMI 1640 containing 5% FBS, 50 μg/ml gentamycin and 50 μg/ml Penicillin/Streptomycin using the Medimachine with a 50 μm Medicon (BD Biosciences). The cell suspension was filtered through a 70-μm nylon mesh (BD Biosciences), centrifuged and the pellet resuspended in FACS buffer (PBS containing 2% FBS) for subsequent antibody staining.

Lymphocytes from MLN were isolated by mechanical disruption of lymph nodes after surrounding fat tissue was removed by dissection. The cell suspension was filtered through a 40-μm nylon mesh (BD Biosciences), centrifuged and the pellet resuspended in FACS buffer for subsequent antibody staining.

Patients and Blood Preparation

All subjects gave their written informed consent under the Helsinki guidelines and local ethics committee. Healthy donors were recruited to the blood cohorts. Blood drawn into EDTA tubes was diluted 1:2 in PBS with 2 mM EDTA and PBMCs collected over a FicollPaquePlus density gradient by centrifugation. PBMCs were washed 3 times in wash buffer (PBS, 0.2% BSA, 5 mM EDTA) before immediate flow cytometry.

Direct Cell Purification by FACS

Extracellular antigens were stained in FACS buffer (PBS, 2% BSA) using appropriate combinations of fluorophore-conjugated antibodies (BioLegend and BD Biosciences). Specific cell populations were purified by fluorescence-activated cell sorting (FACS) using a BD Influx cell sorter with BD FACS Sortware (BD Biosciences) to acquire data. Final analyses utilized FlowJo software (Tree Star Inc.).

Expansion of Sorted Cell Populations

The sorted cell populations were expanded in OpTmizer media with 2 mM Glutamax (both Life Technologies) and either autologous or commercial human serum (Sigma) using MACS GMP ExpAct Treg Kit (Miltenyi Biotec) and in the presence of recombinant human IL-2 (Miltenyi Biotec).

Flow Cytometry

Zombie NIR Fixable Viability Kit (Biolegend) was used as a dead cell marker. Surface antigens were stained in FACS buffer (PBS containing 2% FBS) and intracellular FoxP3 was stained after fixation and permeabilization using the human FoxP3 buffer set (BD Biosciences). Cells were acquired using a LSRFortessa flow cytometer with Diva 8 software (BD Biosciences). Final analysis was performed using FlowJo 10 software (Tree Star Inc.).

Statistics

All data was expressed as mean±SEM. Pair wise comparisons were two-tailed Mann-Whitney U-tests. Significance testing of multiple parameters was calculated with Kruskal-Wallis one-way ANOVA and Dunn's post-test of selected columns. A p value<0.05 was considered significant.

Items

1. Treg cells for use in the treatment of an inflammatory disease of the gastrointestinal tract, the Treg cells have signatures for i) identifying that the T-cells are regulatory Tcells, ii) identifying that the Treg cells are tissue type tropic, i.e they can migrate to the diseased tissue, iii) identifying that the Treg cells are tropic with respect to the diseased tissue of the gastrointestinal tract, i.e. they are homing cells, iv) identifying that the Treg cells are emigrant cells, i.e. they originate from the target tissue of gastrointestinal tract, and/or v) identifying that the Treg cells are retained in the target tissue of the gastrointestinal tract, wherein the Treg cells have the signatures i), ii) and iii) and optionally iv) and/or v), or the Treg cells have the signatures i), ii) and v) and optionally iii) and/or iv), or the Treg cells have the signatures i), iii) and optionally ii) and/or v).

2. Tregs for use according to item 1, wherein the inflammatory disease is Crohn's disease or ulcerative colitis.

3. Tregs for use according to item 2, wherein the disease is Crohn's disease which is located in the small bowel.

4. Treg cells for use according to any of the preceding items for the treatment of an inflammatory disease of the small bowel, the Treg cells have signatures for i) identifying that the T-cells are regulatory Tcells, ii) identifying that the Treg cells are mucosal tropic, iii) identifying that the Treg cells are small bowel tropic, and optionally the Treg cells have signatures for iv) identifying that the Treg cells are emigrant cells, i.e. they originate from the small bowel, and/or v) identifying that the Treg cells are retained in the small bowel.

5. Treg cells for use according to item 4 having signatures for iv) identifying that the Treg cells are emigrant cells, i.e. they originate from the small bowel.

6. Treg cells for use according to any of items 3-5 having signatures for v) identifying that the Treg cells are retained in the small bowel.

7. Treg cells for use according to any of the preceding items, wherein the signatures for identifying that the T-cells are regulatory T-cells are CD4$^+$CD25$^{hi}$CD127$^{lo}$ or CD4$^+$CD25$^{hi}$.

8. Treg cells for use according to any of the preceding items, wherein the signature for identifying that the Treg cells can migrate to the diseased tissue such as the mucosal tissue is α4β7$^+$ or α4$^+$β7$^+$.

9. Treg cells for use according to any of the preceding items, wherein the signature for identifying that the Treg cells can be retained in the diseased tissue such as the mucosal tissue is α4β7$^{high}$αE$^+$ or α4$^+$β7$^{high}$αE$^+$.

10. Treg cells for use according to any of the items 3-9, wherein the signatures for identifying that the Treg cells are small bowel tropic is CCR9$^+$.

11. Treg cells for use according to any of the preceding items, wherein the signatures for identifying that the Treg cells are educated cells (emigrants) is CD62L$^-$CD38$^+$.

12. Treg cells for use according to any of the preceding items, wherein the Treg cells comprise a signature selected from the following signatures:

CD4$^+$CD25$^{hi}$CD127$^{lo}$α4$^+$β7$^+$CCR9$^+$,

CD4$^+$CD25$^{hi}$CD127$^{lo}$α4β7$^+$CCR9$^+$,

CD4$^+$CD25$^{hi}$CD127$^{lo}$α4$^+$β7$^{high}$αE$^+$CCR9$^+$,

CD4$^+$CD25$^{hi}$CD127$^{lo}$CD62L$^-$CD38$^+$α4$^+$β7$^+$CCR9$^+$

CD4$^+$CD25$^{hi}$CD127$^{lo}$CD62L$^-$CD38$^+$α4$^+$β7$^{high}$αE$^+$CCR9$^+$

CD4$^+$α4β7$^{high}$αE$^+$CCR9$^+$

CD4$^+$CD25$^{hi}$CD127$^{lo}$α4$^+$β7$^+$X$^+$

CD4$^+$CD25$^{hi}$CD127$^{lo}$α4$^+$β7$^{high}$αE$^+$X$^+$

CD4$^+$CD25$^{hi}$CD127$^{lo}$CD62L$^-$CD38$^+$α4$^+$β7$^+$X$^+$

CD4$^+$CD25$^{hi}$CD127$^{lo}$CD62L$^-$CD38$^+$α4$^+$β7$^{high}$αE$^+$X$^+$

CD4$^+$α4$^+$β7$^{high}$αE$^+$X$^+$

CD4$^+$CD25$^{hi}$CD127$^{lo}$α4$^+$β7$^+$

CD4$^+$CD25$^{hi}$CD127$^{lo}$α4$^+$β7$^{high}$αE$^+$

CD4$^+$CD25$^{hi}$CD127$^{lo}$CD62L$^-$CD38$^+$α4$^+$β7$^+$ $CD4^+CD25^{hi}CD127^{lo}CD62L^-CD38^+\alpha4^+\beta7^{high}\alpha E^+$
$CD4^+\alpha4^+\beta7^{high}\alpha E^+$, and
any of the signatures may also comprise $CD62L^-CD38^+$ and wherein $\alpha4^+$ may be substituted with $\alpha4$.

13. Treg cells for use according to any of items 3-12, wherein the small bowel disease is Crohn's disease.

14. A method for treating a patient suffering from an inflammatory disease of the gastrointestinal tract, the method comprises
a) isolating Treg cells defined in any one of items 1-13 from a tissue sample obtained from a patient suffering from the inflammatory disease of the gastrointestinal tract,
b) expanding the Treg cells in vitro,
c) optionally re-patterning the expanded Treg cells to obtain Tregs that have signatures ii) and iii) and optionally iv) and/or v), or signatures for iii) and v) and optionally ii) and/or iv) or signatures for ii) and optionally iii), iv) and/or v), wherein the signatures is for
ii) identifying that the Treg cells are tissue type tropic,
iii) identifying that the Treg cells are diseased tissue tropic,
iv) identifying that the Treg cells are emigrant cells, i.e. they originate from the target tissue, and/or
v) identifying that the Treg cells are retained in the target tissue,
d) administering the Treg cells obtained from b) or c) to the patient.

15. A method according to item 14, wherein the expanded Treg cells from step b) or c) have features as defined in any one of items 1-13.

16. A method according to item 14 or 15, wherein the tissue sample is from peripheral blood of the patient.

17. A method according to any of items 12-15, wherein the inflammatory disease of the gastrointestinal tract is Crohn's disease.

18. A method for obtaining Treg cells as defined in any one of items 1-13, the method comprises
a) isolating Treg cells defined in any one of items 1-13 from a tissue sample obtained from a patient suffering from an inflammatory disease of the gastrointestinal tract,
b) expanding the Treg cells in vitro,
c) optionally re-patterning the expanded Treg cells to obtain Tregs that have signatures signatures ii) and iii) and optionally iv) and/or v), or signatures for iii) and v) and optionally ii) and/or iv) or signatures for ii) and optionally iii), iv) and/or v), wherein the signatures is for
ii) identifying that the Treg cells are tissue type tropic,
iii) identifying that the Treg cells are diseased tissue tropic relating to the diseased part of the gastrointestinal tract,
iv) identifying that the Treg cells are emigrant cells, i.e. the originates from the target tissue of the gastrointestinal tract, and/or
v) identifying that the Treg cells are retained in the target tissue of the gastrointestinal tract.

19. A method according to item 18, wherein the inflammatory disease of the gastrointestinal tract is Crohn's disease such as Crohn's disease located in the small bowel.

20. A method according to item 18 or 19, wherein step a) comprises the recovery of mononuclear cells from patient tissue specimens, and labelling said pool of mononuclear cells with antibodies specific for appropriate markers; once labelled, cells are purified by immunoaffinity and/or flow cytometric sorting techniques to yield highly enriched or purified Treg populations of desired characteristics.

21. A method according to any of items 18-20 wherein step b) comprises recombinant T-cell stimulation in the form of anti-CD3/anti-CD28 activating antibodies in combination with IL2, or alternatively the outgrowth of Treg populations on transgenic feeder cell populations, or irradiated autologous peripheral monocytes with IL2 supplementation.

22. A method according to any of items 18-21, wherein step c) comprises the recombinant reactivation of expanded T-cell populations with anti-CD3/anti-CD28 activating antibodies and subsequent introduction of stimuli in precise combination. Stimuli include all-trans retinoic acid, Interleukin-10 and transforming growth factor-beta.

23. A method for obtaining Treg cells as defined in any one of items 1-13, the method comprising
a) providing Treg cells comprising a signature selected from $CD4^+CD25^{hi}CD127^{lo}$,
$CD4^+CD25^{hi}CD127^{lo}\beta7^{high}\alpha E^+$,
$CD4^+CD25^{hi}CD127^{lo}CD62L^-CD38^+$ and
$CD4^+CD25^{hi}CD127^{lo}CD62L^-CD38^+\beta7^{high}\alpha E^+$ and
b) re-patterning the Treg cells to further comprise the signature $\alpha4\beta7^+$, $\alpha4^+\beta7^+$, $\alpha4\beta7^+CCR9^+$ or $\alpha4^+\beta7^+CCR9^+$.

24. A method according to item 23, wherein step b) comprises the recombinant reactivation of expanded T-cell populations with anti-CD3/anti-CD28 activating antibodies and subsequent introduction of stimuli including all-trans retinoic acid, Interleukin-10 and transforming growth factor-beta 25. A method for obtaining Treg cells as defined in any one of items 1-13, the method comprising
a) providing Treg cells comprising a signature selected from $CD4^+CD25^{hi}CD127^{lo}CCR9^+$,
$CD4^+CD25^{hi}CD127^{lo}\alpha E^+\beta7^{high}CCR9^+$,
$CD4^+CD25^{hi}CD127^{lo}CD62L^-CD38^+CCR9^+$ and
$CD4^+CD25^{hi}CD127^{lo}CD62L^-CD38^+\alpha E^+\beta7^{high}CCR9^+$. and
b) re-patterning the Treg cells to further comprise the signature $\alpha4\beta7^+$ or $\alpha4^+\beta7^+$.

26. A method according to item 24, wherein step b) comprises the recombinant reactivation of expanded T-cell populations with anti-CD3/anti-CD28 activating antibodies and subsequent introduction of stimuli including all-trans retinoic acid, Interleukin-10 and transforming growth factor-beta.

27. A pharmaceutical composition comprising Treg cells as defined in any of items 1-13 dispersed in an aqueous medium.

28. Treg cells as defined in any of items 1-13.

The invention claimed is:
1. A method for treating a patient suffering from an inflammatory or autoimmune disease of the gastrointestinal tract, comprising:
(a) obtaining an isolated CD4+Treg cell population from a patient suffering from the disease, wherein the CD4+ Treg cell population consists of cells having the following signatures:
(i) one or more signatures identifying that the T-cells are CD4+regulatory T cells, selected from $CD4^+CD25^{hi}$, $CD4^+CD25^{hi}CD127^{lo}$, $CD4^+CD25^{hi}Z_n$, and $CD4^+CD25^{hi}CD127^{lo}Z_n$, wherein n indicates that one or more Z signatures may be present;
(ii) one or more signatures identifying that the CD4+ Treg cells are mucosal tissue type tropic that can migrate to diseased gastrointestinal mucosal tissue selected from $\alpha4\beta7^+$, $\alpha4^+\beta7^+$, $\alpha4\beta7^+Y_n$, and $\alpha4\beta7^+Y_n$, wherein n indicates that one or more Y signatures may be present;
(iii) optionally, a signature identifying that the CD4+ Treg cells are homing cells tropic with respect to the diseased mucosal tissue, wherein the signature is for localization in the small bowel and is selected from $CCR9^+$ and $CCR9^+X_n$, wherein n indicates that one or more X signatures may be present;

(iv) one or more signatures identifying that the CD4$^+$ Treg cells are mucosal emigrant cells that originated from the target mucosal tissue, selected from one or more of CD62L; CD38$^+$, and α4$^+$αE$^+$β7$^{high}$, optionally further in combination with one or more of X$_n$, Y$_p$ and X$_n$Y$_p$, wherein n and p indicate that one or more X signatures and one or more Y signatures, respectively, may be present; and (v) optionally, a signature identifying that the CD4$^+$ Treg cells are retained in the target mucosal tissue, selected from α4$^+$αE$^+$β7$^{hi}$ and/or α4$^+$β7$^+$αE$^+$, optionally further in combination with one or more of X$_n$, Y$_p$, Z$_q$, X$_n$Y$_p$, X$_n$Z$_q$, and Y$_p$Z$_q$, wherein n, p and q indicate that one or more X signatures, one or more Y signatures, and one or more Z signatures, respectively, may be present; and (vi) optionally further having one or more X-signatures and/or one or more Y-signatures and/or one or more Z-signatures, wherein X is a signature indicating that the CD4$^+$Treg cells can localize, have emigrated from, or are marked for preferential retention in the specific part of the gastrointestinal tract that is diseased, and is one or more selected from CD26$^-$, CD97$^-$, CD143$^-$, CD195$^-$, CD278$^+$, CD61$^-$, CD63$^-$, CD146$^-$, CD183$^-$, CD197$^+$, CD200$^+$, CD244$^-$, CD20$^-$, CD130$^+$, and CD166$^-$;

Y is a signature indicating that the CD4$^+$Treg cells can localize to any mucosal surface, and is one or more selected from CD29$^-$, CD38$^+$, CD49c$^-$, CD49e$^-$, CD102$^-$, CD147$^-$, (e) CD15s$^-$, CD27$^+$, CD49b$^-$, CD84$^-$, CD119$^+$, CD161$^+$, CD184$^+$, CD305$^+$, (f) CD71$^-$, CD126$^-$, CD134$^-$, CD151$^+$, CD171$^-$, CD196$^-$, CD227$^-$, and CD49f; and Z is a signature indicating regulatory function or restriction of inflammatory function, and is one or more selected from CD21$^-$, CD35$^-$, CD73$^-$, CD122$^+$, CLIP$^+$, CD120b$^+$, CD6$^-$, CD39$^+$, CD50$^+$, CD109$^+$, CD226$^-$, CD243$^-$, CD268$^+$, CD274$^-$, CD210$^+$, CD49c$^+$, CD53$^+$, CD84$^-$, CD95$^+$, and CD107a$^-$, and wherein the isolated CD4$^+$Treg cell population has T-cell receptor clonal diversity restricted to clonotypes specific for antigens present in the mucosal tissue types to which the selected signatures relate, (b) expanding the CD4$^+$Treg cell population in vitro, (c) optionally, re-patterning the expanded CD4$^+$Treg cells to obtain expanded CD4$^+$Treg cells that have said signatures, wherein the signatures resulting from (b) or (c)

(i) identify that the CD4$^+$Treg cells are mucosal tissue type tropic, (ii) optionally identify that the CD4$^+$Treg cells are diseased mucosal tissue tropic, (iii) identify that the CD4$^+$Treg cells are mucosal emigrant cells that originate from the target mucosal tissue, and (iv) optionally identify that the CD4$^+$Treg cells are capable of retention in the target mucosal tissue, and (d) administering the CD4$^+$Treg cells obtained from (b) or (c) to the patient.

2. The method according to claim 1, wherein the CD4$^+$ Treg cell population is obtained from peripheral blood of the patient.

3. The method according to claim 1, wherein the diseased mucosal tissue originates from inflamed tissue or tissue subject to an autoimmune disease.

4. The method according to claim 1, wherein the isolated CD4$^+$Treg cell population comprises CD4$^+$Treg cells having at least one of the following signatures:

CD4$^+$CD25$^{hi}$α4β7$^+$CD62L$^-$CD38$^+$
CD4$^+$CD25$^{hi}$α4$^+$β7$^+$CD62L$^-$CD38$^+$
CD4$^+$CD25$^{hi}$CD127$^{lo}$α4β7$^+$CD62L$^-$CD38$^+$
CD4$^+$CD25$^{hi}$CD127$^{lo}$α4$^+$β7$^+$CD62L$^-$CD38$^+$
CD4$^+$CD25$^{hi}$α4β7$^+$CD62L$^-$
CD4$^+$CD25$^{hi}$α4$^+$β7$^+$CD62L$^-$
CD4$^+$CD25$^{hi}$CD127$^{lo}$α4β7$^+$CD62L$^-$
CD4$^+$CD25$^{hi}$CD127$^{lo}$α4$^+$β7$^+$CD62L$^-$
CD4$^+$CD25$^{hi}$α4β7$^+$CD62L$^-$CD38$^+$CCR9$^+$
CD4$^+$CD25$^{hi}$α4$^+$β7$^+$CD62L$^-$CD38$^+$CCR9$^+$
CD4$^+$CD25$^{hi}$CD127$^{lo}$α4β7$^+$CD62L$^-$CD38$^+$CCR9$^+$
CD4$^+$CD25$^{hi}$CD127$^{lo}$α4$^+$β7$^+$CD62L$^-$CD38$^+$CCR9$^+$
CD4$^+$CD25$^{hi}$α4β7$^+$CD62L$^-$CCR9$^+$
CD4$^+$CD25$^{hi}$α4$^+$β7$^+$CD62L$^-$CCR9$^+$
CD4$^+$CD25$^{hi}$CD127$^{lo}$α4β7$^+$CD62L$^-$CCR9$^+$
CD4$^+$CD25$^{hi}$CD127$^{lo}$α4$^+$β7$^+$CD62L$^-$CCR9$^+$
CD4$^+$CD25$^{hi}$α4β7$^{high}$αE$^+$CD62L$^-$CD38$^+$
CD4$^+$CD25$^{hi}$α4$^+$β7$^{high}$αE$^+$CD62L$^-$CD38$^+$
CD4$^+$CD25$^{hi}$CD127$^{lo}$α4β7$^{hi}$αE$^+$CD62L$^-$CD38$^+$
CD4$^+$CD25$^{hi}$CD127$^{lo}$α4$^+$β7$^{hi}$αE$^+$CD62L$^-$CD38$^+$
CD4$^+$CD25$^{hi}$α4β7$^{high}$αE$^+$CD62L$^-$
CD4$^+$CD25$^{hi}$α4$^+$β7$^{high}$αE$^+$CD62L$^-$
CD4$^+$CD25$^{hi}$CD127$^{lo}$α4β7$^{hi}$αE$^+$CD62L$^-$
CD4$^+$CD25$^{hi}$CD127$^{lo}$α4$^+$β7$^{hi}$αE$^+$CD62L$^-$
CD4$^+$CD25$^{hi}$α4β7$^{high}$αE$^+$CD38$^+$
CD4$^+$CD25$^{hi}$α4$^+$β7$^{high}$αE$^+$CD38$^+$
CD4$^+$CD25$^{hi}$CD127$^{lo}$α4β7$^{hi}$αE$^+$CD38$^+$
CD4$^+$CD25$^{hi}$CD127$^{lo}$α4$^+$β7$^{hi}$αE$^+$CD38$^+$
CD4$^+$CD25$^{hi}$α4β7$^{high}$αE$^+$CD62L$^-$CD38$^+$CCR9$^+$
CD4$^+$CD25$^{hi}$α4$^+$β7$^{high}$αE$^+$CD62L$^-$CD38$^+$CCR9$^+$
CD4$^+$CD25$^{hi}$CD127$^{lo}$α4β7$^{hi}$αE$^+$CD62L$^-$CD38$^+$CCR9$^+$
CD4$^+$CD25$^{hi}$CD127$^{lo}$α4$^+$β7$^{hi}$αE$^+$CD62L$^-$CD38$^+$CCR9$^+$
CD4$^+$CD25$^{hi}$α4β7$^{high}$αE$^+$CD62L$^-$CCR9$^+$
CD4$^+$CD25$^{hi}$α4$^+$β7$^{high}$αE$^+$CD62L$^-$CCR9$^+$
CD4$^+$CD25$^{hi}$CD127$^{lo}$α4β7$^{hi}$αE$^+$CD62L$^-$CCR9$^+$
CD4$^+$CD25$^{hi}$CD127$^{lo}$α4$^+$β7$^{hi}$αE$^+$CD62L$^-$CCR9$^+$
CD4$^+$CD25$^{hi}$α4β7$^{high}$αE$^+$CD38$^+$CCR9$^+$
CD4$^+$CD25$^{hi}$α4$^+$β7$^{high}$αE$^+$CD38$^+$CCR9$^+$
CD4$^+$CD25$^{hi}$CD127$^{lo}$α4β7$^{hi}$αE$^+$CD38$^+$CCR9$^+$ and
CD4$^+$CD25$^{hi}$CD127$^{lo}$α4$^+$β7$^{hi}$αE$^+$CD38$^+$CCR9$^+$.

5. The method according to claim 1, wherein the isolated CD4$^+$Treg cell population comprises CD4$^+$Treg cells having at least one of the following signatures:

CD4$^+$CD25$^{hi}$α4β7$^+$CD62L$^-$CD38$^+$X/Y/Z
CD4$^+$CD25$^{hi}$α4$^+$β7$^+$CD62L$^-$CD38$^+$X/Y/Z
CD4$^+$CD25$^{hi}$αCD127$^{lo}$α4β7$^+$CD62L$^-$CD38$^+$X/Y/Z
CD4$^+$CD25$^{hi}$CD127$^{lo}$α4$^+$β7$^+$CD62L$^-$CD38$^+$X/Y/Z
CD4$^+$CD25$^{hi}$α4β7$^+$CD62L$^-$X/Y/Z
CD4$^+$CD25$^{hi}$α4$^+$β7$^+$CD62L$^-$X/Y/Z
CD4$^+$CD25$^{hi}$CD127$^{lo}$α4β7$^+$CD62L$^-$X/Y/Z
CD4$^+$CD25$^{hi}$CD127$^{lo}$α4$^+$β7$^+$CD62L$^-$X/Y/Z
CD4$^+$CD25$^{hi}$α4β7$^+$CD38$^+$X/Y/Z
CD4$^+$CD25$^{hi}$α4$^+$β7$^+$CD38$^+$X/Y/Z
CD4$^+$CD25$^{hi}$CD127$^{lo}$α4β7$^+$CD38$^+$X/Y/Z
CD4$^+$CD25$^{hi}$CD127$^{lo}$α4$^+$β7$^+$CD38$^+$X/Y/Z
CD4$^+$CD25$^{hi}$α4β7$^+$CD62L$^-$CD38$^+$CCR9$^+$X/Y/Z
CD4$^+$CD25$^{hi}$α4$^+$β7$^+$CD62L$^-$CD38$^+$CCR9$^+$X/Y/Z
CD4$^+$CD25$^{hi}$CD127$^{lo}$α4β7$^+$CD62L$^-$CD38$^+$CCR9$^+$X/Y/Z
CD4$^+$CD25$^{hi}$CD127$^{lo}$α4$^+$β7$^+$CD62L$^-$CD38$^+$CCR9$^+$X/Y/Z

CD4+CD25^hi α4β7+CD62L−CCR9+X/Y/Z
CD4+CD25^hi α4+β7+CD62L−CCR9+X/Y/Z
CD4+CD25^hi α4β7+CD62L−CCR9+X/Y/Z
CD4+CD25^hi CD127^lo α4+β7+CD62L−CCR9+X/Y/Z
CD4+CD25^hi α4β7+CD38+CCR9+X/Y/Z
CD4+CD25^hi α4+β7+CD38+CCR9+X/Y/Z
CD4+CD25^hi CD127^lo α4β7+CD38+CCR9+X/Y/Z
CD4+CD25^hi CD127^lo α4+β7+CD38+CCR9+X/Y/Z
CD4+CD25^hi α4β7^high αE+CD62L−CD38+X/Y/Z
CD4+CD25^hi α4+β7^high αE+CD62L−CD38+X/Y/Z
CD4+CD25^hi CD127^lo α4β7^hi αE+CD62L−CD38+X/Y/Z
CD4+CD25^hi CD127^lo α4+β7^hi αE+CD62L−CD38+X/Y/Z
CD4+CD25^hi α4β7^high αE+CD62L−X/Y/Z
CD4+CD25^hi α4+β7^high αE+CD62L−X/Y/Z
CD4+CD25^hi CD127^lo α4β7^hi αE+CD62L−X/Y/Z
CD4+CD25^hi CD127^lo α4+β7^hi αE+CD62L−X/Y/Z
CD4+CD25^hi α4β7^high αE+CD38+X/Y/Z
CD4+CD25^hi α4+β7^high αE+CD38+X/Y/Z
CD4+CD25^hi CD127^lo α4β7^hi αE+CD38+X/Y/Z
CD4+CD25^hi CD127^lo α4+β7^hi αE+CD38+X/Y/Z
CD4+CD25^hi α4β7^high αE+CD62L−CD38+CCR9+X/Y/Z
CD4+CD25^hi α4+β7^high αE+CD62L−CD38+CCR9+X/Y/Z
CD4+CD25^hi CD127^lo α4β7^hi αE+CD62L−CD38+CCR9+X/Y/Z
CD4+CD25^hi CD127^lo α4+β7^hi αE+CD62L−CD38+CCR9+X/Y/Z
CD4+CD25^hi α4β7^high αE+CD62L−CCR9+X/Y/Z
CD4+CD25^hi α4+β7^high αE+CD62L−CCR9+X/Y/Z
CD4+CD25^hi CD127^lo α4β7^hi αE+CD62L−CCR9+X/Y/Z
CD4+CD25^hi CD127^lo α4+β7^hi αE+CD62L−CCR9+X/Y/Z
CD4+CD25^hi α4β7^high αE+CD38+CCR9+X/Y/Z
CD4+CD25^hi α4+β7^high αE+CD38+CCR9+X/Y/Z
CD4+CD25^hi CD127^lo α4β7^hi αE+CD38+CCR9+X/Y/Z
and
CD4+CD25^hi CD127^lo α4+β7^hi αE+CD38+CCR9+X/Y/Z,
wherein "X/Y/Z" means that at least one of X and/or at least one of Y and/or at least one of Z is present, wherein X may be X+ or X−, Y may be Y+ or Y−, and Z may be Z+ or Z−.

6. The method according to claim 1, wherein the isolated CD4+Treg cell population comprises CD4+Treg cells having at least one of the following signatures:
CD4+CD25^hi α4β7+CD62L−CD38+X
CD4+CD25^hi α4+β7+CD62L−CD38+X
CD4+CD25^hi CD127^lo α4β7+CD62L−CD38+X
CD4+CD25^hi CD127^lo α4+β7+CD62L−CD38+X
CD4+CD25^hi α4β7+CD62L−CD38+CCR9+X
CD4+CD25^hi α4+β7+CD62L−CD38+CCR9+X
CD4+CD25^hi CD127^lo α4β7+CD62L−CD38+CCR9+X
CD4+CD25^hi CD127^lo α4+β7+CD62L−CD38+CCR9+X
CD4+CD25^hi α4β7^high αE+CD62L−CD38+X
CD4+CD25^hi α4+β7^high αE+CD62L−CD38+X
CD4+CD25^hi CD127^lo α4β7^hi αE+CD62L−CD38+X
CD4+CD25^hi CD127^lo α4+β7^hi αE+CD62L−CD38+X
CD4+CD25^hi α4β7^high αE+CD62L−CD38+CCR9+X
CD4+CD25^hi α4+β7^high αE+CD62L−CD38+CCR9+X
CD4+CD25^hi CD127^lo α4β7^hi αE+CD62L−CD38+CCR9+X
CD4+CD25^hi CD127^lo α4+β7^hi αE+CD62L−CD38+CCR9+X
CD4+CD25^hi α4β7+CD62L−CD38+Y
CD4+CD25^hi α4+β7+CD62L−CD38+Y
CD4+CD25^hi CD127^lo α4β7+CD62L−CD38+Y
CD4+CD25^hi CD127^lo α4+β7+CD62L−CD38+Y
CD4+CD25^hi α4β7+CD62L−CD38+CCR9+Y
CD4+CD25^hi α4+β7+CD62L−CD38+CCR9+Y
CD4+CD25^hi CD127^lo α4β7+CD62L−CD38+CCR9+Y
CD4+CD25^hi CD127^lo α4+β7+CD62L−CD38+CCR9+Y
CD4+CD25^hi α4β7^high αE+CD62L−CD38+Y
CD4+CD25^hi α4+β7^high αE+CD62L−CD38+Y
CD4+CD25^hi CD127^lo α4β7^hi αE+CD62L−CD38+Y
CD4+CD25^hi CD127^lo α4+β7^hi αE+CD62L−CD38+Y
CD4+CD25^hi α4β7^high αE+CD62L−CD38+CCR9+Y
CD4+CD25^hi α4+β7^high αE+CD62L−CD38+CCR9+Y
CD4+CD25^hi CD127^lo α4β7^hi αE+CD62L−CD38+CCR9+Y
CD4+CD25^hi CD127^lo α4+β7^hi αE+CD62L−CD38+CCR9+Y
CD4+CD25^hi α4β7+CD62L−CD38+Z
CD4+CD25^hi α4+β7+CD62L−CD38+Z
CD4+CD25^hi CD127^lo α4β7+CD62L−CD38+Z
CD4+CD25^hi CD127^lo α4+β7+CD62L−CD38+Z
CD4+CD25^hi α4β7+CD62L−CD38+CCR9+Z
CD4+CD25^hi α4+β7+CD62L−CD38+CCR9+Z
CD4+CD25^hi CD127^lo α4β7+CD62L−CD38+CCR9+Z
CD4+CD25^hi CD127^lo α4+β7+CD62L−CD38+CCR9+Z
CD4+CD25^hi α4β7^high αE+CD62L−CD38+Z
CD4+CD25^hi α4+β7^high αE+CD62L−CD38+Z
CD4+CD25^hi CD127^lo α4β7^hi αE+CD62L−CD38+Z
CD4+CD25^hi CD127^lo α4+β7^hi αE+CD62L−CD38+Z
CD4+CD25^hi α4β7^high αE+CD62L−CD38+CCR9+Z
CD4+CD25^hi α4+β7^high αE+CD62L−CD38+CCR9+Z
CD4+CD25^hi CD127^lo α4β7^hi αE+CD62L−CD38+CCR9+Z
CD4+CD25^hi CD127^lo α4+β7^hi αE+CD62L−CD38+CCR9+Z
CD4+CD25^hi α4β7+CD62L−CD38+XY
CD4+CD25^hi α4+β7+CD62L−CD38+XY
CD4+CD25^hi CD127^lo α4β7+CD62L−CD38+XY
CD4+CD25^hi CD127^lo α4+β7+CD62L−CD38+XY
CD4+CD25^hi α4β7+CD62L−CD38+CCR9+XY
CD4+CD25^hi α4+β7+CD62L−CD38+CCR9+XY
CD4+CD25^hi CD127^lo α4β7+CD62L−CD38+CCR9+XY
CD4+CD25^hi CD127^lo α4+β7+CD62L−CD38+CCR9+XY
CD4+CD25^hi α4β7^high αE+CD62L−CD38+XY
CD4+CD25^hi α4+β7^high αE+CD62L−CD38+XY
CD4+CD25^hi CD127^lo α4β7^hi αE+CD62L−CD38+XY
CD4+CD25^hi CD127^lo α4+β7^hi αE+CD62L−CD38+XY
CD4+CD25^hi α4β7^high αE+CD62L−CD38+CCR9+XY
CD4+CD25^hi α4+β7^high αE+CD62L−CD38+CCR9+XY
CD4+CD25^hi CD127^lo α4β7^hi αE+CD62L−CD38+CCR9+XY
CD4+CD25^hi CD127^lo α4+β7^hi αE+CD62L−CD38+CCR9+XY
CD4+CD25^hi α4β7+CD62L−CD38+XZ
CD4+CD25^hi α4+β7+CD62L−CD38+XZ
CD4+CD25^hi CD127^lo α4β7+CD62L−CD38+XZ
CD4+CD25^hi CD127^lo α4+β7+CD62L−CD38+XZ
CD4+CD25^hi α4β7+CD62L−CD38+CCR9+XZ
CD4+CD25^hi α4+β7+CD62L−CD38+CCR9+XZ
CD4+CD25^hi CD127^lo α4β7+CD62L−CD38+CCR9+XZ
CD4+CD25^hi CD127^lo α4+β7+CD62L−CD38+CCR9+XZ
CD4+CD25^hi α4β7^high αE+CD62L−CD38+XZ
CD4+CD25^hi α4+β7^high αE+CD62L−CD38+XZ
CD4+CD25^hi CD127^lo α4β7^hi αE+CD62L−CD38+XZ
CD4+CD25^hi CD127^lo α4+β7^hi αE+CD62L−CD38+XZ
CD4+CD25^hi α4β7^high αE+CD62L−CD38+CCR9+XZ
CD4+CD25^hi α4+β7^high αE+CD62L−CD38+CCR9+XZ
CD4+CD25^hi CD127^lo α4β7^hi αE+CD62L−CD38+CCR9+XZ
CD4+CD25^hi CD127^lo α4+β7^hi αE+CD62L−CD38+CCR9+XZ
CD4+CD25^hi α4β7+CD62L−CD38+YZ
CD4+CD25^hi α4+β7+CD62L−CD38+YZ CD4$^+$CD25$^{hi}$CD127$^{lo}$α4β7$^+$CD62L$^-$CD38$^+$YZ
CD4$^+$CD25$^{hi}$CD127$^{lo}$α4$^+$β7$^+$CD62L$^-$CD38$^+$YZ
CD4$^+$CD25$^{hi}$α4β7$^+$CD62L$^-$CD38$^+$CCR9$^+$YZ
CD4$^+$CD25$^{hi}$α4$^+$β7$^+$CD62L$^-$CD38$^+$CCR9$^+$YZ
CD4$^+$CD25$^{hi}$CD127$^{lo}$α4β7$^+$CD62L$^-$CD38$^+$CCR9$^+$YZ
CD4$^+$CD25$^{hi}$CD127$^{lo}$α4$^+$β7$^+$CD62L$^-$CD38$^+$CCR9$^+$YZ
CD4$^+$CD25$^{hi}$α4β7$^{high}$αE$^+$CD62L$^-$CD38$^+$YZ
CD4$^+$CD25$^{hi}$α4$^+$β7$^{high}$αE$^+$CD62L$^-$CD38$^+$YZ
CD4$^+$CD25$^{hi}$CD127$^{lo}$α4β7$^{hi}$αE$^+$CD62L$^-$CD38$^+$YZ
CD4$^+$CD25$^{hi}$CD127$^{lo}$α4$^+$β7$^{hi}$αE$^+$CD62L$^-$CD38$^+$YZ
CD4$^+$CD25$^{hi}$α4β7$^{high}$αE$^+$CD62L$^-$CD38$^+$CCR9$^+$YZ
CD4$^+$CD25$^{hi}$α4$^+$β7$^{high}$αE$^+$CD62L$^-$CD38$^+$CCR9$^+$YZ
CD4$^+$CD25$^{hi}$CD127$^{lo}$α4β7$^{hi}$αE$^+$CD62L$^-$CD38$^+$CCR9$^+$YZ and
CD4$^+$CD25$^{hi}$CD127$^{lo}$α4β7$^{hi}$αE$^+$CD62L$^-$CD38$^+$CCR9$^+$YZ,
wherein X may be X$^+$or X$^-$, Y may be Y$^+$or Y$^-$, and Z may be Z$^+$or Z.

7. The method according to claim 1, wherein CD4$^+$Treg cells in the isolated CD4+Treg cell population do not include Treg cells having one or more of the following signatures: CD62L$^+$, CCR9$^+$CD45RA$^+$, CCR9$^+$CCR7$^+$, CCR9$^+$CD62L$^+$, CCR9$^+$CD45RO$^-$and CCR9$^+$CCR7$^+$CD62L$^+$CD45RA$^+$CD45RO$^-$.

8. The method according to claim 1, wherein CD4$^+$Treg cells in the isolated CD4+Treg cell population further have one or more signatures denoting recent activation selected from CD69$^+$and CD44$^+$.

9. The method according to claim 1, wherein the CD4$^+$ Treg cells in the isolated CD4+Treg cell population are suspended in a saline-based solution having a physiological pH, and further comprising an additive to promote cell survival and/or stability and/or cryopreservation.

10. The method of claim 1, wherein the inflammatory or autoimmune disease is selected from Crohn's disease and ulcerative colitis.

11. The method of claim 1, wherein the inflammatory or autoimmune disease is selected from primary sclerosing cholangitis and acute celiac disease.

\* \* \* \* \*

UNITED STATES PATENT AND TRADEMARK OFFICE
CERTIFICATE OF CORRECTION

PATENT NO. : 10,758,568 B2
APPLICATION NO. : 15/303866
DATED : September 1, 2020
INVENTOR(S) : Jarvis et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 484 days.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*